(12) United States Patent
Man et al.

(10) Patent No.: US 7,569,232 B2
(45) Date of Patent: Aug. 4, 2009

(54) MEDIUM CHAIN PEROXYCARBOXYLIC ACID COMPOSITIONS

(75) Inventors: Victor Fuk-Pong Man, St. Paul, MN (US); Joshua Paul Magnuson, St. Paul, MN (US); Steven Eugene Lentsch, St. Paul, MN (US)

(73) Assignee: Ecolab Inc., St. Paul, MN (US)

( * ) Notice: Subject to any disclaimer, the term of this patent is extended or adjusted under 35 U.S.C. 154(b) by 83 days.

(21) Appl. No.: 11/030,641

(22) Filed: Jan. 4, 2005

(65) Prior Publication Data

US 2005/0192197 A1  Sep. 1, 2005

Related U.S. Application Data

(63) Continuation-in-part of application No. 10/754,426, filed on Jan. 9, 2004.

(51) Int. Cl.
| | |
|---|---|
| *A61K 33/40* | (2006.01) |
| *A61K 31/19* | (2006.01) |
| *A61K 31/20* | (2006.01) |
| *A61K 9/66* | (2006.01) |
| *A61K 33/42* | (2006.01) |
| *A01N 37/00* | (2006.01) |
| *A01N 25/00* | (2006.01) |
| *A01N 39/00* | (2006.01) |

(52) U.S. Cl. .................. 424/405; 424/455; 424/601; 424/613; 424/616; 514/557; 514/558

(58) Field of Classification Search ................ 514/557, 514/558; 424/405, 455, 601, 613, 616
See application file for complete search history.

(56) References Cited

U.S. PATENT DOCUMENTS

| | | | |
|---|---|---|---|
| 2,512,640 A | 6/1950 | Greenspan et al. | |
| 3,122,417 A | 2/1964 | Blaser et al. | |
| 3,248,281 A | 4/1966 | Goodenough | |
| 3,350,265 A | 10/1967 | Rubinstein et al. | |
| 3,514,278 A | 5/1970 | Brink | |
| 3,895,116 A | 7/1975 | Herting et al. | |
| 3,996,386 A | 12/1976 | Malkki et al. | |
| 4,041,149 A | 8/1977 | Gaffar et al. | |
| 4,051,058 A | 9/1977 | Bowing et al. | |
| 4,051,059 A | 9/1977 | Bowing et al. | |
| 4,129,517 A | 12/1978 | Eggensperger et al. | |
| 4,191,660 A | 3/1980 | Schreiber et al. | |
| 4,244,884 A | 1/1981 | Hutchins et al. | |
| 4,289,728 A | 9/1981 | Peel et al. | |
| 4,370,199 A | 1/1983 | Orndorff | |
| 4,404,040 A | 9/1983 | Wang | |
| 4,477,438 A | 10/1984 | Willcockson et al. | |
| 4,478,683 A | 10/1984 | Orndorff | |
| 4,501,681 A | 2/1985 | Groult et al. | |
| 4,529,534 A | 7/1985 | Richardson | |
| 4,557,898 A | 12/1985 | Greene et al. | |
| 4,566,980 A | 1/1986 | Smith | |
| 4,591,565 A | 5/1986 | Branner-Jorgensen | |
| 4,592,488 A | 6/1986 | Simon et al. | |
| 4,613,452 A | 9/1986 | Sanderson | |
| 4,655,781 A | 4/1987 | Hsieh et al. | |
| 4,659,494 A | 4/1987 | Soldanski et al. | |
| 4,666,622 A | 5/1987 | Martin et al. | |
| 4,683,618 A | 8/1987 | O'Brien | |
| 4,704,404 A | 11/1987 | Sanderson | |
| 4,715,980 A | 12/1987 | Lopes et al. | |
| 4,738,840 A | 4/1988 | Simon et al. | |
| 4,802,994 A | 2/1989 | Mouché et al. | |
| 4,834,900 A | 5/1989 | Soldanski et al. | |
| 4,865,752 A | 9/1989 | Jacobs | |
| 4,900,721 A | 2/1990 | Bansemir et al. | |
| 4,906,617 A | 3/1990 | Jacquet et al. | |
| 4,908,306 A | 3/1990 | Lorincz | |
| 4,917,815 A | 4/1990 | Beilfuss et al. | |
| 4,923,677 A | 5/1990 | Simon et al. | |
| 4,937,066 A | 6/1990 | Vlock | |
| 4,943,414 A | 7/1990 | Jacobs et al. | |
| 4,945,110 A | 7/1990 | Brokken et al. | |
| 4,996,062 A | 2/1991 | Lehtonen et al. | |
| 4,997,571 A | 3/1991 | Roensch et al. | |
| 4,997,625 A | 3/1991 | Simon et al. | |
| 5,004,760 A | 4/1991 | Patton et al. | |
| 5,010,109 A | 4/1991 | Inoi | |

(Continued)

FOREIGN PATENT DOCUMENTS

CA    2181416    1/1997

(Continued)

OTHER PUBLICATIONS

International Search Report dated May 3, 2005.

(Continued)

*Primary Examiner*—Ernst V Arnold
(74) *Attorney, Agent, or Firm*—Andrew D. Sorensen; Anneliese S. Mayer

(57) ABSTRACT

The present invention relates to compositions including medium chain peroxycarboxylic acid, methods for making these compositions, and methods for reducing the population of a microorganism. The compositions can include advantageously high levels of the medium chain peroxycarboxylic acid, can be readily made, and/or can exhibit reduced odor.

14 Claims, 1 Drawing Sheet

U.S. PATENT DOCUMENTS

| | | |
|---|---|---|
| 5,015,408 A | 5/1991 | Reuss |
| 5,043,176 A | 8/1991 | Bycroft et al. |
| 5,069,286 A | 12/1991 | Roensch et al. |
| 5,078,896 A | 1/1992 | Rorig et al. |
| 5,084,239 A | 1/1992 | Moulton et al. |
| 5,093,140 A | 3/1992 | Watanabe |
| 5,114,178 A | 5/1992 | Baxter |
| 5,122,538 A | 6/1992 | Lokkesmoe et al. |
| 5,129,824 A | 7/1992 | Keller |
| 5,130,124 A | 7/1992 | Merianos et al. |
| 5,139,788 A | 8/1992 | Schmidt |
| 5,168,655 A | 12/1992 | Davidson et al. |
| 5,176,899 A | 1/1993 | Montgomery |
| 5,184,471 A | 2/1993 | Losacco et al. |
| 5,200,189 A | 4/1993 | Oakes et al. |
| 5,208,057 A | 5/1993 | Greenley et al. |
| 5,234,703 A | 8/1993 | Guthery |
| 5,234,719 A | 8/1993 | Richter et al. |
| 5,266,587 A | 11/1993 | Sankey et al. |
| 5,268,003 A | 12/1993 | Coope et al. |
| 5,292,447 A | 3/1994 | Venturello et al. |
| 5,314,687 A | 5/1994 | Oakes et al. |
| 5,320,805 A | 6/1994 | Kramer et al. |
| 5,336,500 A | 8/1994 | Richter et al. |
| 5,364,650 A | 11/1994 | Guthery |
| 5,391,324 A | 2/1995 | Reinhardt et al. |
| 5,409,713 A | 4/1995 | Lokkesmoe et al. |
| 5,419,908 A | 5/1995 | Richter et al. |
| 5,435,808 A | 7/1995 | Holzhauer et al. |
| 5,436,008 A | 7/1995 | Richter et al. |
| 5,437,868 A | 8/1995 | Oakes et al. |
| 5,489,434 A | 2/1996 | Oakes et al. |
| 5,489,706 A | 2/1996 | Revell |
| 5,494,588 A | 2/1996 | LaZonby |
| 5,508,046 A | 4/1996 | Cosentino et al. |
| 5,512,309 A | 4/1996 | Bender et al. |
| 5,527,898 A | 6/1996 | Bauer et al. |
| 5,545,343 A | 8/1996 | Brougham et al. |
| 5,545,374 A | 8/1996 | French et al. |
| 5,578,134 A | 11/1996 | Lentsch et al. |
| 5,591,706 A | 1/1997 | Ploumen |
| 5,595,967 A | 1/1997 | Miracle et al. |
| 5,597,790 A | 1/1997 | Thoen |
| 5,616,335 A | 4/1997 | Nicolle et al. |
| 5,616,616 A | 4/1997 | Hall et al. |
| 5,624,634 A | 4/1997 | Brougham et al. |
| 5,632,676 A | 5/1997 | Kurschner et al. |
| 5,641,530 A | 6/1997 | Chen |
| 5,656,302 A | 8/1997 | Cosentino et al. |
| 5,658,467 A | 8/1997 | LaZonby et al. |
| 5,658,595 A | 8/1997 | Van Os |
| 5,674,538 A | 10/1997 | Lokkesmoe et al. |
| 5,674,828 A | 10/1997 | Knowlton et al. |
| 5,683,724 A | 11/1997 | Hei et al. |
| 5,712,239 A | 1/1998 | Knowlton et al. |
| 5,718,910 A | 2/1998 | Oakes et al. |
| 5,720,983 A | 2/1998 | Malone |
| 5,756,139 A | 5/1998 | Harvey et al. |
| 5,785,867 A | 7/1998 | LaZonby et al. |
| 5,840,343 A | 11/1998 | Hall et al. |
| 5,851,483 A | 12/1998 | Nicolle et al. |
| 5,891,392 A | 4/1999 | Monticello et al. |
| 5,900,256 A | 5/1999 | Scoville, Jr. et al. |
| 5,902,619 A | 5/1999 | Rubow et al. |
| 5,962,392 A | 10/1999 | Revell et al. |
| 5,968,539 A | 10/1999 | Beerse et al. |
| 5,989,611 A | 11/1999 | Stemmler, Jr. et al. |
| 5,998,358 A | 12/1999 | Herdt et al. |
| 6,008,405 A | 12/1999 | Gray et al. |
| 6,010,729 A | 1/2000 | Gutzmann et al. |
| 6,024,986 A | 2/2000 | Hei |
| 6,028,104 A | 2/2000 | Schmidt et al. |
| 6,033,705 A | 3/2000 | Isaacs |
| 6,039,992 A | 3/2000 | Compardre et al. |
| 6,049,002 A | 4/2000 | Mattila et al. |
| 6,080,712 A | 6/2000 | Revell et al. |
| 6,096,226 A | 8/2000 | Fuchs et al. |
| 6,096,266 A | 8/2000 | Duroselle |
| 6,096,348 A | 8/2000 | Miner et al. |
| 6,103,286 A | 8/2000 | Gutzmann et al. |
| 6,113,963 A | 9/2000 | Gutzmann et al. |
| 6,165,483 A | 12/2000 | Hei et al. |
| 6,183,807 B1 | 2/2001 | Gutzmann et al. |
| 6,238,685 B1 | 5/2001 | Hei et al. |
| 6,257,253 B1 | 7/2001 | Lentsch et al. |
| 6,274,542 B1 | 8/2001 | Carr et al. |
| 6,302,968 B1 | 10/2001 | Baum et al. |
| 6,395,703 B2 | 5/2002 | Scepanski |
| 6,451,746 B1 | 9/2002 | Moore et al. |
| 6,514,556 B2 | 2/2003 | Hilgren et al. |
| 6,545,047 B2 | 4/2003 | Gutzmann et al. |
| 6,627,657 B1 * | 9/2003 | Hilgren et al. ............... 514/553 |
| 6,630,439 B1 | 10/2003 | Norwood et al. |
| 6,635,286 B2 | 10/2003 | Hei et al. |
| 6,638,902 B2 | 10/2003 | Tarara et al. |
| 2002/0128312 A1 | 9/2002 | Hei et al. |
| 2002/0168422 A1 * | 11/2002 | Hei et al. .................... 424/661 |
| 2003/0070691 A1 | 4/2003 | Giletto et al. |
| 2003/0087786 A1 | 5/2003 | Hei et al. |
| 2003/0199583 A1 | 10/2003 | Gutzmann et al. |

FOREIGN PATENT DOCUMENTS

| | | |
|---|---|---|
| DE | 30 03 875 A1 | 8/1981 |
| DE | 35 43 500 A1 | 6/1987 |
| DE | 39 06 044 A1 | 8/1990 |
| DE | 0538/9310 | 5/1993 |
| DE | 197 51 391 A1 | 7/1998 |
| DK | 9300538 | 11/1994 |
| EP | 0 125 781 | 11/1984 |
| EP | 0 140 648 | 5/1985 |
| EP | 0 167 375 | 1/1986 |
| EP | 0 186 052 | 7/1986 |
| EP | 0 195 619 A2 | 9/1986 |
| EP | 0 233 731 A2 | 8/1987 |
| EP | 0 233 731 | 9/1987 |
| EP | 0 242 990 A2 | 10/1987 |
| EP | 0 361 955 A2 | 4/1990 |
| EP | 0 404 293 A2 | 12/1990 |
| EP | 0 460 962 | 12/1991 |
| EP | 0 461 700 A1 | 12/1991 |
| EP | 0 569 066 A1 | 11/1993 |
| EP | 0 603 329 | 6/1994 |
| EP | 0 667 392 A2 | 2/1995 |
| EP | 0 779 357 A1 | 12/1995 |
| EP | 0 805 198 A1 | 7/1996 |
| EP | 0 843 001 A1 | 11/1996 |
| EP | 0 967 203 | 12/1999 |
| EP | 0 985 349 A2 | 3/2000 |
| EP | 1 382 666 A1 | 1/2004 |
| FR | 2 321 301 A | 3/1977 |
| FR | 2 324 626 A | 4/1977 |
| FR | 2 578 988 | 9/1986 |
| GB | 1 570 492 | 11/1975 |
| GB | 2 182 051 | 5/1987 |
| GB | 2 187 958 | 9/1987 |
| GB | 2 207 354 | 2/1989 |
| GB | 2 255 507 | 11/1992 |
| GB | 2 257 630 | 1/1993 |
| GB | 2 353 800 | 3/2001 |
| GR | 1 494 109 | 12/1977 |
| JP | 7-31210 | 2/1995 |
| JP | 7-258005 | 10/1995 |
| LU | 78 568 A | 4/1978 |

| | | |
|---|---|---|
| NL | 9201631 | 9/1992 |
| RU | 212447 C1 | 8/1996 |
| WO | WO 93/01716 | 2/1993 |
| WO | WO 94/06294 | 3/1994 |
| WO | WO 94/14321 | 7/1994 |
| WO | WO 94/15465 | 7/1994 |
| WO | WO 94/21122 | 9/1994 |
| WO | WO 94/23575 | 10/1994 |
| WO | WO 95/34537 | 12/1995 |
| WO | WO 96/30474 | 10/1996 |
| WO | WO 98/28267 | 7/1998 |
| WO | WO 99/51095 | 10/1999 |
| WO | WO 00/18870 | 4/2000 |
| WO | WO 01/47359 | 7/2001 |
| WO | WO 02/03799 | 1/2002 |
| WO | WO 02/054866 | 7/2002 |
| WO | WO 02/060280 | 8/2002 |
| WO | WO 2004/043162 | 5/2004 |

OTHER PUBLICATIONS

International Search Report dated Jul. 4, 2005 (PCT/US2005/000147).
International Search Report dated Jun. 28, 2005 (PCT/US2005/000149).
International Search Report dated Jun. 28, 2005 (PCT/US2005/000231).
Civil Docket Sheet for Case No. 0:05-cv-00831-JMR-FLN printed Sep. 26, 2006.
Complaint with attached Exhibits A, B and C, filed Apr. 26, 2005.
Answer to Complaint, Affirmative Defenses, and Counterclaim with attached Exhibit 1, filed Aug. 11, 2005.
Plaintiff's Reply to Defendant's Counterclaim, filed Aug. 31, 2005.
Plaintiff Ecolab Inc.'s Motion for Leave to File its First Amendment Complaint, filed Sep. 8, 2005.
Amended Complaint, filed Oct. 12, 2005.
Answer to Amended Complaint, Affirmative Defenses, and Counterclaim, filed Oct. 26, 2005.
FMC Corporations Motion for Leave to File its Amended Answered, Affirmative Defenses, and Counter Claim, filed Apr. 14, 2006.
Memorandum of Law in Support of FMC Corporation's Motion for Leave to File its Amended Answer, Affirmative Defenses, and Counterclaim, filed Apr. 14, 2006.
Declaration of Francis DiGiovanni Submitted in Support of FMC Corporation's Motion for Leave to File its Amended Answer, Affirmative Defenses, and Counter Claim, filed Apr. 14, 2006.
The Partial European Search Report prepared and filed by the European Patent Office in EPO application No. EP 99 11 6261, which is an EPO counterpart to the application that resulted in Ecolab's U.S. patent 6,010,729—(Exhibit A for Declaration of Francis DiGiovanni Submitted in Support of FMC Corporation's Motion for Leave to File its Amended Answer, Affirmative Defenses, and Counter Claim, filed Apr. 14, 2006).
A communication from the EPO on EPO application No. EP 99 11 6261—(Exhibit B for Declaration of Francis DiGiovanni Submitted in Support of FMC Corporation's Motion for Leave to File its Amended Answer, Affirmative Defenses, and Counter Claim, filed Apr. 14, 2006).
A communication to the EPO from counsel for Ecolab Inc. regarding EPO application NO. EP 99 11 6261—(Exhibit C for Declaration of Francis DiGiovanni Submitted in Support of FMC Corporation's Motion for Leave to File its Amended Answer, Affirmative Defenses, and Counter Claim, filed Apr. 14, 2006).
Ecolab's "Supplemental Answer to Interrogatory No. 2 and Second Supplemental Answer to Interrogatory No. 14," served Apr. 3, 2006—(Exhibit D for Declaration of Francis DiGiovanni Submitted in Support of FMC Corporation's Motion for Leave to File its Amended Answer, Affirmative Defenses, and Counter Claim, filed Apr. 14, 2006.
Plaintiff Ecolab Inc.'s Motion for Leave to File its Second Amended Complaint, filed Apr. 14, 2006.
Memorandum of Law in Support of Plaintiff Ecolab Inc.'s Motion for Leave to File its Second Amended Complaint, filed Apr. 14, 2006.

FMC Corporation's opening Claim Construction Brief, filed Apr. 21, 2006.
Construction Brief by FMC Corporation, FMC Corporation *Scott M. Russell, PhD.*, filed Apr. 21, 2006.
Declaration by FMC Corporation Francis DiGiovanni disclosing Exhibits A-Q, filed Apr. 21, 2006 Exhibits A-E are attached and correspond to documents 63:2-7.
United States Department of Agriculture, Food Safety and Inspection Service, www.www.fsis,usda.gov/Fact_Sheets/Poultry_Preparation_Fact_Sheets/index.asp.asp, printed Apr. 18, 2006 (Exhibit J for Declaration by FMC Corporation Francis DiGiovanni, filed Apr. 21, 2006).
"Microbiological Decontamination of Food Animal Carcasses by Washing and Sanitizing Systems: A Review" by James S. Dickson and Maynard E. Anderson printed in the *Journal of Food Protection*, vol. 55, No. 2, pp. 133-140 (Feb. 1992) (Exhibit K for Declaration by FMC Corporation *Francis DiGiovanni*, filed Apr. 21, 2006).
*Principles of Food Sanitation* (1989) by Norman G. Mariott; cover, copyright and p. 377 with definition of "sanitize" (Exhibit L for Declaration by FMC Corporation Francis DiGiovanni, filed Apr. 21, 2006).
*Webster's Ninth New Collegiate Dictionary* (1991) cover; copyright and pp. 504, 736 and 1141 with definition's of "game", "meat", and "spray" (Exhibit M for Declaration by FMC Corporation Francis DiGiovanni, filed Apr. 21, 2006).
"The Effect of Hot Boning Broiler Meat Muscles on Postmortem pH Decline" by M.K. Stewart and D. L. Fletcher printed in *Poultry Science*, vol. 63, No. 9(1984) (Exhibit N for Declaration by FMC Corporation Francis DiGiovanni, filed Apr. 21, 2006).
"Manganese, Copper, Zinc, Iron, Cadmium, Mercury and Lead in Muscle Meat, Liver and Kidneys of Poultry, Rabbit and Sheep, Food Additives and Contaminants" by J. Falandysz printed in *Food Additives and Contaminants*, vol. 8, No. 1, p. 71-83 (1991) (Exhibit O for Declaration by FMC Corporation *Francis DiGiovanni*, filed Apr. 21, 2006).
United States Department of Agriculture, Food Safety and Inspection Service, www.www.fsis,usda.gov/Fact_Sheets/Farm_Raised_Game/index.asp.asp, printed Apr. 17, 2006 (Exhibit P for Declaration by FMC Corporation Francis DiGiovanni, filed Apr. 21, 2006).
Plaintiff Ecolab Inc.'s Opening Claim Construction Brief, filed Apr. 21, 2006.
Claim Construction Brief Filed by Ecolab, Inc., Declaration of Timothy A. Gutzmann, filed Apr. 21, 2006.
Claim Construction Brief filed by Ecolab Inc., Declaration of Rachel K. Zimmerman disclosing 22 Exhibits, filed Apr. 21, 2006 Exhibits 1-5 are attached and correspond to documents 71:2-6.
Response filed by Plaintiff Ecolab Inc. on Jul. 3, 1996 during prosecution of US 5,632,676 (Exhibit 8 for Claim Construction Brief filed by Ecolab Inc., Declaration of Rachel K. Zimmerman, filed Apr. 21, 2006).
FDA Food Code 1-201.10(69) (1993) (Exhibit 10 for Claim Construction Brief filed by Ecolab Inc., Declaration of Rachel K. Zimmerman, filed Apr. 21, 2006).
FDA Food Code 1-201.10 (71) (1995) (Exhibit 11 for Claim Construction Brief filed by Ecolab Inc., Declaration of Rachel K. Zimmerman, Apr. 21, 2006).
FDA Food Code 1-201.10 (70) (1997) (Exhibit 12 for Claim Construction Brief filed by Ecolab Inc., Declaration of Rachel K. Zimmerman, filed Apr. 21, 2006).
Block, *Disinfection, Sterilization and Preservation* 24 (5th ed. 2001) pp. 24-28 (Exhibit 13 for Claim Construction Brief filed by Ecolab Inc., Declaration of Rachel K. Zimmerman, filed Apr. 21, 2006).
Response filed by Plaintiff Ecolab Inc. on Oct. 6, 1994, during prosecution of US 5,632,676. (Exhibit 15 for Claim Construction Brief filed by Ecolab Inc., Declaration of Rachel K. Zimmerman, filed Apr. 21, 2006).
IDS filed by Plaintiff on Jan. 12, 1994, during prosecution of US 5,632,676. (Exhibit 17 for Claim Construction Brief filed by Ecolab Inc., Declaration of Rachel K. Zimmerman, filed Apr. 21, 2006).
United States Department of Agriculture, Food Safety and Inspection Service, www.fsis,usda.gov/HELP/glossary-m/index.asp, printed Apr. 21, 2006 (Exhibit 22 for Claim Construction Brief filed by Ecolab Inc., Declaration of Rachel K. Zimmerman, filed Apr. 21, 2006).

FMC Corporation's Opening Claim Construction Brief, filed Apr. 26, 2006.

FMC's Memorandum of Law in Opposition to Ecolab Inc.'s Motion for Leave to File its Second Amended Complaint, filed May 3, 2006.

Declaration of Francis DiGiovanni Submitted in Support of FMC's Memorandum of Law in Opposition to Ecolab Inc.'s Motion for Leave to File its Second Amended Complaint, filed May 3, 2006.

Memorandum in Opposition re Motion to Amend/Correct Notice (Other) *Leave to File its Amended Answer, Affirmative Defenses, and Counterclaim* filed by Ecolab, Inc, filed May 5, 2006.

Declaration of Rachel Zimmerman in Opposition to Memorandum in Opposition to Motion filed by Ecolab, Inc., filed May 5, 2006.

Plaintiff Ecolab Inc.'s Supplemental Answer to FMC's Interrogatory No. 2 and Second Supplemental answer to FMC's Interrogatory No. 14. Ecolab's supplemental answer to FMC's Interrogatory No. 2 begins on p. 31—(Exhibit 1 for Declaration of Rachel Zimmerman in Opposition to Memorandum in Opposition to Motion filed by Ecolab, Inc., filed May 5, 2006).

An excerpt from the Apr. 6, 2006, Deposition Testimony of Timothy Gutzmann—(Exhibit 4 for Declaration of Rachel Zimmerman in Opposition to Memorandum in Opposition to Motion filed by Ecolab, Inc., filed May 5, 2006).

Response re Claim Construction Brief *Plaintiff Ecolab Inc.'s Answering Claim Construction Brief* filed by Ecolab, Inc., filed May 10, 2006.

Declaration of Martin P. Rigney in Support of Response filed by Ecolab, Inc. filed May 10, 2006.

Declaration of R. Bruce Tompkin in Support of Response filed by Ecolab Inc., filed May 10, 2006.

Declaration of Rachel K. Zimmerman in Support of Response filed by Ecolab Inc., filed May 10, 2006.

An Office Action mailed Mar. 3, 1995 during the prosecution of the '676 patent—(Exhibit A for Declaration of Rachel K. Zimmerman in Support of Response filed by Ecolab Inc., filed May 10, 2006).

Merriam Webster's Collegiate Dictionary p. 1138 (10th ed. 1997)—(Exhibit D for Declaration of Rachel K. Zimmerman in Support of Response filed by Ecolab Inc., filed May 10, 2006).

Response re Claim Construction Brief filed by FMC Corporation, filed May 10, 2006.

Second Declaration re Response by FMC Corporation of Scott M. Russel Ph.D., filed May 10, 2006. Exhibits 1-5 (100:2-6).

Deming, M. et al., "Campylobacter Enteritis at a University: Transmission from Eating Chicken and from Cats", American J. Epidemiology, v. 126 No. 3, pp. 526-537 (1987)—(Exhibit 1 for Second Declaration re Response by FMC Corporation of Scott M. Russel Ph.D., filed May 10, 2006).

Tauxe, R., Hargrett-Bean, N., Patton, M. et al., "Campylobacter Isolates in the United States, 1982-1986", CDC MMWR Surveillance Summaries 37 (SS-2), 1-13 (Jun. 1, 1988)—(Exhibit 2 for Second Declaration re Response by FMC Corporation of Scott M. Russel Ph.D., filed May 10, 2006).

DeWit et al., "Cross-contamination during the preparation of frozen chickens in the kitchen", J. Hygiene, 83(1): 37-32 (Aug. 1979)—(Exhibit 3 for Second Declaration re Response by FMC Corporation of Scott M. Russel Ph.D., filed May 10, 2006).

Hopkins, R. and Scott, A., "Handling Raw Chicken as a Source for Sporadic Campylobacter Infections", Letter, J. Infectious Diseases, vol. 148 No. 4, 770 (Oct. 1983)—(Exhibit 4 for Second Declaration re Response by FMC Corporation of Scott M. Russel Ph.D., filed May 10, 2006).

Kapperud et al., "Risk Factors for Sporadic Campylobacter Infections", J. Clinical Microbiology, vol. 30, No. 12, pp. 3117-3121 (Dec. 1992)—(Exhibit 5 for Second Declaration re Response by FMC Corporation of Scott M. Russel Ph.D., filed May 10, 2006).

Second Declaration re Response by FMC Corporation of Francis DiGiovanni, filed May 10, 2006. Exhibits A-E (101:2-6).

Bronsteing, S., "A Journal-Constitution Special Report: Chicken: How Safe? First of Two Parts," Atlanta Journal of Constitution (May 26, 1991)—(Exhibit A for Second Declaration re Response by FMC Corporation of Francis DiGiovanni, filed May 10, 2006).

Snow, J., "Cook Food Well to Avoid Illness . . . ," Akron Beacon-Journal (Apr. 14, 1993)—(Exhibit B for Second Declaration re Response by FMC Corporation of Francis DiGiovanni, filed May 10, 2006).

Lisa Y. Lefferts and Stephen Schmidt, Name your poison—food—includes information about microbial resistance to antibiotics, Nutrition Action Health Letter, Jul.-Aug. 1991—(Exhibit C for Second Declaration re Response by FMC Corporation of Francis DiGiovanni, filed May 10, 2006).

United States Department of Agriculture, Food Safety and Inspection Service, www.fsis.usda.gov/OA/pubs/grndpoul.htm "The Facts About Ground Poultry" printed May 10, 2006—(Exhibit D for Second Declaration re Response by FMC Corporation of Francis DiGiovanni, filed May 10, 2006).

United States Department of Agriculture, Food Safety and Inspection Service, "Report of the U.S. Delegate, 27th Session, Codex Committee on Fish and Fishery Products, Cape Town South Africa, Feb. 28-Mar. 4, 2005", www.fsis.usda.gov/regulations_&_policies/Delegate_Report_27CCFFP/index.asp printed May 10, 2006—(Exhibit E for Second Declaration re Response by FMC Corporation of Francis DiGiovanni, filed May 10, 2006).

Preliminary Claim Construction signed by Judge James. M. Rosenbaum, filed May 11, 2006.

Order Granting in part and denying in part Motion to Amend/Correct—graining in part and denying in part Motion for Leave to File, filed May 19, 2006.

Letter to Magistrate Judge by FMC Corporation seeking clarification regarding the second paragraph of the May 19, 2006 Order relating to FMC's motion for leave to amend the pleadings, filed May 30, 2006.

Objection regarding 104 Order, Ecolab Inc's Response to the Court's Preliminary Claim Construction filed by Ecolab, Inc. filed Jun. 1, 2006 (Sealed Document).

Declaration of Rachel K. Zimmerman in Support of 113 Objection filed by Ecolab, Inc, filed Jun. 1, 2006 (Sealed Document).

Response regarding Order, to the Court's Preliminary Claim Construction filed by FMC Corporation, filed Jun. 1, 2006.

Exhibit regarding 114 Declaration in Support, 113 Objection (Exhibit A) by Ecolab, Inc. filed by Ecolab, Inc., filed Jun. 1, 2006.

Certificate of Service by Ecolab, Inc. regarding 114 Declaration in Support, 118 Exhibit, 113 Objection, 117 LR7.1 Word Count Compliance Certificate on all parties, filed Jun. 1, 2006.

Appeal of Magistrate Judge Decision to District Court regarding 110 Order on Motion to Amend/Correct, Order on Motion for Leave to File, filed Jun. 5, 2006.

Letter to Magistrate Judge by Ecolab, Inc., Ecolab, Inc. Responding to FMC's Letter of May 30, 2006. (Attachments: #1 Exhibit(s) A—subpoena to Guthery #2 Exhibit(s) B—Complaint #3 Exhibit(s) C—Stipulation for Consent Judgment), filed Jun. 6, 2006.

Amended Order—Granting in Part and Denying in Part regarding 41 Motion to Amend/Correct Answer and Conterclaim filed by FMC Corporation, Signed by Magistrate Judge Franklin L Noel on Jun. 9, 2006, filed Jun. 9, 2006.

Amended Complaint (Second) against FMC Corporation, filed by Ecolab, Inc. (Attachments: #1 Certificate of Service), filed Jun. 9, 2006.

Stipulation to Amend Pretrial Schedule (Third) by Ecolab, Inc., FMC Corporation, filed Jun. 13, 2006.

Letter to District Judge by FMC Corporation *regarding (FMC's Provisional Objections to the Magistrate Judge's Order dated May 18, 2006*), filed Jun. 14, 2006.

Order—Granting re 129 Stipulation to Amend Pretrial Schedule . Signed by Magistrate Judge Franklin L Noel on Jun. 14, 2006, filed Jun. 14, 2006.

Answer to Amended Complaint (*Second*), *Affirmative Defenses*, Counterclaim against Ecolab, Inc. by FMC Corporation. (DiGiovanni, Francis) (filed: Jun. 23, 2006).

Memorandum in Support re 135 Motion to Compel filed by Ecolab, Inc., (Zimmerman, Rachel) (filed: Jul. 14, 2006).

Declaration of Todd S. Werner in Support of 135 Motion to Compel filed by Ecolab, Inc.. Received Sealed Documents on Jul. 14, 2006 Modified on Jul. 14, 2006 (GJS). (filed: Jul. 14, 2006).

Declaration of Rachel K. Zimmerman in Support of 141 Motion for Extension of Time to Complete Discovery filed by Ecolab, Inc., (Zimmerman, Rachel) (filed: Aug. 1, 2006).
Amended Third Notice of Videotaped Deposition of FMC Corporation and Request for Designation of Persons to Testify Pursuant to FED.R.CIV.30(b)(6), filed Aug. 1, 2006.
Memorandum in Opposition re 135 Motion to Compel filed by FMC Corporation. (DiGiovanni, Francis) (filed: Aug. 3, 2006).
Memorandum in Support re 152 Motion for Protective Order and for Sanctions filed by Ecolab, Inc.. (Williams, Douglas) (filed: Aug. 9, 2006).
Declaration of Douglas J. Williams in Support of 152 Motion for Protective Order and for Sanctions filed by Ecolab, Inc.. (Williams, Douglas) (filed: Aug. 9, 2006).
Declaration of Francis DiGiovanni, Esq. in Support of 164 Memorandum in Support of Motion filed by FMC Corporation. Modified text on Aug. 16, 2006 (gjs). (filed: Aug. 14, 2006).
Exhibit A: *B. Bugene Guthery, M.D.* (Plaintiff) vs. *Ecolab, Inc.* (Defendant), Plaintiff's Original Complaint and Application for Injunctive Relief Jury Trial Demanded, filed Aug. 14, 2004.
Exhibit B: *B. Bugene Guthery, M.D.* (Plaintiff) vs. *Ecolab, Inc.* (Defendant), Stipulation For Entry of Consent Judgement and Order for Judgement, filed Aug. 14, 2004.
Memorandum in Opposition re 162 Motion for Sanctions *and an Order Allowing FMC to Re-Notice and Take the Deposition of* B. Eugene Guthery filed by Ecolab, Inc. (Williams, Douglas) (filed: Aug. 21, 2006).
Memorandum in Opposition re 152 Motion for Protective Order *and for Sanctions* filed by FMC Corporation.(Wahlgren, Sharna) (Entered: Aug. 21, 2006).
Declaration of Rachel K. Zimmerman in Opposition to 162 Motion for Sanctions *and an Order Allowing FMC to Re-Notice and Take the Deposition of* B. Eugene Guthery filed by Ecolab, Inc.. (Williams, Douglas) Sealed Documents Received in Clerk's Office on Aug. 21, 2006. (KT) (Entered: Aug. 21, 2006).
"Emery® Fatty and Dibasic Acids Specifications and Characteristics", *Emery Industries*, Bulletin 145, (Oct. 1983).
Abstract: "Indirect food additives: adjuvants, production aids, and sanitizers", *Fed. Register*, 61(108), 28051-28053, 1 pg. (Jun. 4, 1996).
Armak Chemicals, "NEO-FAT Fatty Acids", *Akzo Chemicals Inc.*, Bulletin No. 86-17 (1986).
Baldry et al., "Disinfection of Sewage Effluent with Peracetic Acid," *Wat. Sci. Tech.*, vol. 21, No. 3 (1989) pp. 203-206.
Baldry et al., "Disinfection with peroxygens," *Industrial Biocides*, edited by K.R. Payne, New York, John Wiley & Sons, pp. 91-116.
Baldry, M.G.C., "The bactericidal, fungicidal and sporicidal properties of hydrogen peroxide and peracetic acid," *Journal of Applied Bacteriology*, vol. 54 (1983) pp. 417-423.
Bayliss et al., "The Synergistic Killing of Spores of *Bacillus Subtilis* by Hyrdrogen Peroxide and Ultra-Violet Light Irradiation," *FEMS Microbiology Letters*, 5 (1979) pp. 331-333.
Bell, K. et al., "Reduction of foodborne micro-organisms on beef carcass tissue using acetic acid, sodium bicarbonate, and hydrogen peroxide spray washes", *Food Microbiology*, vol. 14, pp. 439-448 (1997).
Beuchat, Larry R., "Surface Disinfection of Raw Produce," *Dairy, Food and Environmental Sanitation*, vol. 12, No. 1 (Jan. 1992) pp. 6-9.
Block, Seymour S., "Peroxygen Compounds," *Disinfection, Sterilization, and Preservation, Fourth Edition*, Chapter 9 (1991) pp. 167-181.
Block, Seymour S., "Peroxygen Compounds," *Disinfection, Sterilization and Preservation, Fifth Edition*, Chapter 9 (2001) pp. 185-204.
Breen, P. et al., "Elimination of *Salmonella* Contamination from Poultry Tissues by Cetylpyridinium Chloride Solutions", *Journal of Food Protection*, 60(9):1019-1021 (1997).
Breen, P. et al., "Quaternary Ammonium Compounds Inhibit and Reduce the Attachment of Viable *Salmonella typhimurium* to Poultry Tissues", *Journal of Food Science*, 60(6):1191-1196 (1995).

Brown, G. Eldon, "Use of Xanthomonas-campestris pv-vesicatoria to Evaluate Surface Disinfectants for Canker Quarantine Treatment of Citrus Fruit," *Plant Disease* (Apr. 1987) pp. 319-323.
Computer search results—Level 1-5 patents (Mar. 1994).
Computer search results from Ecolab Information Center (Jun. 1998).
Internal Search Report dated Jun. 3, 2002.
International Search Report dated Jan. 30, 2002.
Internal Search Report dated Dec. 27, 2002.
Cords, B.R., "New Peroxyacetic Acid Sanitizer", *Proceedings*, Twenty-Third Convention, Institute of Brewing, Sydney Australia, pp. 165-169 (1995).
Dickens, J. et al., "Effects of Acetic Acid and Hydrogen Peroxide Application During Defeathering on the Microbiological Quality of Broiler Carcasses Prior to Evisceration", *Poultry Science*, 76:657-660 (1997).
Dickens, J. et al., " The Effect of Acetic Acid and Air Injection on Appearance, Moisture Pick-Up, Microbiological Quality, and *Salmonella* Incidence on Processed Poultry Carcasses", *Poultry Science*, 73:582-586 (1994).
Dickens, J. et al., "The Effect of an Acetic Acid Dip on Carcass Appearance, Microbiological Quality, and Cooked Breast Meat Texture and Flavor", *Poultry Science*, 73:576-581 (1994).
Dickens, J. et al., "The Effects of Extended Chilling Times with Acetic Acid on the Temperature and Microbiological Quality of Processed Poultry Carcasses", *Poultry Science*, 74:1044-1048 (1995).
Dickinson, J. et al., "Microbiological Decontamination of Food Animal Carcasses by Washing and Sanitizing Systems: A Review", *Journal of Food Protection*, 55(2):133-140 (Feb. 1992).
Eggensperger, H., "Disinfectants Based on Peracid-Splitting Compounds", *Zbl. Bakt. Hyg.*, I. Abt. Orig. B 168, pp. 517-524 (1979).
Focus on Interox, *Effluent + Water Treatment Journal* (Aug. 1979).
Fraser, J.A.L., "Novel applications of peracetic acid in industrial disinfection," *Specialty Chemicals*, vol. 7, No. 3 (1987) pp. 178, 180, 182 ,184, 186.
FSTA abstract, accession No. 1999(10):C1223, abstracting: Journal of Food Protection, vol. 62(7), pp. 761-765 (1999).
FSTA abstract, accession No. 2000(06):J1220, abstracting: Dairy, Food and Environmental Sanitation, vol. 19(12), pp. 842-847 (1999).
Greenspan et al., "The Application of Peracetic Acid Germicidal Washes to Mold Control of Tomatoes," *Food Technology*, vol. 5, No. 3 (Mar. 1951) pp. 95-97.
Han et al., "Destruction of Bacterial Spores on Solid Surfaces," *Journal of Food Processing and Preservation*, vol. 4, No. 1-2 (1980) pp. 95-110.
Heinemann, P.G., "The Germicidal Efficiency of Commercial Preparations of Hydrogen Peroxid," *The Journal of the American Medical Association*, vol. LX, No. 21 (1913) pp. 1603-1606.
*Patent Application*, U.S. Appl. No. 09/614,631, filed Jul. 12, 2000, Hilgren, J. et al.
Hutchings et al., "Comparative Evaluation of the Bactericidal Efficiency of Peracetic Acid, Quaternaries, and Chlorine-Containing Compounds," *Presented at the 49th General Meeting of the Society of American Bacteriologists*, (Abstract) (1949) pp. 50-51.
Interox Chemicals Ltd. product brochure entitled: OXYMASTER Peracetic Acid 12%.
Interox Chemicals Ltd. product brochure entitled: PROXITANE 4002 Peracetic Acid 36-40%.
Jager et al., "Peracetic acid as a disinfectant in breweries and soft drink factories," *Mitt. Versuch. Gaorung. Wien.*, vol. 34 (1980) pp. 32-36.
Kim, J. et al., "Cetylpyridinium Chloride (CPC) Treatment on Poultry Skin to Reduce Attached *Salmonella*", *Journal of Food Protection*, 59(3):322-326 (1995).
Kunzmann, T., "Investigations on the disinfecting action of hydrogen peroxides," *Fortschr. Med.*, vol. 52, No. 16 (1934) pp. 357-359.
Laska, M. et al., "Odor structure-activity relationships of carboxylic acids correspond between squirrel monkeys and humans", *Am. J. Physiol.*, 271:R1639-R1645 (1998).
Lillard, H., "Bacterial Cell Characteristics and Conditions Influencing their Adhesion to Poultry Skin", *Journal of Food Protection*, 48(9):803-807 (Sep. 1985).

Lillard, H., "Factors Affecting the Persistence of *Salmonella* During the Processing of Poultry", *Journal of Food Protection*, 52(11):829-832 (Nov. 1989).

Lion C. et al., "New decontaminants. Reaction of peroxyacid esters with toxic insecticides", *Bull. Soc. Chim. Belg.*, vol. 100, No. 7, pp. 555-559 (1991).

Merka, V. et al., "Disinfectant properties of some peroxide compounds.", Abstract No. 67542e, *Chemical Abstracts*, vol. 67 (1967).

MicroPatent Report dated Aug. 18, 2003.

Mulder, R.W.A.W. et al., "Research Note: *Salmonella* Decontamination of Broiler Carcasses with Lactic Acid, L-Cysteine, and Hdrogen Peroxide", *Poultry Science*, vol. 66, pp. 1555-1557 (1987).

Nambudripad et al., "Bactericidal Efficiency of Hydrogen Peroxide Part I. Influence of different concentrations on the rate and extent of destruction of some bacteria of dairy importance," *Indian Journal of Dairy Science*, 4, pp. 65-69.

Opinion Letter dated Apr. 11, 2000.

Orth et al., "Is the control of *Listeria, Campylobacter* and *Yersinia* a disinfection problem?", *Fleischwirtsch*, 69 (10) (1989) pp. 1575-1576.

Parker, W. et al., "Peroxides. IV. Aliphatic Diperacids", *Aliphatic Diperacids*, vol. 79, pp. 1929-1931 (Apr. 20, 1957).

Parker, W. et al., "Peroxides. II. Preparation, Characterization and Polarographic Behavior of Longchaing Aliphatic Peracids", *Synthesis and Properties of LongChain Aliphatic Peracids*, vol. 77, pp. 4037-4041 (Aug. 5, 1955).

Pfizer Chemical Division, "Pfizer Flocon® Biopolymers for Industrial Uses (xanthan broths)", Data Sheet 679, pp. 1-4 (year unknown).

Poffe et al., "Disinfection of Effluents from Municipal Sewage Treatment Plants with Peroxy Acids," *Zbl. Bakt. Hyg., I. Abt. Orig.* B 167 (1978) pp. 334-346.

Ranganna et al., "Chemical Preservatives and Antioxidants," *Indian Food Packer* (May-Jun. 1981) pp. 30-44.

Richardson, B.W., "On Peroxide of Hydrogen, or Ozone Water, as a Remedy," *The Lancet* (Mar. 1891) pp. 707-709, 760-763.

Search Reports for the use of amine oxides with hydrogen peroxide in bleaching, sanitizing, disinfectant or hard surface cleaners.

Search Result from Database WPI and Database INPADOC.

Search Results (2003).

Sims, Alan F.E., "Industrial effluent treatment with hydrogen peroxide," *Chemistry and Industry*, No. 14 (1983) pp. 555-558.

Solvay product brochure entitled: Oxymaster® —Proxitane® Peracetic Acid Applications.

Solvay product brochure entitled: Oxymaster® —Proxitane® Peracetic Acid Solutions; Handling, Storage and Transport Information (Safety Documentation).

Tamblyn, K. et al., "Bactericidal Activity of Organic Acids against *Salmonella typhimurium* Attached to Broiler Chicken Skin", *Journal of Food Protection*, 60(6):629-633 (1997).

Taylor, J.H. et al., "A comparison of the bactericidal efficacy of 18 disinfectants used in the food industry against *Escherichia coli* O 157:H7 . . . " *Journal of Applied Microbiology*, 87:718-725 (1999).

Towle, G. et al., "Industrial Gums polysaccharides and Their Derivatives", Second Edition, Ch. XIX, "Pectin", pp. 429-444 (year unknown).

Xiong, H. et al., "Spraying Chicken Skin with Selected Chemicals to Reduce Attached *Salmonella typhimurium*", *Journal of Food Protection*, 61(3):272-275 (1998).

Yoshpe et al., "Disinfection of Water by Hydrogen Peroxide," *Health Laboratory Science*, vol. 5, No. 4 (1968) pp. 233-238.

\* cited by examiner

MEDIUM CHAIN PEROXYCARBOXYLIC ACID COMPOSITIONS

CROSS REFERENCE TO RELATED APPLICATION

The present application claims priority as a continuation in part to U.S. patent application Ser. No. 10/754,426, filed Jan. 9, 2004, the disclosure of which is incorporated herein by reference.

FIELD OF THE INVENTION

The present invention relates to compositions including medium chain peroxycarboxylic acid, methods for making these compositions, and methods for reducing the population of a microorganism. The compositions can include advantageously high levels of the medium chain peroxycarboxylic acid, can be readily made, and/or can exhibit reduced odor.

BACKGROUND OF THE INVENTION

Conventional peroxycarboxylic acid compositions typically include short chain peroxycarboxylic acids or mixtures of short chain peroxycarboxylic acids and medium chain peroxycarboxylic acids (see, e.g., U.S. Pat. Nos. 5,200,189, 5,314,687, 5,409,713, 5,437,868, 5,489,434, 6,674,538, 6,010,729, 6,111,963, and 6,514,556). Typically, conventional mixed peroxycarboxylic acid compositions include large amounts of short chain carboxylic acid and only limited amounts of medium chain peroxycarboxylic acid relative to the corresponding medium chain peroxycarboxylic acid.

Ongoing research efforts have strived for improved peroxycarboxylic acid compositions. In particular, these efforts have strived for compositions that have increased levels of medium chain peroxycarboxylic acid, that can be readily made, or that have reduced odor compared to conventional compositions including short chain peroxycarboxylic and carboxylic acids.

SUMMARY OF THE INVENTION

The present invention relates to compositions including medium chain peroxycarboxylic acid, methods for making these compositions, and methods for reducing the population of a microorganism. In certain embodiments, the compositions can include advantageously high levels of the medium chain peroxycarboxylic acid, can be readily made, and/or can exhibit reduced odor.

In an embodiment, the present compositions can include medium chain peroxycarboxylic acid, medium chain carboxylic acid, carrier, and solubilizer. In certain embodiments, the present compositions include about 2 or more parts of medium chain peroxycarboxylic acid for each 7 parts of medium chain carboxylic acid; about 2 or more parts of medium chain peroxycarboxylic acid for each 5 parts of medium chain carboxylic acid; about 2 or more parts of medium chain peroxycarboxylic acid for each 4 parts of medium chain carboxylic acid; or about 2 parts of medium chain peroxycarboxylic acid for each 3 parts of medium chain carboxylic acid.

In an embodiment, the solubilizer includes solvent, surfactant, or mixture thereof. In an embodiment, the surfactant solubilizer includes a microemulsion forming surfactant, e.g., an anionic surfactant. In an embodiment, the composition includes a microemulsion. In an embodiment, the solubilizer includes polyalkylene oxide, capped polyalkylene oxide, nonionic surfactant, anionic surfactant, or mixture thereof. In an embodiment, the solvent solubilizer includes polyalkylene oxide, capped polyalkylene oxide, nonionic surfactant, or mixture thereof.

In an embodiment, the present compositions include no, only insignificant, or relatively small amounts of short chain peroxycarboxylic acid, short chain carboxylic acid, or mixture thereof. For example, in an embodiment, the composition can be substantially free of added short chain carboxylic acid, short chain peroxycarboxylic acid, or mixture thereof. For example, in an embodiment, the composition can include short chain carboxylic acid, short chain peroxycarboxylic acid, or mixture thereof at a level insufficient to solubilize medium chain peroxycarboxylic acid. For example, in an embodiment, the composition can include short chain carboxylic acid, short chain peroxycarboxylic acid, or mixture thereof at a level insufficient to cause objectionable odor. For example, in an embodiment, the composition can include about 1 or more parts of medium chain peroxycarboxylic acid for each 8 parts of short chain carboxylic acid, short chain peroxycarboxylic acid, or mixture thereof.

In an embodiment, the composition also includes oxidizing agent, inorganic acid, stabilizing agent, another adjuvant or additive, or mixture thereof.

In an embodiment, the present invention includes a method of making a medium chain peroxycarboxylic acid composition. The method can include reacting medium chain carboxylic acid and oxidizing agent in the presence of carrier, solubilizer, acidulant, stabilizing agent, or mixture thereof. The method can form advantageously high levels of medium chain peroxycarboxylic acids in advantageously short times. For example, in an embodiment, the present method includes converting 20% or more of the medium chain carboxylic acid to medium chain peroxycarboxylic acid in about 24 or fewer hours. For example, in an embodiment, the present method includes converting about 25% or more of the medium chain carboxylic acid to medium chain peroxycarboxylic acid in about 24 or fewer hours. For example, in an embodiment, the present method includes converting about 30% or more of the medium chain carboxylic acid to medium chain peroxycarboxylic acid in about 24 or fewer hours. For example, in an embodiment, the present method includes converting about 35% or more of the medium chain carboxylic acid to medium chain peroxycarboxylic acid in about 24 or fewer hours. For example, in an embodiment, the present method includes converting about 40% of the medium chain carboxylic acid to medium chain peroxycarboxylic acid in about 24 or fewer hours.

In an embodiment, the present invention includes a method of using a medium chain peroxycarboxylic acid composition. The method can include contacting an object with the present composition (e.g., a use composition) and can result in reducing the population of one or more microorganisms on the object.

DETAILED DESCRIPTION OF THE INVENTION

Definitions

Figure 1:
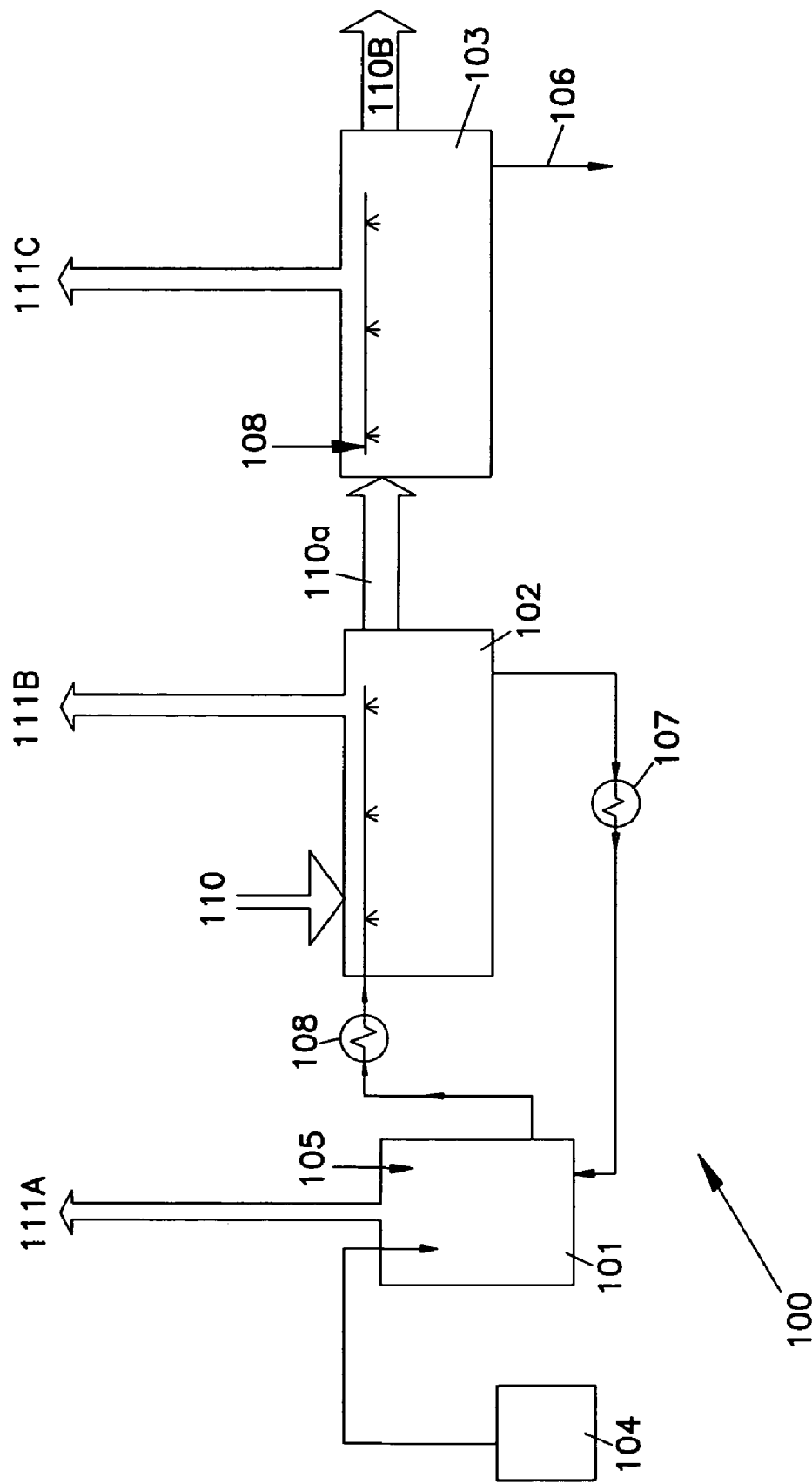
FIG. 1 is a diagram of a beverage plant, including a cold aseptic filling plant, in which either carbonated or non-carbonated beverages can be prepared and bottled.

As used herein, the phrase "medium chain carboxylic acid" refers to a carboxylic acid that: 1) has reduced or is lacking odor compared to the bad, pungent, or acrid odor associated with an equal concentration of small chain carboxylic acid, and 2) has a critical micellar concentration greater than 1 mM in aqueous buffers at neutral pH. Medium chain carboxylic acids exclude carboxylic acids that are infinitely soluble in or miscible with water at 20° C. Medium chain carboxylic acids include carboxylic acids with boiling points (at 760 mm Hg pressure) of 180 to 300° C. In an embodiment, medium chain carboxylic acids include carboxylic acids with boiling points (at 760 mm Hg pressure) of 200 to 300° C. In an embodiment, medium chain carboxylic acids include those with solubility in water of less than 1 g/L at 25° C. Examples of medium chain carboxylic acids include pentanoic acid, hexanoic acid, heptanoic acid, octanoic acid, nonanoic acid, decanoic acid, undecanoic acid, and dodecanoic acid.

As used herein, the phrase "medium chain peroxycarboxylic acid" refers to the peroxycarboxylic acid form of a medium chain carboxylic acid.

As used herein, the phrase "short chain carboxylic acid" refers to a carboxylic acid that: 1) has characteristic bad, pungent, or acrid odor, and 2) is infinitely soluble in or miscible with water at 20° C. Examples of short chain carboxylic acids include formic acid, acetic acid, propionic acid, and butyric acid.

As used herein, the phrase "short chain peroxycarboxylic acid" refers to the peroxycarboxylic acid form of a short chain carboxylic acid.

As used herein, the term "solubilizer" refers to a component of the present compositions to that makes soluble or increases the solubility in a carrier (e.g., water) of the medium chain carboxylic acid, medium chain peroxycarboxylic acid, or mixture thereof. For example, in an embodiment, the solubilizer can keep a composition including medium chain carboxylic acid, medium chain peroxycarboxylic acid, or mixture thereof in solution or can keep the composition finely and evenly dispersed under ordinary storage conditions without forming a separate layer. The solubilizer can, for example, solubilize a medium chain carboxylic acid to an extent sufficient to allow it to react with an oxidizing agent, such as hydrogen peroxide. A solubilizer can be identified by a test that measures phase separation under ordinary storage conditions, such as room temperature, 100° F., or 60° C. As used herein, the term "solubilizer" does not include short chain carboxylic acids.

As used herein, the term "microemulsion" refers to a thermodynamically stable dispersion of one liquid phase into another stabilized by an interfacial film of surfactant. The dispersion can be oil-in-water or water-in-oil. Microemulsions are typically clear solutions when the droplet diameter is approximately 100 nanometers or less. In an embodiment, the present microemulsion composition is a shear thinning viscoelastic gel or liquid that has a blue tyndall appearance.

As used herein, the phrases "blue tyndall appearance" or "blue tyndall" refer to a bluish hue due to scattering of blue light or the blue region of the light spectrum.

As used herein, the phrases "viscoelastic gel" and "viscoelastic liquid" refer to a liquid composition that exhibits both viscous and elastic characteristics or responses, which is indicative of long range order or structure.

As used herein, a composition or combination "consisting essentially" of certain ingredients refers to a composition including those ingredients and lacking any ingredient that materially affects the basic and novel characteristics of the composition or method. The phrase "consisting essentially of" excludes from the claimed compositions and methods short chain carboxylic acids, short chain peroxycarboxylic acids, or mixtures thereof, unless such an ingredient is specifically listed after the phrase.

As used herein, a composition or combination "substantially free of" one or more ingredients refers to a composition that includes none of that ingredient or that includes only trace or incidental amounts of that ingredient. Trace or incidental amounts can include the amount of the ingredient found in another ingredient as an impurity or that is generated in a minor side reaction during formation or degradation of the medium chain peroxycarboxylic acid.

As used herein, the phrase "a level insufficient to solubilize" refers to a concentration of an ingredient at which the ingredient is not sufficient to solubilize an insoluble material and to keep the composition substantially in one phase.

As used herein, the phrases "objectionable odor", "offensive odor", or "malodor" refer to a sharp, pungent, or acrid odor or atmospheric environment from which a typical person withdraws if they are able to. Hedonic tone provides a measure of the degree to which an odor is pleasant or unpleasant. An "objectionable odor", "offensive odor", or "malodor" has an hedonic tone rating it as unpleasant as or more unpleasant than a solution of 5 wt-% acetic acid, propionic acid, butyric acid, or mixtures thereof.

As used herein, the term "microorganism" refers to any noncellular or unicellular (including colonial) organism. Microorganisms include all prokaryotes. Microorganisms include bacteria (including cyanobacteria), lichens, fungi, protozoa, virinos, viroids, viruses, phages, and some algae. As used herein, the term "microbe" is synonymous with microorganism.

As used herein, the term "object" refers to a something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors. Objects also include the body or part of the body of a living creature, e.g., a hand.

As used herein, the phrase "food product" includes any food substance that might require treatment with an antimicrobial agent or composition and that is edible with or without further preparation. Food products include meat (e.g. red meat and pork), seafood, poultry, fruits and vegetables, eggs, living eggs, egg products, ready to eat food, wheat, seeds, roots, tubers, leafs, stems, corms, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the phrase "plant product" includes any plant substance or plant-derived substance that might require treatment with an antimicrobial agent or composition. Plant products include seeds, nuts, nut meats, cut flowers, plants or crops grown or stored in a greenhouse, house plants, and the like. Plant products include many animal feeds.

As used herein, a processed fruit or vegetable refers to a fruit or vegetable that has been cut, chopped, sliced, peeled, ground, milled, irradiated, frozen, cooked (e.g., blanched, pasteurized), or homogenized. As used herein a fruit or vegetable that has been washed, colored, waxed, hydro-cooled, refrigerated, shelled, or had leaves, stems or husks removed is not processed.

As used herein, the phrase "meat product" refers to all forms of animal flesh, including the carcass, muscle, fat, organs, skin, bones and body fluids and like components that form the animal. Animal flesh includes the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "poultry debris" refers to any debris, residue, material, dirt, offal, poultry part, poultry waste, poultry viscera, poultry organ, fragments or combinations of such materials, and the like removed from a poultry carcass or portion during processing and that enters a waste stream.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "air streams" includes food anti-spoilage air circulation systems. Air streams also include air streams typically encountered in hospital, surgical, infirmity, birthing, mortuary, and clinical diagnosis rooms.

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and handwash dip-pans, third-sink rinse waters, and the like. Waters also include domestic and recreational waters such as pools, spas, recreational flumes and water slides, fountains, and the like.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or fabric surfaces, e.g., knit, woven, and non-woven surfaces (such as surgical garments, draperies, bed linens, bandages, etc.,), or patient-care equipment (such as respirators, diagnostic equipment, shunts, body scopes, wheel chairs, beds, etc.,), or surgical and diagnostic equipment. Health care surfaces include articles and surfaces employed in animal health care.

As used herein, the term "instrument" refers to the various medical or dental instruments or devices that can benefit from cleaning with a stabilized composition according to the present invention.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, "residential" or "institutional" objects or surfaces include those found in structures inhabited by humans. Such objects or surfaces include bathroom surfaces, drains, drain surfaces, kitchen surfaces, and the like.

As used herein, the phrase "densified fluid" refers to a fluid in a critical, subcritical, near critical, or supercritical state. The fluid is generally a gas at standard conditions of one atmosphere pressure and 0° C. As used herein, the phrase "supercritical fluid" refers to a dense gas that is maintained above its critical temperature, the temperature above which it cannot be liquefied by pressure. Supercritical fluids are typically less viscous and diffuse more readily than liquids. In an embodiment, a densified fluid is at, above, or slightly below its critical point. As used herein, the phrase "critical point" is the transition point at which the liquid and gaseous states of a substance merge into each other and represents the combination of the critical temperature and critical pressure for a substance. The critical pressure is a pressure just sufficient to cause the appearance of two phases at the critical temperature. Critical temperatures and pressures have been reported for numerous organic and inorganic compounds and several elements.

As used herein, the terms "near critical" fluid or "subcritical" fluid refer to a fluid material that is typically below the critical temperature of a supercritical fluid, but remains in a fluid state and denser than a typical gas due to the effects of pressure on the fluid. In an embodiment, a subcritical or near critical fluid is at a temperature and/or pressure just below its critical point. For example, a subcritical or near critical fluid can be below its critical temperature but above its critical pressure, below its critical pressure but above its critical temperature, or below both its critical temperature and pressure. The terms near critical and subcritical do not refer to materials in their ordinary gaseous or liquid state.

As used herein, weight percent (wt-%), percent by weight, % by weight, and the like are synonyms that refer to the concentration of a substance as the weight of that substance divided by the weight of the composition and multiplied by 100. Unless otherwise specified, the quantity of an ingredient refers to the quantity of active ingredient.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid and peroxyoctanoic acid.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2).

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

Medium Chain Peroxycarboxylic Acid Antimicrobial Compositions

The present invention includes medium chain peroxycarboxylic acid compositions. The present medium chain peroxycarboxylic acid compositions can include increased levels of medium chain peroxycarboxylic acid compared to conventional peroxycarboxylic acid compositions. The inventive compositions can include medium chain peroxycarboxylic acid and a solubilizer. The solubilizer can increase or maintain the solubility of the medium chain peroxycarboxylic acid. The present medium chain peroxycarboxylic acid compositions can include a microemulsion or a surfactant that can form a microemulsion. The present medium chain peroxycarboxylic acid compositions need not include substantial amounts of short chain carboxylic acid, short chain peroxycarboxylic acid, or mixture thereof. It is believed that, in conventional mixed peroxycarboxylic acid compositions, the short chain carboxylic acid, short chain peroxycarboxylic acid, or mixture thereof can solubilize medium chain peroxycarboxylic acid.

In an embodiment, the present compositions include medium chain peroxycarboxylic acid. These compositions can also include medium chain carboxylic acid. Such compositions can include advantageously high levels of medium chain peroxycarboxylic acid. In an embodiment, the present compositions include about 2 or more parts by weight of medium chain peroxycarboxylic acid for each 7 parts by weight of medium chain carboxylic acid. In an embodiment, the present compositions include about 2 or more parts by weight of medium chain peroxycarboxylic acid for each 6 parts by weight of medium chain carboxylic acid. In an embodiment, the present compositions include about 2 or more parts by weight of medium chain peroxycarboxylic acid for each 5 parts by weight of medium chain carboxylic acid. In an embodiment, the present compositions include about 2 or more parts by weight of medium chain peroxycarboxylic acid for each 4 parts by weight of medium chain carboxylic acid. In an embodiment, the present compositions include about 2 parts by weight of medium chain peroxycarboxylic acid for each 3 parts by weight of medium chain carboxylic acid.

In an embodiment, the present compositions include medium chain peroxycarboxylic acid and solubilizer. The solubilizer can include a solvent, a surfactant, or a mixture thereof. Suitable solvents include any of a variety of solvents that solubilize and do not significantly degrade the medium chain peroxycarboxylic acid. In certain embodiments, suitable solvents include polyalkylene oxide, capped polyalkylene oxide, mixtures thereof, or the like. Suitable solvents include nonionic surfactant, such as alkoxylated surfactant. Suitable alkoxylated surfactants include, for example, EO/PO copolymer, capped EO/PO copolymer, alcohol alkoxylate, capped alcohol alkoxylate, mixtures thereof, or the like. When employed as a solvent a surfactant, such as a nonionic surfactant, can be at concentrations higher than those conventionally employed.

The solubilizer can include surfactant (e.g., microemulsion forming surfactant). Suitable surfactants include anionic surfactant, nonionic surfactant, cationic surfactant, amphoteric surfactant, zwitterionic surfactant, mixtures thereof, or the like. The solubilizer can include a microemulsion forming surfactant. Suitable microemulsion forming surfactants include anionic surfactant, cationic surfactant, amphoteric surfactant, zwitterionic surfactant, mixtures thereof, or the like. Suitable microemulsion forming surfactants include anionic surfactants, such as sulfate surfactant, sulfonate surfactant, phosphate surfactant (phosphate ester surfactant), and carboxylate surfactant, mixtures thereof, or the like.

In an embodiment, the present composition need not include substantial amounts of short chain peroxycarboxylic acid. For example, the present compositions can be free of added short chain peroxycarboxylic acid. As used herein, free of added material refers to a composition that includes the material only as a incidental or trace quantity found, for example, as an ingredient of or impurity in another named ingredient or incidentally generated from a minor side reaction.

In an embodiment, the present composition includes only relatively small amounts of short chain peroxycarboxylic acid. For example, the present composition can include about 1 or more parts of medium chain peroxycarboxylic acid for each 8 parts of short chain carboxylic acid, short chain peroxycarboxylic acid, or mixture thereof. For example, the present composition can include short chain peroxycarboxylic acid at a level insufficient to cause odor offensive to a typical person.

In certain embodiments, the present composition does not include substantial amounts of peroxyacetic acid, is free of added peroxyacetic acid, includes about 1 or more parts of medium chain peroxycarboxylic acid for each 8 parts of peroxyacetic acid, or includes peroxyacetic acid at a level insufficient to cause odor offensive to a typical person.

In an embodiment, the present composition need not include substantial amounts of short chain carboxylic acid. For example, the present compositions can be free of added short chain carboxylic acid. In an embodiment, the present composition includes only relatively small amounts of short chain carboxylic acid. By way of further example, the present composition can include about 1 or more parts of medium chain peroxycarboxylic acid for each 8 parts of short chain carboxylic acid. For example, the present composition can include short chain carboxylic acid at a level insufficient to cause odor offensive to a typical person.

In certain embodiments, the present composition does not include substantial amounts of acetic acid, is free of added acetic acid, includes about 1 or more parts of medium chain peroxycarboxylic acid for each 8 parts of acetic acid, or includes acetic acid at a level insufficient to cause odor offensive to a typical person. In certain embodiments, the present compositions include, for example, less than 10 wt-%, less than less than 5 wt-%, less than 2 wt-%, or less than 1 wt-% acetic acid. In certain embodiments, the present use compositions include, for example, less than 40 ppm, less than 20 ppm, less than 10 ppm, or less than 5 ppm acetic acid.

In an embodiment, the present composition need not include substantial amounts of short chain peroxycarboxylic acid, short chain carboxylic acid, or mixture thereof. For example, the present compositions can be free of added short chain peroxycarboxylic acid, short chain carboxylic acid, or mixture thereof. For example, the present composition can include short chain carboxylic acid, short chain peroxycarboxylic acid, or mixture thereof at a level insufficient to cause odor offensive to a typical person. In certain embodiments, the present composition does not include substantial amounts of acetic acid, peroxyacetic acid, or mixtures thereof; is free of added acetic acid, peroxyacetic acid, or mixtures thereof; includes about 1 or more parts of medium chain peroxycarboxylic acid for each 8 parts of acetic acid, peroxyacetic acid, or mixtures thereof; or includes acetic acid, peroxyacetic acid, or mixtures thereof at a level insufficient to cause odor offensive to a typical person.

In an embodiment, the present composition includes about 1 or more parts of medium chain peroxycarboxylic acid for each 8 parts of short chain carboxylic acid, short chain peroxycarboxylic acid, or mixture thereof. In an embodiment, the present composition includes about 1 or more parts of medium chain peroxycarboxylic acid for each 7 parts of short chain carboxylic acid, short chain peroxycarboxylic acid, or mixture thereof. In an embodiment, the present composition includes about 1 or more parts of medium chain peroxycarboxylic acid for each 6 parts of short chain carboxylic acid, short chain peroxycarboxylic acid, or mixture thereof. In an embodiment, the present composition includes about 1 or more parts of medium chain peroxycarboxylic acid for each 5 parts of short chain carboxylic acid, short chain peroxycarboxylic acid, or mixture thereof. In an embodiment, the present composition includes about 1 or more parts of medium chain peroxycarboxylic acid for each 4 parts of short chain carboxylic acid, short chain peroxycarboxylic acid, or mixture thereof. In an embodiment, the present composition includes about 1 or more parts of medium chain peroxycarboxylic acid for each 3 parts of short chain carboxylic acid, short chain peroxycarboxylic acid, or mixture thereof. In an embodiment, the present composition includes about 1 or more parts of medium chain peroxycarboxylic acid for each 2 parts of short chain carboxylic acid, short chain peroxycarboxylic acid, or mixture thereof. In an embodiment, the present composition includes about 1 or more parts of medium chain peroxycarboxylic acid for each 1 part of short chain carboxylic acid, short chain peroxycarboxylic acid, or mixture thereof.

In an embodiment, the present composition has an odor less unpleasant than (e.g., as measured by an hedonic tone rating) than 5, 4, 3, 2, or 1 wt-% acetic acid in water. In an embodiment, the present composition has an odor less unpleasant than (e.g., as measured by an hedonic tone rating) than 5 wt-% acetic acid in water. In an embodiment, the present composition has an odor less unpleasant than (e.g., as measured by an hedonic tone rating) than 4 wt-% acetic acid in water. In an embodiment, the present composition has an odor less unpleasant than (e.g., as measured by an hedonic tone rating) than 3 wt-% acetic acid in water. In an embodiment, the present composition has an odor less unpleasant than (e.g., as measured by an hedonic tone rating) than 2 wt-% acetic acid in water. In an embodiment, the present composition has an odor with an odor less unpleasant than (e.g., as measured by an hedonic tone rating) than 1 wt-% acetic acid in water.

In certain embodiments, the present composition includes one or more (e.g., at least one) of oxidizing agent, acidulant, stabilizing agent, mixtures thereof, or the like. The present composition can include any of a variety of oxidizing agents, for example, hydrogen peroxide. The oxidizing agent can be effective to convert a medium chain carboxylic acid to a medium chain peroxycarboxylic acid. The oxidizing agent can also have antimicrobial activity, although it may not be present at a concentration sufficient to exhibit such activity. The present composition can include any of a variety of acidulants, for example, an inorganic acid. The acidulant can be effective to bring the pH of the present concentrate composition to less than 1, or to bring the pH of the present use composition to about 5 or below, about 4 or below, or about 3 or below. The acidulant can augment the antimicrobial activity of the present composition. The present composition can include any of a variety of stabilizing agents, for example, sequestrant, for example, phosphonate sequestrant. The sequestrant can be effective to stabilize the peroxycarboxylic acid.

In an embodiment, the present composition exhibits advantageous stability of the peroxycarboxylic acid. It is believed that in approximately one year at ambient conditions or room temperature (or 1 week at 60° C.) the amount of peroxycarboxylic acid in the compositions can be about 80% or more, about 85% or more, about 90% or more, or about 95% or more of the initial values or use composition levels. Such aged compositions are included in the scope of the present invention.

In an embodiment, the present composition exhibits advantageous efficacy compared to other antimicrobial compositions at the same level of active. In certain embodiments, the present composition has reduced or no volatile organic compounds compared to conventional peroxycarboxylic acid compositions. In an embodiment, the present composition has a higher flash point compared to conventional peroxycarboxylic acid compositions. In an embodiment, the present composition exhibits improved operator or user safety compared to conventional peroxycarboxylic acid compositions. In an embodiment, the present composition exhibits improved storage or transportation safety compared to conventional peroxycarboxylic acid compositions.

In certain embodiments, the present composition includes about 0.0005 to about 5 wt-% medium chain peroxycarboxylic acid, about 0.3 to about 7 wt-% medium chain peroxycarboxylic acid, about 0.5 to about 5 wt-% medium chain peroxycarboxylic acid, about 0.5 to about 4 wt-% medium chain peroxycarboxylic acid, about 0.8 to about 3 wt-% medium chain peroxycarboxylic acid, about 1 to about 3 wt-% medium chain peroxycarboxylic acid, or about 1 to about 2 wt-% medium chain peroxycarboxylic acid. The composition can include any of these ranges or amounts not modified by about.

In certain embodiments, the present composition includes about 0.001 to about 8 wt-% medium chain carboxylic acid, about 1 to about 10 wt-% medium chain carboxylic acid, about 1 to about 8 wt-% medium chain carboxylic acid, about 1.5 to about 6 wt-% medium chain carboxylic acid, about 2 to about 8 wt-% medium chain carboxylic acid, about 2 to about 6 wt-% medium chain carboxylic acid, about 2 to about 4 wt-% medium chain carboxylic acid, about 2.5 to about 5 wt-% medium chain carboxylic acid, about 3 to about 6 wt-% medium chain carboxylic acid, or about 3 to about 5 wt-% medium chain carboxylic acid. The composition can include any of these ranges or amounts not modified by about.

In certain embodiments, the present composition includes about 0 to about 98 wt-% carrier, about 0.001 to about 99.99 wt-% carrier, about 0.2 to about 60 wt-% carrier, about 1 to about 98 wt-% carrier, about 5 to about 99.99 wt-% carrier, about 5 to about 97 wt-% carrier, about 5 to about 90 wt-% carrier, about 5 to about 70 wt-% carrier, about 5 to about 20 wt-% carrier, about 10 to about 90 wt-% carrier, about 10 to about 80 wt-% carrier, about 10 to about 50 wt-% carrier, about 10 to about 20 wt-% carrier, about 15 to about 70 wt-% carrier, about 15 to about 80 wt-% carrier, about 20 to about 70 wt-% carrier, about 20 to about 50 wt-% carrier, about 20 to about 40 wt-% carrier, about 20 to about 30 wt-% carrier, about 30 to about 75 wt-% carrier, about 30 to about 70 wt-% carrier, about 40 to about 99.99 wt-% carrier, about 40 to about 90 wt-% carrier, or about 60 to about 70 wt-% carrier. The composition can include any of these ranges or amounts not modified by about.

In certain embodiments, the present composition includes about 0.001 to about 80 wt-% solubilizer, about 0.001 to about 60 wt-% solubilizer, about 1 to about 80 wt-% solubilizer, about 1 to about 25 wt-% solubilizer, about 1 to about 20 wt-% solubilizer, about 2 to about 70 wt-% solubilizer, about 2 to about 60 wt-% solubilizer, about 2 to about 20 wt-% solubilizer, about 3 to about 65 wt-% solubilizer, about 3 to about 15 wt-% solubilizer, about 4 to about 10 wt-% solubilizer, about 4 to about 20 wt-% solubilizer, about 5 to about 70 wt-% solubilizer, about 5 to about 60 wt-% solubilizer, about 5 to about 20 wt-% solubilizer, about 10 to about 70 wt-% solubilizer, about 10 to about 65 wt-% solubilizer, about 10 to about 20 wt-% solubilizer, about 20 to about 60 wt-% solubilizer, or about 40 to about 60 wt-% solubilizer. The composition can include any of these ranges or amounts not modified by about.

In certain embodiments, the present composition includes about 0.001 to about 30 wt-% oxidizing agent, about 0.001 to about 10 wt-% oxidizing agent, 0.002 to about 10 wt-% oxidizing agent, about 2 to about 30 wt-% oxidizing agent, about 2 to about 25 wt-% oxidizing agent, about 2 to about 20 wt-% oxidizing agent, about 4 to about 20 wt-% oxidizing agent, about 5 to about 10 wt-% oxidizing agent, or about 6 to about 10 wt-% oxidizing agent. The composition can include any of these ranges or amounts not modified by about.

In certain embodiments, the present composition includes about 0.001 to about 50 wt-% acidulant, about 0.001 to about 30 wt-% acidulant, about 1 to about 50 wt-% acidulant, about 1 to about 30 wt-% acidulant, about 2 to about 40 wt-% acidulant, about 2 to about 10 wt-% acidulant, about 3 to about 40 wt-% acidulant, about 5 to about 40 wt-% acidulant, about 5 to about 25 wt-% acidulant, about 10 to about 40 wt-% acidulant, about 10 to about 30 wt-% acidulant, about 15 to about 35 wt-% acidulant, about 15 to about 30 wt-% acidulant, or about 40 to about 60 wt-% acidulant. The composition can include any of these ranges or amounts not modified by about.

In certain embodiments, the present composition includes about 0.001 to about 50 wt-% stabilizing agent, about 0.001 to about 5 wt-% stabilizing agent, about 0.5 to about 50 wt-% stabilizing agent, about 1 to about 50 wt-% stabilizing agent, about 1 to about 30 wt-% stabilizing agent, about 1 to about 10 wt-% stabilizing agent, about 1 to about 5 wt-% stabilizing agent, about 1 to about 3 wt-% stabilizing agent, about 2 to about 10 wt-% stabilizing agent, about 2 to about 5 wt-% stabilizing agent, or about 5 to about 15 wt-% stabilizing agent. The composition can include any of these ranges or amounts not modified by about.

Compositions of Medium Chain Carboxylic Acids and/or Peroxycarboxylic Acids

Peroxycarboxylic (or percarboxylic) acids generally have the formula $R(CO_3H)_n$, where, for example, R is an alkyl, arylalkyl, cycloalkyl, aromatic, or heterocyclic group, and n is one, two, or three, and named by prefixing the parent acid with peroxy. The R group can be saturated or unsaturated as well as substituted or unsubstituted. The composition and methods of the invention can employ medium chain peroxycarboxylic acids containing, for example, 6 to 12 carbon atoms. For example, medium chain peroxycarboxylic (or percarboxylic) acids can have the formula $R(CO_3H)_n$, where R is a $C_5$-$C_{11}$ alkyl group, a $C_5$-$C_{11}$ cycloalkyl, a $C_5$-$C_{11}$ arylalkyl group, $C_5$-$C_{11}$ aryl group, or a $C_5$-$C_{11}$ heterocyclic group; and n is one, two, or three.

Peroxycarboxylic acids can be made by the direct action of an oxidizing agent on a carboxylic acid, by autoxidation of aldehydes, or from acid chlorides, and hydrides, or carboxylic anhydrides with hydrogen or sodium peroxide. In an embodiment, the medium chain percarboxylic acids can be made by the direct, acid catalyzed equilibrium action of hydrogen peroxide on the medium chain carboxylic acid. Scheme 1 illustrates an equilibrium between carboxylic acid and oxidizing agent (Ox) on one side and peroxycarboxylic acid and reduced oxidizing agent ($Ox_{red}$) on the other:

$$RCOOH + Ox \leftrightharpoons RCOOOH + OX_{red} \quad (1)$$

Scheme 2 illustrates an embodiment of the equilibrium of scheme 1 in which the oxidizing agent is hydrogen peroxide on one side and peroxycarboxylic acid and water on the other:

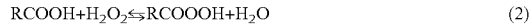

$$RCOOH + H_2O_2 \leftrightharpoons RCOOOH + H_2O \quad (2)$$

In conventional mixed peroxycarboxylic acid compositions it is believed that the equilibrium constant for the reaction illustrated in scheme 2 is about 2.5, which may reflect the equilibrium for acetic acid. Although not limiting to the present invention, it is believed that the present compositions have an equilibrium constant of about 4.

Peroxycarboxylic acids useful in the compositions and methods of the present invention include peroxypentanoic, peroxyhexanoic, peroxyheptanoic, peroxyoctanoic, peroxynonanoic, peroxydecanoic, peroxyundecanoic, peroxydodecanoic, peroxyascorbic, peroxyadipic, peroxycitric, peroxypimelic, or peroxysuberic acid, mixtures thereof, or the like. The alkyl backbones of these medium chain peroxycarboxylic acids can be straight chain, branched, or a mixture thereof. Peroxy forms of carboxylic acids with more than one carboxylate moiety can have one or more (e.g., at least one) of the carboxyl moieties present as peroxycarboxyl moieties.

Peroxyoctanoic (or peroctanoic) acid is a peroxycarboxylic acid having the formula, for example, of n-peroxyoctanoic acid: $CH_3(CH_2)_6COOOH$. Peroxyoctanoic acid can be an acid with a straight chain alkyl moiety, an acid with a branched alkyl moiety, or a mixture thereof. Peroxyoctanoic acid is surface active and can assist in wetting hydrophobic surfaces, such as those of microbes.

The composition of the present invention can include a carboxylic acid. Generally, carboxylic acids have the formula R—COOH wherein the R can represent any number of different groups including aliphatic groups, alicyclic groups, aromatic groups, heterocyclic groups, all of which can be saturated or unsaturated as well as substituted or unsubstituted. Carboxylic acids can have one, two, three, or more carboxyl groups. The composition and methods of the invention typically employ medium chain carboxylic acids containing, for example, 6 to 12 carbon atoms. For example, medium chain carboxylic acids can have the formula R—COOH in which R can be a $C_5$-$C_{11}$ alkyl group, a $C_5$-$C_{11}$ cycloalkyl group, a $C_5$-$C_{11}$ arylalkyl group, $C_5$-$C_{11}$ aryl group, or a $C_5$-$C_{11}$ heterocyclic group.

Suitable medium chain carboxylic acids include pentanoic, hexanoic, heptanoic, octanoic, nonanoic, decanoic, undecanoic, dodecanoic, ascorbic, citric, adipic, pimelic, and suberic acid. The alkyl backbones of these medium chain carboxylic acids can be straight chain, branched, or a mixture thereof. Carboxylic acids which are generally useful are those having one or two carboxyl groups where the R group is a primary alkyl chain having a length of $C_4$ to $C_{11}$. The primary alkyl chain is that carbon chain of the molecule having the greatest length of carbon atoms and directly appending carboxyl functional groups.

The present compositions and methods include a medium chain peroxycarboxylic acid. The medium chain peroxycarboxylic acid can include or be a C6 to C12 peroxycarboxylic acid. The C6 to C12 peroxycarboxylic acid can include or be peroxyhexanoic acid, peroxyheptanoic acid, peroxyoctanoic acid, peroxynonanoic acid, peroxydecanoic acid, peroxyundecanoic acid, peroxydodecanoic acid, or mixture thereof. The medium chain peroxycarboxylic acid can include or be a C7 to C12 peroxycarboxylic acid. The C7 to C12 peroxycarboxylic acid can include or be peroxyheptanoic acid, peroxyoctanoic acid, peroxynonanoic acid, peroxydecanoic acid, peroxyundecanoic acid, peroxydodecanoic acid, or mixture thereof. The medium chain peroxycarboxylic acid can include or be a C6 to C10 peroxycarboxylic acid. The C6 to C10 peroxycarboxylic acid can include or be peroxyhexanoic acid, peroxyheptanoic acid, peroxyoctanoic acid, peroxynonanoic acid, peroxydecanoic acid, or mixture thereof. The medium chain peroxycarboxylic acid can include or be a C8 to C10 peroxycarboxylic acid. The C8 to C10 peroxycarboxylic acid can include or be peroxyoctanoic acid, peroxynonanoic acid, peroxydecanoic acid, or mixture thereof. In certain embodiments, the medium chain peroxyoctanoic acid includes or is peroxyoctanoic acid, peroxydecanoic acid, or mixture thereof. In an embodiment, the medium chain peroxycarboxylic acid includes or is peroxyoctanoic acid.

In certain embodiments, the present composition includes about 0.0005 to about 5 wt-% medium chain peroxycarboxylic acid, about 0.3 to about 7 wt-% medium chain peroxycarboxylic acid, about 0.5 to about 5 wt-% medium chain peroxycarboxylic acid, about 0.5 to about 4 wt-% medium chain peroxycarboxylic acid, about 0.8 to about 3 wt-% medium chain peroxycarboxylic acid, about 1 to about 3 wt-% medium chain peroxycarboxylic acid, or about 1 to about 2 wt-% medium chain peroxycarboxylic acid. The composition can include any of these ranges or amounts not modified by about.

In an embodiment, the present compositions and methods include a medium chain carboxylic acid. The medium chain carboxylic acid can include or be a C6 to C12 carboxylic acid. The C6 to C12 carboxylic acid can include or be hexanoic acid, heptanoic acid, octanoic acid, nonanoic acid, decanoic acid, undecanoic acid, dodecanoic acid, or mixture thereof. The medium chain carboxylic acid can include or be a C7 to C12 carboxylic acid. The C7 to C12 carboxylic acid can include or be heptanoic acid, octanoic acid, nonanoic acid, decanoic acid, undecanoic acid, dodecanoic acid, or mixture thereof. The medium chain peroxycarboxylic acid can include or be a C6 to C10 carboxylic acid. The C6 to C10 carboxylic acid can include or be hexanoic acid, heptanoic acid, octanoic acid, nonanoic acid, decanoic acid, or mixture thereof. The medium chain carboxylic acid can include or be a C8 to C10 carboxylic acid. The C8 to C10 carboxylic acid can include or be octanoic acid, nonanoic acid, decanoic acid, or mixture thereof. In certain embodiments, the medium chain carboxylic acid includes or is octanoic acid, decanoic acid, or mixture thereof. In an embodiment, the medium chain carboxylic acid includes or is octanoic acid.

In certain embodiments, the present composition includes about 0.001 to about 8 wt-% medium chain carboxylic acid, about 1 to about 10 wt-% medium chain carboxylic acid, about 1 to about 8 wt-% medium chain carboxylic acid, about 1.5 to about 6 wt-% medium chain carboxylic acid, about 2 to about 8 wt-% medium chain carboxylic acid, about 2 to about 6 wt-% medium chain carboxylic acid, about 2 to about 4 wt-% medium chain carboxylic acid, about 2.5 to about 5 wt-% medium chain carboxylic acid, about 3 to about 6 wt-% medium chain carboxylic acid, or about 3 to about 5 wt-% medium chain carboxylic acid. The composition can include any of these ranges or amounts not modified by about.

In an embodiment, the compositions and methods include a medium chain peroxycarboxylic acid and the corresponding medium chain carboxylic acid.

In an embodiment, the present composition includes an amount of medium chain peroxycarboxylic acid effective for killing one or more (e.g., at least one) of the food-borne pathogenic bacteria associated with a food product, such as *Salmonella typhimurium, Salmonella javiana, Campylobacter jejuni, Listeria monocytogenes*, and *Escherichia coli* O157:H7, yeast, mold, and the like. In an embodiment, the present composition includes an amount of medium chain peroxycarboxylic acid effective for killing one or more (e.g., at least one) of the pathogenic bacteria associated with a health care surfaces and environments, such as *Salmonella typhimurium, Staphylococcus aureus, Salmonella choleraesurus, Pseudomonas aeruginosa, Escherichia coli*, mycobacteria, yeast, mold, and the like. The compositions and methods of the present invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compositions and methods of the present invention, as described above, have activity against a wide variety of human pathogens. The present compositions and methods can kill a wide variety of microorganisms on a food processing surface, on the surface of a food product, in water used for washing or processing of food product, on a health care surface, or in a health care environment.

Embodiments of the present invention include medium chain carboxylic acid and medium chain peroxycarboxylic acid, and certain embodiments specifically exclude short chain peroxycarboxylic acid, short chain carboxylic acid, or mixture thereof. Nonetheless embodiments of the present compositions can include short chain peroxycarboxylic acid, short chain carboxylic acid, or mixture thereof. It is not intended that addition of short chain peroxycarboxylic acid, short chain carboxylic acid, or mixture thereof to a composition should necessarily take a composition outside the spirit and scope of the present invention.

Solubilizers

The present compositions can include a solubilizer. The present invention relates to solubilizers for medium chain carboxylic acids and medium chain peroxycarboxylic acids. In an embodiment, the solubilizer can increase or maintain the solubility in the composition of the medium chain peroxycarboxylic acid or the medium chain carboxylic acid. The present compositions and methods can include any of a variety of suitable solubilizers. For example, the solubilizer can include a solvent, a surfactant, or a mixture thereof. In an embodiment, the surfactant can be employed as a solvent. In an embodiment, the surfactant can form a microemulsion. In an embodiment, the composition including the present solubilizer takes the form of a viscoelastic gel or liquid. In an embodiment, the solubilizer is effective to dissolve octanoic acid at a concentration of 5 wt-% in water. In an embodiment, the solubilizer is effective to dissolve octanoic acid at a concentration of 4 wt-% in water. In an embodiment, the solubilizer is effective to dissolve octanoic acid at a concentration of 3 wt-% in water. In an embodiment, the solubilizer is effective to dissolve octanoic acid at a concentration of 2 wt-% in water.

In certain embodiments, the present composition includes about 0.001 to about 80 wt-% solubilizer, about 0.001 to about 60 wt-% solubilizer, about 1 to about 80 wt-% solubilizer, about 1 to about 25 wt-% solubilizer, about 1 to about 20 wt-% solubilizer, about 2 to about 70 wt-% solubilizer, about 2 to about 60 wt-% solubilizer, about 2 to about 20 wt-% solubilizer, about 3 to about 65 wt-% solubilizer, about 3 to about 15 wt-% solubilizer, about 4 to about 10 wt-% solubilizer, about 4 to about 20 wt-% solubilizer, about 5 to about 70 wt-% solubilizer, about 5 to about 60 wt-% solubilizer, about 5 to about 20 wt-% solubilizer, about 10 to about 70 wt-% solubilizer, about 10 to about 65 wt-% solubilizer, about 10 to about 20 wt-% solubilizer, about 20 to about 60 wt-% solubilizer, or about 40 to about 60 wt-% solubilizer. The composition can include any of these ranges or amounts not modified by about.

Solvent Solubilizers and Compositions Including them

In an embodiment, the present compositions and methods can include as solubilizer one or more (e.g., at least one) solvents. Suitable solvents include any of a variety of solvents that solubilize but do not significantly degrade the medium chain peroxycarboxylic acid. Suitable solvents include polyalkylene oxide, capped polyalkylene oxide, glycol ether, nonionic surfactant, mixtures thereof, or the like.

In an embodiment, the present composition includes medium chain peroxycarboxylic acid; medium chain carboxylic acid; carrier; and polyalkylene oxide, capped polyalkylene oxide, nonionic surfactant, or mixture thereof. For example, the present composition can include about 0.5 to about 5 wt-% medium chain peroxycarboxylic acid; about 1 to about 10 wt-% medium chain carboxylic acid; about 1 to about 98 wt-% carrier; and about 1 to about 80 wt-% polyalkylene oxide, capped polyalkylene oxide, nonionic surfactant, or mixture thereof. For example, the present composition can include about 0.5 to about 5 wt-% medium chain peroxycarboxylic acid; about 1 to about 10 wt-% medium chain carboxylic acid; about 5 to about 35 wt-% carrier; and about 20 to about 65 wt-% polyalkylene oxide, capped polyalkylene oxide, nonionic surfactant, or mixture thereof. For example, the present composition can include about 0.5 to about 5 wt-% medium chain peroxycarboxylic acid; about 1 to about 10 wt-% medium chain carboxylic acid; about 10 to about 35 wt-% carrier; and about 40 to about 60 wt-% polyalkylene oxide, capped polyalkylene oxide, nonionic surfactant, or mixture thereof. In an embodiment, the present composition includes solvent solubilizer and less than or equal to 35 wt-% carrier (e.g., water). The composition can include any of these ranges or amounts not modified by about.

In an embodiment, the present composition includes C8 peroxycarboxylic acid; C8 carboxylic acid; water; and polyalkylene oxide, capped polyalkylene oxide, nonionic surfactant, or mixture thereof. For example, the present composition can include about 0.5 to about 5 wt-% C8 peroxycarboxylic acid; about 1 to about 10 wt-% C8 carboxylic acid; about 1 to about 98 wt-% water; and about 1 to about 80 wt-% polyalkylene oxide, capped polyalkylene oxide, nonionic surfactant, or mixture thereof. For example, the present composition can include about 0.5 to about 5 wt-% C8 peroxycarboxylic acid; about 1 to about 10 wt-% C8 carboxylic acid; about 5 to about 35 wt-% water; and about 20 to about 65 wt-% polyalkylene oxide, capped polyalkylene oxide, nonionic surfactant, or mixture thereof. For example, the present composition can include about 0.5 to about 5 wt-% C8 peroxycarboxylic acid; about 1 to about 10 wt-% C8 carboxylic acid; about 10 to about 35 wt-% water; and about 40 to about 60 wt-% polyalkylene oxide, capped polyalkylene oxide, nonionic surfactant, or mixture thereof. The composition can include any of these ranges or amounts not modified by about.

In certain embodiments, the present composition includes about 0.001 to about 80 wt-% solvent as solubilizer, about 0.001 to about 60 wt-% solvent as solubilizer, about 1 to about 80 wt-% solvent as solubilizer, about 5 to about 70 wt-% solvent as solubilizer, about 10 to about 65 wt-% solvent as solubilizer, or about 20 to about 60 wt-% solvent as solubilizer. The composition can include any of these ranges or amounts not modified by about.

In an embodiment, when the present compositions and methods include a solvent as solubilizer, they need not include a significant amount, or even any, of a short chain peroxycarboxylic acid, a short chain carboxylic acid, or a mixture thereof. Examples of short chain carboxylic acids include formic acid, acetic acid, propionic acid, and butanoic acid. Short chain carboxylic acids and peroxycarboxylic acids include those with 4 or fewer carbon atoms. In an embodiment, the present compositions and methods including a solvent solubilizer need not include substantial amounts of short chain peroxycarboxylic acid. In an embodiment, the present compositions and methods including a solvent solubilizer can be free of added short chain peroxycarboxylic acid.

In an embodiment, the present compositions and methods including a solvent solubilizer can include medium chain peroxycarboxylic acid in greater proportion compared to the short chain peroxycarboxylic acid than found in conventional compositions. For example, the present compositions and methods can include solvent solubilizer and about 1 or more parts of medium chain peroxycarboxylic acid for each 8 parts of short chain carboxylic acid, short chain peroxycarboxylic acid, or mixture thereof. For example, the present compositions and methods can include solvent solubilizer and short chain carboxylic acid, short chain peroxycarboxylic acid, or mixture thereof at a level insufficient to cause odor offensive to a typical person.

Polyalkylene Oxide Solubilizers

Suitable polyalkylene oxides include polyethylene glycol, polypropylene glycol, polybutylene glycol, mixtures thereof, or the like. Suitable capped polyalkylene oxides include mono-alkyl and di-alkyl ethers of the respective polyalkylene oxides, such as mono- and di-methyl ethers of polyalkylene glycol, mono- and di-ethyl ethers of polyalkylene glycol, mono- and di-propyl ethers of polyalkylene glycol, mono- and di-butyl ethers of polyalkylene glycol, mixtures thereof, or the like. Suitable capped polyalkylene oxides include methyl polyethylene glycol (e.g., the monomethyl ether of polyethylene glycol), dimethyl polyethylene glycol (e.g., the dimethyl ether of polyethylene glycol), mixtures thereof, or the like.

Glycol Ether Solubilizers

Suitable solvent solubilizers include glycol ethers. Suitable glycol ethers include diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether (commercially available as DOWANOL EPH™ from Dow Chemical Co.), propylene glycol phenyl ether (commercially available as DOWANOL PPH™ from Dow Chemical Co.), and the like, or mixtures thereof. Additional suitable commercially available glycol ethers (all of which are available from Union Carbide Corp.) include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

Nonionic Surfactants

Suitable nonionic surfactants for use as solvents include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-$(EO)_5(PO)_4$) and Dehypon LS-36 (R-$(EO)_3(PO)_6$); and capped alcohol alkoxylates, such as Plurafac LF221 and Tegoten EC 11; mixtures thereof, or the like. When employed as a solvent a surfactant, such as a nonionic surfactant, can be at concentrations higher than those conventionally employed as surfactant.

Semi-Polar Nonionic Surfactants

The semi-polar type of nonionic surface active agents are another class of nonionic surfactant useful in compositions of the present invention. Semi-polar nonionic surfactants include the amine oxides, phosphine oxides, sulfoxides and their alkoxylated derivatives.

Amine oxides are tertiary amine oxides corresponding to the general formula:

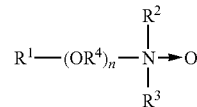

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Surfactant Solubilizers and Compositions Including them

In an embodiment, the present compositions and methods can include as solubilizer one or more (e.g., at least one) surfactants, e.g., a microemulsion forming surfactant. Suitable surfactants include anionic surfactant, cationic surfactant, amphoteric surfactant, zwitterionic surfactant, mixtures thereof, or the like. Suitable microemulsion forming surfactants include anionic surfactant, cationic surfactant, amphoteric surfactant, zwitterionic surfactant, mixtures thereof, or the like. Suitable microemulsion forming surfactants include anionic surfactant. A microemulsion forming surfactant can form a microemulsion in a composition including a medium chain peroxycarboxylic acid, a medium chain carboxylic acid, or a mixture thereof. In an embodiment, the present composition includes a microemulsion.

In an embodiment, the present composition can be determined to be a microemulsion by testing the composition for being a shear thinning viscoelastic gel or liquid that has a blue tyndall appearance. Although not limiting to the present invention, blue tyndall appearance is believed to indicate a heterogeneous system of a small, suspended dispersion (e.g., a microemulsion), which is effective in scattering blue light.

In an embodiment, the present composition can be determined to be a microemulsion by testing the ability to form a physically stable composition at different concentrations of surfactant solubilizer. A microemulsion can yield a curve with a maximum of physical stability at a concentration with unstable compositions at higher and lower concentrations. Typically, mixtures of solvents and surfactants (e.g., acetic acid and surfactant) do not form microemulsions.

In an embodiment, the composition including surfactant solubilizer takes the form of a viscoelastic gel or liquid. Increasing the concentration of the medium chain carboxylic acid, medium chain peroxycarboxylic acid, or mixture thereof can increase the degree to which the composition is a viscoelastic gel or liquid. Increasing the concentration of the surfactant solubilizer can increase the degree to which the composition is a viscoelastic gel or liquid. In an embodiment, the gel can be sufficiently viscoelastic to hold its molded shape. Alkyl benzene sulfonate surfactant (e.g., LAS) can be employed to form a viscoelastic gel or liquid that can hold its molded shape. In an embodiment, the alkyl benzene sulfonate surfactant containing viscoelastic gel can hold its shape even at 60° C.

Although not limiting to the present invention, the present compositions may include medium chain peroxycarboxylic acid sequestered in the surfactant of the microemulsion. This can stabilize the peroxycarboxylic acid by keeping it away from impurities or reducing agents in the bulk water. This can increase the production of peroxycarboxylic acid by pulling it out of solution. Although not limiting to the present invention, it is believed that one explanation for the viscoelastic properties of gels of the present compositions is that they are due to repulsive forces between the dispersions/droplets that are stabilized by the microemulsion-forming surfactant. Surfactants that are charged may increase the electrostatic repulsion. Suitable charged surfactants include anionic surfactants.

In an embodiment, the present composition includes anionic surfactant and another surfactant or surfactants. For example, the present compositions can include anionic surfactant and nonionic surfactant or semi-polar nonionic surfactant. For example, the present compositions can include anionic surfactant and alkyl amine oxide or alkyl dimethyl amine.

In an embodiment, the present composition includes medium chain peroxycarboxylic acid; medium chain carboxylic acid; carrier; and one or more (e.g., at least one) surfactants, e.g., microemulsion forming surfactants. For example, the present composition can include about 0.5 to about 5 wt-% medium chain peroxycarboxylic acid; about 1 to about 10 wt-% medium chain carboxylic acid; about 5 to about 97 wt-% carrier; and about 1 to about 20 wt-% surfactant, e.g., microemulsion forming surfactant. For example, the present composition can include about 0.5 to about 5 wt-% medium chain peroxycarboxylic acid; about 1 to about 10 wt-% medium chain carboxylic acid; about 15 to about 80 wt-% carrier; and about 1 to about 20 wt-% surfactant, e.g., microemulsion forming surfactant. For example, the present composition can include about 0.5 to about 5 wt-% medium chain peroxycarboxylic acid; about 1 to about 10 wt-% medium chain carboxylic acid; about 30 to about 70 wt-% carrier; and about 2 to about 20 wt-% surfactant, e.g., microemulsion forming surfactant. In an embodiment, the present composition includes surfactant or microemulsion former solubilizer and greater than or equal to 35 wt-% carrier (e.g., water). The composition can include any of these ranges or amounts not modified by about.

In an embodiment, the present composition includes C8 peroxycarboxylic acid; C8 carboxylic acid; water; and one or more (e.g., at least one) surfactants, e.g., microemulsion forming surfactants. For example, the present composition can include about 0.5 to about 5 wt-% C8 peroxycarboxylic acid; about 1 to about 10 wt-% C8 carboxylic acid; about 5 to about 97 wt-% water; and about 1 to about 20 wt-% surfactant, e.g., microemulsion forming surfactant. For example, the present composition can include about 0.5 to about 5 wt-% C8 peroxycarboxylic acid; about 1 to about 10 wt-% C8 carboxylic acid; about 15 to about 80 wt-% water; and about 1 to about 20 wt-% surfactant, e.g., microemulsion forming surfactant. For example, the present composition can include about 0.5 to about 5 wt-% C8 peroxycarboxylic acid; about 1 to about 10 wt-% C8 carboxylic acid; about 30 to about 70 wt-% water; and about 2 to about 20 wt-% surfactant, e.g., microemulsion forming surfactant. The composition can include any of these ranges or amounts not modified by about.

In certain embodiments, the present composition includes about 0.001 to about 60 wt-% surfactant, e.g., microemulsion forming surfactant, as solubilizer, about 1 to about 25 wt-% surfactant, e.g., microemulsion forming surfactant, as solubilizer, about 1 to about 20 wt-% surfactant, e.g., microemulsion forming surfactant, as solubilizer, about 2 to about 20 wt-% surfactant, e.g., microemulsion forming surfactant, as solubilizer, about 3 to about 15 wt-% surfactant, e.g., microemulsion forming surfactant, as solubilizer, about 4 to about 20 wt-% surfactant, e.g., microemulsion forming surfactant, as solubilizer, about 4 to about 10 wt-% surfactant, e.g., microemulsion forming surfactant, as solubilizer, about 5 to about 20 wt-% surfactant, e.g., microemulsion forming surfactant, as solubilizer, or about 10 to about 20 wt-% surfactant, e.g., microemulsion forming surfactant, as solubilizer. The composition can include any of these ranges or amounts not modified by about.

Anionic Surfactants

The present composition can include an anionic surfactant as solubilizer. Suitable anionic surfactants include organic sulfonate surfactant, organic sulfate surfactant, phosphate ester surfactant, carboxylate surfactant, mixtures thereof, or the like. In an embodiment, the anionic surfactant includes alkyl sulfonate, alkylaryl sulfonate, alkylated diphenyl oxide disulfonate, alkylated naphthalene sulfonate, alcohol alkoxylate carboxylate, sarcosinate, taurate, acyl amino acid, alkanoic ester, phosphate ester, sulfuric acid ester, salt or acid form thereof, or mixture thereof. The particular salts will be suitably selected depending upon the particular formulation and the needs therein.

Suitable anionic surfactants include sulfonic acids (and salts), such as isethionates (e.g. acyl isethionates), alkylaryl sulfonic acids and salts thereof, alkyl sulfonates, secondary alkane sulfonates, and the like.

Examples of suitable synthetic, water soluble anionic detergent compounds include the ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from about 5 to about 18 carbon atoms in the alkyl group in a straight or branched chain, e.g., the salts of alkyl benzene sulfonates or of alkyl toluene, xylene, cumene and phenol sulfonates; alkyl naphthalene sulfonate, diamyl naphthalene sulfonate, and dinonyl naphthalene sulfonate and alkoxylated derivatives or their free acids. Suitable sulfonates include olefin sulfonates, such as long chain alkene sulfonates, long chain hydroxyalkane sulfonates or mixtures of alkenesulfonates and hydroxyalkanesulfonates. Suitable sulfonates include secondary alkane sulfonates.

In certain embodiments, the present compositions including an anionic surfactant, such as a normal C8 sulfonate, can be non-foam or low foam compositions. Such compositions can be advantageous for applications such as clean in place, machine warewashing, destaining, and sanitizing, laundry washing, destaining, and sanitizing, etc.

For applications in which foaming is desirable, a foaming agent can be added as part of the present composition or separately. In a two-step offering, a foaming agent can be combined with a dilution of the non-foam or low foam composition to form a foaming use solution. In a one-step offering, the foaming agent can be incorporated into the concentrated composition. One suitable foaming agent is LAS acid. LAS acid can form a microemulsion in the present compositions. LAS acid can form a viscoelastic gel or liquid in the present compositions. Additional suitable foaming agents include secondary alkane sulfonate, alkylated diphenyl oxide disulfonate (e.g., C12 alkyl diphenyl oxide disulfonate), alkyl ether sulfate (e.g., with n=1-3) (e.g., sodium laureth sulfate (with n=1, 2, or 3)), sodium lauryl sulfate, or the like.

In an embodiment, such foaming agents provide a foaming composition with one or more desirable foaming characteristics. Desirable foaming characteristics include, for example, foam being visible for about 5 min after forming the foam; foam with continuous and good drainage (e.g., when applied to a vertical surface); foam that dries to a clear appearance, e.g., that leaves no visible residue on a stainless steel surface; and/or foam that can be applied with a moderate or low odor compared to a conventional foam containing peroxyacetic acid.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N-($C_1$-$C_4$ alkyl) and —N—($C_1$-$C_2$ hydroxyalkyl)glucamine sulfates, and sulfates of alkylpolysaccharides such as the sulfates of alkylpolyglucoside, and the like. Also included are the alkyl sulfates, alkyl poly(ethyleneoxy)ether sulfates and aromatic poly(ethyleneoxy)sulfates such as the sulfates or condensation products of ethylene oxide and nonyl phenol (usually having 1 to 6 oxyethylene groups per molecule).

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of Formula 3:

$$R\text{—}O\text{—}(CH_2CH_2O)_n(CH_2)_m\text{—}CO_2X \qquad (3)$$

in which R is a $C_8$ to $C_{22}$ alkyl group or

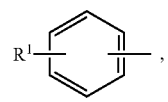

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In an embodiment, in Formula 3, n is an integer of 4 to 10 and m is 1. In an embodiment, in Formula 3, R is a $C_8$-$C_{16}$ alkyl group. In an embodiment, in Formula 3, R is a $C_{12}$-$C_{14}$ alkyl group, n is 4, and m is 1.

In an embodiment, in Formula 3, R is

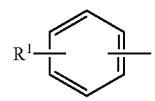

and $R^1$ is a $C_6$-$C_{12}$ alkyl group. In an embodiment, in Formula 3, $R^1$ is a $C_9$ alkyl group, n is 10 and m is 1. Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{1-3}$ alkyl polyethoxy (7) carboxylic acid.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" *Cosmetics & Toiletries*, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazoline derivatives having application in the present invention generally have the general formula:

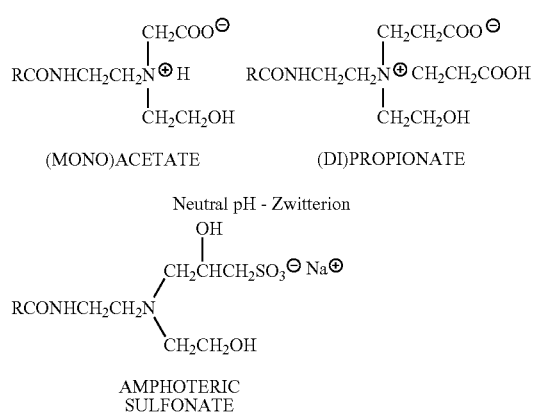

(MONO)ACETATE (DI)PROPIONATE

AMPHOTERIC SULFONATE wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl)alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—N+($CH_2$—$CH_2$—$CO_2Na$)$_2$—$CH_2$—$CH_2$—OH or $C_{12}$-alkyl-C(O)—N(H)—$CH_2$—$CH_2$—N+($CH_2$—$CO_2Na$)$_2$—$CH_2$—$CH_2$—OH.

Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

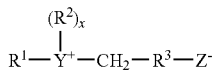

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S [N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

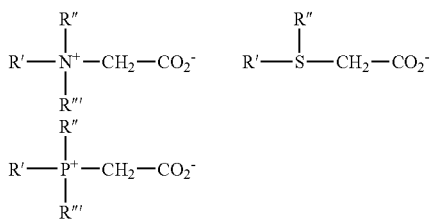

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12}$-16 acylamidopentanediethylbetaine; and C12-16 acylmethylamidodimethylbetaine.

Sultaines useful in the present invention include those compounds having the formula $(R(R^1)_2N^+R^2SO^{3-}$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

In an embodiment, the composition of the present invention includes a betaine. For example, the composition can include cocoamidopropyl betaine.

Embodiments of Compositions

Some examples of representative constituent concentrations for embodiments of the present compositions can be found in Tables A-C, in which the values are given in wt-% of the ingredients in reference to the total composition weight. In certain embodiments, the proportions and amounts in Tables A-C can be modified by "about".

TABLE A

| Ingredient | wt-% | wt-% | wt-% | wt-% |
| --- | --- | --- | --- | --- |
| medium chain peroxycarboxylic acid | 0.3-7 | 0.5-5 | 0.5-4 | 1-3 |
| medium chain carboxylic acid | 1-10 | 2-8 | 2-6 | 2.5-5 |
| solubilizer | 1-80 | 2-70 | 3-65 | 5-60 |
| carrier | 0-98 | 5-90 | 10-80 | 20-70 |

TABLE B

| Ingredient | wt-% | wt-% | wt-% | wt-% |
| --- | --- | --- | --- | --- |
| medium chain peroxycarboxylic acid | 0.3-7 | 0.5-5 | 0.5-4 | 1-3 |
| medium chain carboxylic acid | 1-10 | 2-8 | 3-6 | 3-5 |
| solubilizer | 1-80 | 5-70 | 10-65 | 20-60 |
| carrier | 0-98 | 0.2-60 | 5-20 | 20-40 |

TABLE C

| Ingredient | wt-% | wt-% | wt-% | wt-% |
| --- | --- | --- | --- | --- |
| medium chain peroxycarboxylic acid | 0.3-7 | 0.5-5 | 0.5-4 | 1-2 |
| medium chain carboxylic acid | 1-10 | 1-8 | 1.5-6 | 2-4 |
| solubilizer | 1-25 | 2-20 | 3-15 | 4-10 |
| carrier | 5-97 | 10-90 | 15-70 | 30-75 |

Some examples of representative constituent concentrations for additional embodiments of the present compositions can be found in Tables D-F, in which the values are given in wt-% of the ingredients in reference to the total composition weight. In certain embodiments, the proportions and amounts in Tables D-F can be modified by "about".

TABLE D

| Ingredient | wt-% | wt-% | wt-% | wt-% |
|---|---|---|---|---|
| medium chain peroxycarboxylic acid | 0.3-7 | 0.5-5 | 0.5-4 | 1-3 |
| medium chain carboxylic acid | 1-10 | 2-8 | 2-6 | 2.5-5 |
| solubilizer | 1-80 | 2-70 | 3-65 | 5-60 |
| carrier | 0-98 | 5-90 | 10-80 | 20-70 |
| oxidizing agent | 2-30 | 2-25 | 4-20 | 6-10 |
| acidulant | 1-50 | 2-40 | 3-40 | 5-40 |
| stabilizing agent | 1-50 | 1-10 | 1-5 | 1-3 |

TABLE E

| Ingredient | wt-% | wt-% | wt-% | wt-% |
|---|---|---|---|---|
| medium chain peroxycarboxylic acid | 0.3-7 | 0.5-5 | 0.5-4 | 1-3 |
| medium chain carboxylic acid | 1-10 | 2-8 | 3-6 | 3-5 |
| solubilizer | 1-80 | 5-70 | 10-65 | 20-60 |
| carrier | 0-98 | 0.2-60 | 5-20 | 20-40 |
| oxidizing agent | 2-30 | 2-25 | 4-20 | 6-10 |
| acidulant | 1-50 | 2-40 | 3-40 | 5-40 |
| stabilizing agent | 1-50 | 1-10 | 1-5 | 1-3 |

TABLE F

| Ingredient | wt-% | wt-% | wt-% | wt-% |
|---|---|---|---|---|
| medium chain peroxycarboxylic acid | 0.3-7 | 0.5-5 | 0.5-4 | 1-2 |
| medium chain carboxylic acid | 1-10 | 1-8 | 1.5-6 | 2-4 |
| solubilizer | 1-25 | 2-20 | 3-15 | 4-10 |
| carrier | 5-97 | 10-90 | 15-70 | 30-75 |
| oxidizing agent | 2-30 | 2-25 | 4-20 | 6-10 |
| acidulant | 1-50 | 2-40 | 3-35 | 5-30 |
| stabilizing agent | 1-50 | 1-15 | 1-5 | 1-3 |

In an embodiment, the compositions of the present invention include only ingredients that can be employed in food products or in food wash, handling, or processing, for example, according to government (e.g. FDA or USDA) rules and regulations, 21 CFR § 170-178. In an embodiment, the compositions of the present invention can include only ingredients at the concentrations approved for incidental food contact by the USEPA, 40 CFR § 180.940.

The present compositions can take the form of a liquid, solid, gel, paste, unit dose, gel pack, or the like. The present compositions can be supplied in any of a variety of containers or media, such as in a 2 compartment dispenser or as a pre-moistened wipe, towelette, or sponge.

Carrier

The composition of the invention can also include a carrier. The carrier provides a medium which dissolves, suspends, or carries the other components of the composition. For example, the carrier can provide a medium for solubilization, suspension, or production of peroxycarboxylic acid and for forming an equilibrium mixture. The carrier can also function to deliver and wet the antimicrobial composition of the invention on an object. To this end, the carrier can contain any component or components that can facilitate these functions.

In certain embodiments, the carrier includes primarily water which can promote solubility and work as a medium for reaction and equilibrium. The carrier can include or be primarily an organic solvent, such as simple alkyl alcohols, e.g., ethanol, isopropanol, n-propanol, and the like. Polyols are also useful carriers, including glycerol, sorbitol, and the like.

Suitable carriers include glycol ethers. Suitable glycol ethers include diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether (commercially available as DOWANOL EPH™ from Dow Chemical Co.), propylene glycol phenyl ether (commercially available as DOWANOL PPH™ from Dow Chemical Co.), and the like, or mixtures thereof. Additional suitable commercially available glycol ethers (all of which are available from Union Carbide Corp.) include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

In certain embodiments, the carrier makes up a large portion of the composition of the invention and may be the balance of the composition apart from the active antimicrobial components, solubilizer, oxidizing agent, adjuvants, and the like. Here again, the carrier concentration and type will depend upon the nature of the composition as a whole, the environmental storage, and method of application including concentration of the medium chain peroxycarboxylic acid, among other factors. Notably the carrier should be chosen and used at a concentration which does not inhibit the antimicrobial efficacy of the medium chain peroxycarboxylic acid in the composition of the invention.

In certain embodiments, the present composition includes about 0 to about 98 wt-% carrier, about 0.001 to about 99.99 wt-% carrier, about 0.2 to about 60 wt-% carrier, about 1 to about 98 wt-% carrier, about 5 to about 99.99 wt-% carrier, about 5 to about 97 wt-% carrier, about 5 to about 90 wt-% carrier, about 5 to about 70 wt-% carrier, about 5 to about 20 wt-% carrier, about 10 to about 90 wt-% carrier, about 10 to about 80 wt-% carrier, about 10 to about 50 wt-% carrier, about 10 to about 20 wt-% carrier, about 15 to about 70 wt-% carrier, about 15 to about 80 wt-% carrier, about 20 to about 70 wt-% carrier, about 20 to about 50 wt-% carrier, about 20 to about 40 wt-% carrier, about 20 to about 30 wt-% carrier, about 30 to about 75 wt-% carrier, about 30 to about 70 wt-% carrier, about 40 to about 99.99 wt-% carrier, about 40 to about 90 wt-% carrier, or about 60 to about 70 wt-% carrier. The composition can include any of these ranges or amounts not modified by about.

Oxidizing Agent

The present compositions and methods can include any of a variety of oxidizing agents. The oxidizing agent can be used for maintaining or generating peroxycarboxylic acids.

Examples of inorganic oxidizing agents include the following types of compounds or sources of these compounds, or alkali metal salts including these types of compounds, or forming an adduct therewith:

hydrogen peroxide;
group 1 (IA) oxidizing agents, for example lithium peroxide, sodium peroxide, and the like;
group 2 (IIA) oxidizing agents, for example magnesium peroxide, calcium peroxide, strontium peroxide, barium peroxide, and the like;
group 12 (IIB) oxidizing agents, for example zinc peroxide, and the like;
group 13 (IIIA) oxidizing agents, for example boron compounds, such as perborates, for example sodium perborate hexahydrate of the formula $Na_2[Br_2(O_2)_2(OH)_4] \cdot 6H_2O$ (also called sodium perborate tetrahydrate and formerly written as $NaBO_3 \cdot 4H_2O$); sodium peroxyborate tetrahydrate of the formula $Na_2Br_2(O_2)_2[(OH)_4] \cdot 4H_2O$ (also called sodium perborate trihydrate, and formerly written as $NaBO_3 \cdot 3H_2O$); sodium peroxyborate of the formula $Na_2[B_2(O_2)_2(OH)_4]$ (also called sodium perborate monohydrate and formerly written as $NaBO_3 \cdot H_2O$); and the like; in an embodiment, perborate;
group 14 (IVA) oxidizing agents, for example persilicates and peroxycarbonates, which are also called percarbonates, such as persilicates or peroxycarbonates of alkali metals; and the like; in an embodiment, percarbonate; in an embodiment, persilicate;
group 15 (VA) oxidizing agents, for example peroxynitrous acid and its salts; peroxyphosphoric acids and their salts, for example, perphosphates; and the like; in an embodiment, perphosphate;
group 16 (VIA) oxidizing agents, for example peroxysulfuric acids and their salts, such as peroxymonosulfuric and peroxydisulfuric acids, and their salts, such as persulfates, for example, sodium persulfate; and the like; in an embodiment, persulfate;
group VIIa oxidizing agents such as sodium periodate, potassium perchlorate and the like.

Other active inorganic oxygen compounds can include transition metal peroxides; and other such peroxygen compounds, and mixtures thereof.

In an embodiment, the compositions and methods of the present invention employ one or more (e.g., at least one) of the inorganic oxidizing agents listed above. Suitable inorganic oxidizing agents include ozone, hydrogen peroxide, hydrogen peroxide adduct, group IIIA oxidizing agent, group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

Hydrogen peroxide presents one suitable example of an inorganic oxidizing agent. Hydrogen peroxide can be provided as a mixture of hydrogen peroxide and water, e.g., as liquid hydrogen peroxide in an aqueous solution. Hydrogen peroxide is commercially available at concentrations of 35%, 70%, and 90% in water. For safety, the 35% is commonly used. The present compositions can include, for example, about 2 to about 30 wt-% or about 5 to about 20 wt-% hydrogen peroxide.

In an embodiment, the inorganic oxidizing agent includes hydrogen peroxide adduct. For example, the inorganic oxidizing agent can include hydrogen peroxide, hydrogen peroxide adduct, or mixtures thereof. Any of a variety of hydrogen peroxide adducts are suitable for use in the present compositions and methods. For example, suitable hydrogen peroxide adducts include percarbonate salt, urea peroxide, peracetyl borate, an adduct of $H_2O_2$ and polyvinyl pyrrolidone, sodium percarbonate, potassium percarbonate, mixtures thereof, or the like. Suitable hydrogen peroxide adducts include percarbonate salt, urea peroxide, peracetyl borate, an adduct of $H_2O_2$ and polyvinyl pyrrolidone, or mixtures thereof. Suitable hydrogen peroxide adducts include sodium percarbonate, potassium percarbonate, or mixtures thereof, for example sodium percarbonate.

In an embodiment, the present compositions and methods can include hydrogen peroxide as oxidizing agent. Hydrogen peroxide in combination with the percarboxylic acid can provide certain antimicrobial action against microorganisms. Additionally, hydrogen peroxide can provide an effervescent action which can irrigate any surface to which it is applied. Hydrogen peroxide can work with a mechanical flushing action once applied which further cleans the surface of an object. An additional advantage of hydrogen peroxide is the food compatibility of this composition upon use and decomposition.

In certain embodiments, the present composition includes about 0.001 to about 30 wt-% oxidizing agent, about 0.001 to about 10 wt-% oxidizing agent, 0.002 to about 10 wt-% oxidizing agent, about 2 to about 30 wt-% oxidizing agent, about 2 to about 25 wt-% oxidizing agent, about 2 to about 20 wt-% oxidizing agent, about 4 to about 20 wt-% oxidizing agent, about 5 to about 10 wt-% oxidizing agent, or about 6 to about 10 wt-% oxidizing agent. The composition can include any of these ranges or amounts not modified by about.

Acidulant

In an embodiment, the present composition can include an acidulant. The acidulant can act as a catalyst for conversion of carboxylic acid to peroxycarboxylic acid. The acidulant can be effective to form a concentrate composition with pH of about 1 or less. The acidulant can be effective to form a use composition with pH of about 5, about 5 or less, about 4, about 4 or less, about 3, about 3 or less, about 2, about 2 or less, or the like. In an embodiment, the acidulant includes an inorganic acid. Suitable inorganic acids include sulfuric acid, phosphoric acid, nitric acid, hydrochloric acid, methane sulfonic acid, ethane sulfonic acid, propane sulfonic acid, butane sulfonic acid, xylene sulfonic acid, benzene sulfonic acid, mixtures thereof, or the like.

In an embodiment, the acidulant includes a carboxylic acid with $pK_a$ less than 4. Suitable carboxylic acids with $pK_a$ less than 4 include hydroxyacetic acid, hydroxypropionic acid, other hydroxycarboxylic acids, mixtures thereof, or the like. Such an acidulant is present at a concentration where it does not act as a solubilizer.

In certain embodiments, the present composition includes about 0.001 to about 50 wt-% acidulant, about 0.001 to about 30 wt-% acidulant, about 1 to about 50 wt-% acidulant, about 1 to about 30 wt-% acidulant, about 2 to about 40 wt-% acidulant, about 2 to about 10 wt-% acidulant, about 3 to about 40 wt-% acidulant, about 5 to about 40 wt-% acidulant, about 5 to about 25 wt-% acidulant, about 10 to about 40 wt-% acidulant, about 10 to about 30 wt-% acidulant, about 15 to about 35 wt-% acidulant, about 15 to about 30 wt-% acidulant, or about 40 to about 60 wt-% acidulant. The composition can include any of these ranges or amounts not modified by about.

Stabilizing Agent

One or more stabilizing agents can be added to the composition of the invention, for example, to stabilize the peracid and hydrogen peroxide and prevent the premature oxidation of this constituent within the composition of the invention.

Suitable stabilizing agents include chelating agents or sequestrants. Suitable sequestrants include organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, or aminocarboxylic acids.

The sequestrant can be or include phosphonic acid or phosphonate salt. Suitable phosphonic acids and phosphonate salts include 1-hydroxy ethylidene-1,1-diphosphonic acid ($CH_3C(PO_3H_2)_2OH$) (HEDP); ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; or mixtures thereof.

Suitable organic phosphonates include HEDP.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino (tri(methylenephosphonic acid)), ($N[CH_2PO_3H_2]_3$), available from Monsanto as DEQUEST® 2000; ethylenediamine [tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and alanine-N,N-diacetic acid; and the like; and mixtures thereof.

The sequestrant can be or include a polycarboxylate. Suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

In certain embodiments, the present composition includes about 0.5 to about 50 wt-% sequestrant, about 1 to about 50 wt-% sequestrant, about 1 to about 30 wt-% sequestrant, about 1 to about 15 wt-% sequestrant, about 1 to about 5 wt-% sequestrant, about 1 to about 4 wt-% sequestrant, about 2 to about 10 wt-% sequestrant, about 2 to about 5 wt-% sequestrant, or about 5 to about 15 wt-% sequestrant. The composition can include any of these ranges or amounts not modified by about.

In certain embodiments, the present composition includes about 0.001 to about 50 wt-% stabilizing agent, about 0.001 to about 5 wt-% stabilizing agent, about 0.5 to about 50 wt-% stabilizing agent, about 1 to about 50 wt-% stabilizing agent, about 1 to about 30 wt-% stabilizing agent, about 1 to about 10 wt-% stabilizing agent, about 1 to about 5 wt-% stabilizing agent, about 1 to about 3 wt-% stabilizing agent, about 2 to about 10 wt-% stabilizing agent, about 2 to about 5 wt-% stabilizing agent, or about 5 to about 15 wt-% stabilizing agent. The composition can include any of these ranges or amounts not modified by about.

Adjuvants

The antimicrobial composition of the invention can also include any number of adjuvants. Specifically, the composition of the invention can include antimicrobial solvent, antimicrobial agent, wetting agent, defoaming agent, thickener, a surfactant, foaming agent, solidification agent, aesthetic enhancing agent (i.e., colorant (e.g., pigment), odorant, or perfume), among any number of constituents which can be added to the composition. Such adjuvants can be preformulated with the antimicrobial composition of the invention or added to the system simultaneously, or even after, the addition of the antimicrobial composition. The composition of the invention can also contain any number of other constituents as necessitated by the application, which are known and which can facilitate the activity of the present invention.

Antimicrobial Solvent

Any of a variety of solvents can be useful as antimicrobial solvents in the present compositions. Antimicrobial solvent can be added to use compositions before use. Suitable antimicrobial solvents include acetamidophenol; acetanilide; acetophenone; 2-acetyl-1-methylpyrrole; benzyl acetate; benzyl alcohol; benzyl benzoate; benzyloxyethanol; essential oils (e.g., benzaldehyde, pinenes, terpineols, terpinenes, carvone, cinnamealdehyde, borneol and its esters, citrals, ionenes, jasmine oil, limonene, dipentene, linalool and its esters); diester dicarboxylates (e.g., dibasic esters) such as dimethyl adipate, dimethyl succinate, dimethyl glutarate (including products available under the trade designations DBE, DBE-3, DBE-4, DBE-5, DBE-6, DBE-9, DBE-IB, and DBE-ME from DuPont Nylon), dimethyl malonate, diethyl adipate, diethyl succinate, diethyl glutarate, dibutyl succinate, and dibutyl glutarate; dimethyl sebacate, dimethyl pimelate, dimethyl suberate; dialkyl carbonates such as dimethyl carbonate, diethyl carbonate, dipropyl carbonate, diisopropyl carbonate, and dibutyl carbonate; organo-nitriles such as acetonitrile and benzonitrile; and phthalate esters such as dibutyl phthalate, diethylhexyl phthalate, and diethyl phthalate. Mixtures of antimicrobial solvents can be used if desired.

The antimicrobial solvent can be selected based upon the characteristics of the surface and microbes to which the antimicrobial composition will be applied and upon the nature of any coating, soil or other material that will be contacted by the antimicrobial composition and optionally removed from the surface. Polar solvents, and solvents that are capable of hydrogen bonding typically will perform well on a variety of surfaces and microbes and thus, for such applications, can be selected. In certain applications, the antimicrobial solvent can be selected for a high flashpoint (e.g., greater than about 30° C., greater than about 50° C., or greater than about 100° C.), low odor, and low human and animal toxicity.

In an embodiment, the antimicrobial solvent is compatible as an indirect or direct food additive or substance; especially those described in the Code of Federal Regulations (CFR), Title 21—Food and Drugs, parts 170 to 186. The compositions of the invention should contain sufficient antimicrobial solvent to provide the desired rate and type of microbial reduction.

The present composition can include an effective amount of antimicrobial solvent, such as about 0.01 wt-% to about 60 wt-% antimicrobial solvent, about 0.05 wt-% to about 15 wt-% antimicrobial solvent, or about 0.08 wt-% to about 5 wt-% antimicrobial solvent.

Additional Antimicrobial Agent

The antimicrobial compositions of the invention can contain an additional antimicrobial agent. Additional antimicrobial agent can be added to use compositions before use. Suitable antimicrobial agents include carboxylic esters (e.g., p-hydroxy alkyl benzoates and alkyl cinnamates), sulfonic acids (e.g., dodecylbenzene sulfonic acid), iodo-compounds or active halogen compounds (e.g., elemental halogens, halogen oxides (e.g., NaOCl, HOCl, HOBr, $ClO_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and $C_1$-$C_6$ alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection.

The present composition can include an effective amount of antimicrobial agent, such as about 0.001 wt-% to about 60 wt-% antimicrobial agent, about 0.01 wt-% to about 15 wt-% antimicrobial agent, or about 0.08 wt-% to about 2.5 wt-% antimicrobial agent.

Wetting or Defoaming Agents

Also useful in the composition of the invention are wetting and defoaming agents. Wetting agents function to increase the surface contact or penetration activity of the antimicrobial composition of the invention. Wetting agents which can be used in the composition of the invention include any of those constituents known within the art to raise the surface activity of the composition of the invention.

Suitable defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; fatty acid soaps such as alkali, alkaline earth metal soaps; and phosphates and phosphate esters such as alkyl and alkaline diphosphates, and tributyl phosphates among others; and mixtures thereof.

In an embodiment, the present compositions can include antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 5 wt-%, from about 0.01 wt-% to 2 wt-%, or from about 0.01 wt-% to about 1 wt-%.

Thickening or Gelling Agents

The present compositions can include any of a variety of known thickeners. Suitable thickeners include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. In an embodiment, the thickener does not leave contaminating residue on the surface of an object. For example, the thickeners or gelling agents can be compatible with food or other sensitive products in contact areas. Generally, the concentration of thickener employed in the present compositions or methods will be dictated by the desired viscosity within the final composition. However, as a general guideline, the viscosity of thickener within the present composition ranges from about 0.1 wt-% to about 1.5 wt-%, from about 0.1 wt-% to about 1.0 wt-%, or from about 0.1 wt-% to about 0.5 wt-%.

Solidification Agent

The present compositions can include a solidification agent, which can participate in maintaining the compositions in a solid form. Suitable solidification agents include a solid polyethylene glycol (PEG), a solid EO/PO block copolymer, and the like; an amide, such as stearic monoethanolamide, lauric diethanolamide, an alkylamide, or the like; starches that have been made water-soluble through an acid or alkaline treatment process; celluloses that have been made water-soluble; an inorganic agent, or the like; poly(maleic anhydride/methyl vinyl ether); polymethacrylic acid; other generally functional or inert materials with high melting points; and the like.

In certain embodiments, the solidification agent includes solid PEG, for example PEG 1500 up to PEG 20,000. In certain embodiments, the PEG includes PEG 1450, PEG 3350, PEG 4500, PEG 8000, PEG 20,000, and the like. Additional suitable solidification agents include EO/PO block copolymers such as those sold under the tradenames Pluronic 108, Pluronic F68; amides such as lauric diethanolamide or cocodiethylene amide; and the like. In certain embodiments, the solidification agent includes a combination of solidification agents, such as combination of PEG and an EO/PO block copolymer (such as a Pluronic) and combination of PEG and an amide (such as lauric diethanolamide amide or stearic monoethanol amide).

Fragrance

In an embodiment, the present composition includes a fragrance. The fragrance can be selected to avoid undesirable effects on the stability or efficacy of the composition. Suitable fragrances include amyl acetate, iso-bornyl acetate, and alkyl salicylates, such as methyl salicylate. In an embodiment, the fragrance can include an alkylsalicylate.

Use Compositions

The present compositions include concentrate compositions and use compositions. For example, a concentrate composition can be diluted, for example with water, to form a use composition. In an embodiment, a concentrate composition can be diluted to a use solution before to application to an object. For reasons of economics, the concentrate can be marketed and an end user can dilute the concentrate with water or an aqueous diluent to a use solution.

The level of active components in the concentrate composition is dependent on the intended dilution factor and the desired activity of the medium chain peroxycarboxylic acid compound. Generally, a dilution of about 1 fluid ounce to about 20 gallons of water to about 5 fluid ounces to about 1 gallon of water is used for aqueous antimicrobial compositions. Higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 20 ounces of concentrate per 100 gallons of water.

For example, a use composition can include about 0.01 to about 4 wt-% of a concentrate composition and about 96 to about 99.99 wt-% diluent; about 0.5 to about 4 wt-% of a concentrate composition and about 96 to about 99.5 wt-% diluent; about 0.5, about 1, about 1.5, about 2, about 2.5, about 3, about 3.5, or about 4 wt-% of a concentrate composition; about 0.01 to about 0.1 wt-% of a concentrate composition; or about 0.01, about 0.02, about 0.03, about 0.04, about 0.05, about 0.06, about 0.07, about 0.08, about 0.09, or about 0.1 wt-% of a concentrate composition. Amounts of an ingredient in a use composition can be calculated from the amounts listed above for concentrate compositions and these dilution factors.

The present methods can employ medium chain peroxycarboxylic acid at a concentration effective for reducing the population of one or more microorganisms. Such effective concentrations include about 2 to about 500 ppm medium chain peroxycarboxylic acid, about 2 to about 300 ppm medium chain peroxycarboxylic acid, about 5 to about 100 ppm medium chain peroxycarboxylic acid, about 5 to about 60 ppm medium chain peroxycarboxylic acid, about 5 to about 45 ppm medium chain peroxycarboxylic acid, about 5 to about 35 ppm medium chain peroxycarboxylic acid, about 5 to about 25 ppm medium chain peroxycarboxylic acid, about 8 to about 50 ppm medium chain peroxycarboxylic acid, about 10 to about 500 ppm medium chain peroxycarboxylic acid, about 10 to about 50 ppm medium chain peroxycarboxylic acid, about 40 to about 140 ppm medium chain peroxycarboxylic acid, about 100 to about 250 ppm medium chain peroxycarboxylic acid, or about 200 to about 300 ppm medium chain peroxycarboxylic acid. In an embodiment, the use composition can include about 2 to about 500 ppm medium chain peroxycarboxylic acid, about 5 to about 2000 ppm medium chain carboxylic acid, about 95 to about 99.99 wt-% carrier and/or diluent (e.g., water); and about 2 to about 23,000 ppm polyalkylene oxide, capped polyalkylene oxide, alkoxylated surfactant, anionic surfactant, or mixture thereof.

The level of reactive species, such as peroxycarboxylic acids and/or hydrogen peroxide, in a use composition can be affected, typically diminished, by organic matter that is found in or added to the use composition. For example, when the use composition is a bath or spray used for washing an object, soil on the object can consume peroxy acid and peroxide. Thus, the present amounts of ingredients in the use compositions refer to the composition before or early in use, with the understanding that the amounts will diminish as organic matter is added to the use composition.

In an embodiment, the present use composition can be made more acidic by passing the concentrate through an acidifying column, or by adding additional acidulant to the use composition.

Other Fluid Compositions

The present and compositions can include a critical, near critical, or supercritical (densified) fluid and an antimicrobial agent or a gaseous composition of an antimicrobial agent. The densified fluid can be a near critical, critical, supercritical fluid, or another type of fluid with properties of a supercritical fluid. Fluids suitable for densification include carbon dioxide, nitrous oxide, ammonia, xenon, krypton, methane, ethane, ethylene, propane, certain fluoroalkanes (e.g., chlorotrifluoromethane and monofluoromethane), and the like, or mixtures thereof. Suitable fluids include carbon dioxide.

In an embodiment, the present compositions or methods include densified carbon dioxide, medium chain peroxycarboxylic acid, and medium chain carboxylic acid. Such a composition can be referred to as a densified fluid medium chain peroxycarboxylic acid composition. In another embodiment, the antimicrobial composition includes the fluid, an antimicrobial agent, and any of the optional or added ingredients, but is in the form of a gas.

Densified fluid antimicrobial compositions can be applied by any of several methods known to those of skill in the art. Such methods include venting at an object a vessel containing densified fluid and antimicrobial agent. The aqueous phase, which includes hydrogen peroxide, is advantageously retained in the device. The vented gas includes an effective amount of antimicrobial agent making the densified fluid peroxycarboxylic acid compositions effective antimicrobial agents.

Because of the high pressure nature of the densified fluid compositions of the invention, these compositions are typically applied by venting a vessel containing the composition through a pressure relief device that is designed to promote rapid efficient coverage of an object. Devices including such a pressure relief device include sprayers, foggers, foamers, foam pad applicators, brush applicators or any other device that can permit the expansion of the fluid materials from high pressure to ambient pressure while applying the material to an object. The densified fluid peroxycarboxylic acid composition can also be applied to an object by any of a variety of methods known for applying gaseous agents to an object.

Densified fluid antimicrobial compositions can be made by reacting an oxidizable substrate with an oxidizing agent in a medium comprising a densified fluid to form an antimicrobial composition. This reaction is typically carried out in a vessel suitable for containing a densified fluid. Reacting can include adding to the vessel the oxidizable substrate and the oxidizing agent, and adding fluid to the vessel to form the densified fluid. In an embodiment, the reaction is between a medium chain carboxylic acid and hydrogen peroxide to form the corresponding peroxycarboxylic acid. The hydrogen peroxide is commonly supplied in the form of an aqueous solution of hydrogen peroxide.

Supercritical, subcritical, near supercritical, and other dense fluids and solvents that can be employed with such fluids are disclosed in U.S. Pat. No. 5,306,350, issued Apr. 26, 1994 to Hoy et al., which is incorporated by reference herein for such disclosure. Supercritical and other dense forms of carbon dioxide, and cosolvents, co-surfactants, and other additives that can be employed with these forms of carbon dioxide are disclosed in U.S. Pat. No. 5,866,005, issued Feb. 2, 1999 to DeSimone et al., which is incorporated by reference herein for such disclosure.

Making Medium Chain Peroxycarboxylic Acid Compositions

The compositions of or used in the methods of the invention can be made by combining or reacting the medium chain carboxylic acid and the oxidizing agent, such as hydrogen peroxide. Combining or reacting medium chain carboxylic acid and oxidizing agent results in production of medium chain peroxycarboxylic acid. In an embodiment, combining includes mixing. The formulation combined for making the present compositions can also include the solubilizer, the acidulant, the carrier, stabilizing agent, mixtures thereof, or the like. In an embodiment, the formulation includes solubilizer. Alternatively, one or more (e.g., at least one) of the solubilizer, the acidulant, the carrier, or mixtures thereof, can be added after production of some or all of the peroxycarboxylic acid.

In an embodiment, the present invention includes a method of making a medium chain peroxycarboxylic acid. The method can include combining or reacting medium chain carboxylic acid, carrier (e.g., water), oxidizing agent (e.g., hydrogen peroxide), solubilizer, acidulant, and stabilizing agent. The method can include mixing the ingredients at concentrations of about 1 to about 10 wt-% medium chain carboxylic acid, about 0 to about 98 wt-% carrier, about 2 to about 30 wt-% oxidizing agent, about 1 to about 80 wt-% solubilizer, about 1 to about 50 wt-% acidulant, and about 0.5 to about 50 wt-% stabilizing agent. The method can include mixing the ingredients at concentrations about 1 to about 10 wt-% medium chain carboxylic acid, about 5 to about 97 wt-% carrier, about 2 to about 30 wt-% oxidizing agent, about 1 to about 20 wt-% solubilizer (e.g., microemulsion forming surfactant), about 1 to about 50 wt-% acidulant, and about 0.5 to about 50 wt-% stabilizing agent. The present compositions also include compositions in which these combinations of ingredients have come to equilibrium forming medium chain peroxycarboxylic acid.

In an embodiment, the present method produces advantageously high levels of medium chain peroxycarboxylic acid in advantageously short times. Advantageously short times include, for example, about 24 or fewer hours, about 6 or fewer hours, about 3 or fewer hours, or about 0.5 hr. In an embodiment, high levels of medium chain peroxycarboxylic acid can be achieved nearly instantaneously. High levels of medium chain peroxycarboxylic acid be achieved by converting 20% or more, 25% or more, 30% or more, 35% or more, or 40% of the medium chain carboxylic acid to medium chain peroxycarboxylic acid. Such conversions can be achieved at room temperature or in a reaction started at room temperature and warmed by an exotherm. Lower temperatures can require a longer time to reach the same amount of conversion. The amount of time is typically measured from the time that the carboxylic acid, oxidizing agent, solubilizer, and acidulant are combined or reacted.

For example, in an embodiment, the present method can convert 20% or more of the medium chain carboxylic acid to medium chain peroxycarboxylic acid in about 24 or fewer hours. For example, in an embodiment, the present method can convert about 25% or more of the medium chain carboxylic acid to medium chain peroxycarboxylic acid in about 24 or fewer hours. For example, in an embodiment, the present method can convert about 30% or more of the medium chain carboxylic acid to medium chain peroxycarboxylic acid in about 24 or fewer hours. For example, in an embodiment, the present method can convert about 35% or more of the medium chain carboxylic acid to medium chain peroxycarboxylic acid in about 24 or fewer hours. For example, in an embodiment, the present method can convert about 40% of the medium chain carboxylic acid to medium chain peroxycarboxylic acid in about 24 or fewer hours.

In an embodiment, making the present compositions includes forming a microemulsion. A microemulsion can be formed by mixing the desired ingredients including a microemulsion forming surfactant. The method can include combining or mixing the ingredients at concentration of about 1 to about 10 wt-% medium chain carboxylic acid, about 5 to about 97 wt-% carrier (e.g., water), about 2 to about 30 wt-% oxidizing agent, about 1 to about 20 wt-% microemulsion forming surfactant, and about 1 to about 50 wt-% stabilizer. The present compositions also include compositions in which these combinations of ingredients have come to equilibrium forming medium chain peroxycarboxylic acid. The components can be added in any of a variety of orders. In an embodiment, formation of the medium chain peroxy carboxylic acid can proceed rapidly after the addition of the microemulsion forming surfactant. Although not limiting to the present invention, it is believed that the formation of the microemulsion can significantly increase the effective surface area of the medium chain carboxylic acid (as micro-droplets) for reaction.

The present compositions can be made in a plant as a concentrate and shipped to an end user who need only dilute the concentrate to form a use composition. The present medium chain peroxycarboxylic acid compositions can also be made at the site of use. For example, the product can be shipped as a two or more part composition or as a kit. The user can then combine the two or more compositions or components of the kit to produce the present medium chain peroxycarboxylic acid compositions. Alternatively, a system of formulating equipment and containers of raw materials can be provided at the site of use, and programmed or operated to mix and disperse the present medium chain peroxycarboxylic acid compositions.

In an embodiment, the product can be supplied as a two or more part composition. In certain embodiments, one composition can include carboxylic acid and one or more (e.g., at least one) of solubilizer, acidulant, carrier, stabilizing agent, mixtures thereof, or the like. The second composition can include oxidizing agent and one or more (e.g., at least one) of solubilizer, acidulant, carrier, stabilizing agent, mixtures thereof, or the like. Alternatively, the solubilizer, acidulant, carrier, stabilizing agent mixtures thereof, or the like can be supplied as additional composition(s). In certain embodiments, one composition can include carboxylic acid and at least one of oxidizing agent, solubilizer, acidulant, carrier, stabilizing agent, mixtures thereof, and the like. The second composition can include at least one of fragrance, odor counteractant, emollient, other incompatible ingredient, oxidizing agent, solubilizer, acidulant, carrier, stabilizing agent, mixtures thereof, and the like.

In an embodiment, the pH of a concentrate composition can be less than about 1 or about 2. In an embodiment, the pH of a 1% or 1.5% solution of the mixture in water is about 1 or 2 to about 7, depending on the other components of the 1% solution. In an embodiment, the pH of a use composition can be from about 2 to about 7 depending on the other components.

Some examples of representative concentrations of ingredients useful in the present methods of making medium chain peroxycarboxylic acid compositions can be found in Tables G and H, in which the values are given in wt-% of the ingredients in reference to the total composition weight. In certain embodiments, the proportions and amounts in Tables G-H can be modified by "about". The present compositions also include compositions in which these combinations of ingredients have come to equilibrium forming medium chain peroxycarboxylic acid.

TABLE G

| Ingredient | wt-% | wt-% | wt-% | wt-% | wt-% | wt-% | wt-% | wt-% |
|---|---|---|---|---|---|---|---|---|
| medium chain carboxylic acid | 1-10 | 3-8 | 4-6 | 2-8 | 3-6 | 1-10 | 3-8 | 3-6 |
| solubilizer | 1-80 | 2-70 | 3-65 | 5-70 | 10-65 | 1-25 | 3-15 | 4-10 |
| carrier | 0-98 | 5-90 | 10-80 | 0.2-60 | 5-20 | 5-97 | 15-70 | 30-75 |

TABLE H

| Ingredient | wt-% | wt-% | wt-% | wt-% | wt-% | wt-% | wt-% | wt-% |
|---|---|---|---|---|---|---|---|---|
| medium chain carboxylic acid | 1-10 | 3-8 | 4-6 | 2-8 | 3-6 | 1-10 | 3-8 | 3-6 |
| solubilizer | 1-80 | 2-70 | 3-65 | 5-70 | 10-65 | 1-25 | 3-15 | 4-10 |
| carrier | 0-98 | 5-90 | 10-80 | 0.2-60 | 5-20 | 5-97 | 15-70 | 30-75 |
| oxidizing agent | 2-30 | 2-25 | 4-20 | 2-25 | 4-20 | 2-30 | 4-20 | 6-10 |
| acidulant | 1-50 | 2-40 | 3-40 | 2-40 | 3-40 | 1-50 | 3-35 | 5-30 |
| stabilizing agent | 1-50 | 1-10 | 1-5 | 1-10 | 1-5 | 1-50 | 1-5 | 1-3 |

Methods Employing the Medium Chain Peroxycarboxylic Acid Compositions

The present invention includes methods employing the medium chain peroxycarboxylic acid compositions. Typically, these methods employ the antimicrobial or bleaching activity of the peroxycarboxylic acid. For example, the invention includes a method for reducing a microbial population, a method for reducing the population of a microorganism on skin, a method for treating a disease of skin, a method for reducing an odor, or a method for bleaching. These methods can operate on an object, surface, in a body or stream of water or a gas, or the like, by contacting the object, surface, body, or stream with a stabilized ester peroxycarboxylic acid composition of the invention. Contacting can include any of numerous methods for applying a composition, such as spraying the composition, immersing the object in the composition, foam or gel treating the object with the composition, or a combination thereof.

The compositions of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions of the invention can also be applied to soft surfaces such as food and skin (e.g., a hand). The present compositions can be employed as a foaming or nonfoaming environmental sanitizer or disinfectant.

The antimicrobial compositions of the invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The antimicrobial compositions can also be used in veterinary products such as mammalian skin treatments or in products for sanitizing or disinfecting animal enclosures, pens, watering stations, and veterinary treatment areas such as inspection tables and operation rooms. The present compositions can be employed in an antimicrobial foot bath for livestock or people.

The present compositions can be employed for reducing the population of pathogenic microorganisms, such as pathogens of humans, animals, and the like. The compositions can exhibit activity against pathogens including fungi, molds, bacteria, spores, and viruses, for example, *S. aureus, E. coli, Streptococci, Legionella, Pseudomonas aeruginosa*, mycobacteria, tuberculosis, phages, or the like. Such pathogens can cause a varieties of diseases and disorders, including Mastitis or other mammalian milking diseases, tuberculosis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface.

The antimicrobial compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like. Particular foodstuffs that can be treated with compositions of the invention include eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The present composition is useful in the cleaning or sanitizing of containers, processing facilities, or equipment in the food service or food processing industries. The antimicrobial compositions have particular value for use on food packaging materials and equipment, and especially for cold or hot aseptic packaging. Examples of process facilities in which the composition of the invention can be employed include a milk line dairy, a continuous brewing system, food processing lines such as pumpable food systems and beverage lines, etc. Food service wares can be disinfected with the composition of the invention. For example, the compositions can also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The antimicrobial compositions can also be used on or in other industrial equipment and in other industrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like.

A filter containing the composition can reduce the population of microorganisms in air and liquids. Such a filter can remove water and air-born pathogens such as *Legionella*.

The present compositions can be employed for reducing the population of microbes, fruit flies, or other insect larva on a drain or other surface.

The composition may also be employed by dipping food processing equipment into the use solution, soaking the equipment for a time sufficient to sanitize the equipment, and wiping or draining excess solution off the equipment, The composition may be further employed by spraying or wiping food processing surfaces with the use solution, keeping the surfaces wet for a time sufficient to sanitize the surfaces, and removing excess solution by wiping, draining vertically, vacuuming, etc.

The composition of the invention may also be used in a method of sanitizing hard surfaces such as institutional type equipment, utensils, dishes, health care equipment or tools, and other hard surfaces. The composition may also be employed in sanitizing clothing items or fabric which have become contaminated. The use solution is contacted with any of the above contaminated surfaces or items at use temperatures in the range of about 4° C. to 60° C., for a period of time effective to sanitize, disinfect, or sterilize the surface or item. For example, the concentrate composition can be injected into the wash or rinse water of a laundry machine and contacted with contaminated fabric for a time sufficient to sanitize the fabric. Excess solution can then be removed by rinsing or centrifuging the fabric.

The antimicrobial compositions can be applied to microbes or to soiled or cleaned surfaces using a variety of methods. These methods can operate on an object, surface, in a body or stream of water or a gas, or the like, by contacting the object, surface, body, or stream with a composition of the invention. Contacting can include any of numerous methods for applying a composition, such as spraying the composition, immersing the object in the composition, foam or gel treating the object with the composition, or a combination thereof.

A concentrate or use concentration of a composition of the present invention can be applied to or brought into contact with an object by any conventional method or apparatus for applying an antimicrobial or cleaning composition to an object. For example, the object can be wiped with, sprayed with, foamed on, and/or immersed in the composition, or a use solution made from the composition. The composition can be sprayed, foamed, or wiped onto a surface; the composition can be caused to flow over the surface, or the surface can be dipped into the composition. Contacting can be manual or by machine. Food processing surfaces, food products, food processing or transport waters, and the like can be treated with liquid, foam, gel, aerosol, gas, wax, solid, or powdered stabilized compositions according to the invention, or solutions containing these compositions.

Additional methods employing the present compositions can be found in U.S. patent application Ser. Nos. 10/754,396, 10/754,436, and 10/754,405 each filed Jan. 9, 2004; and in U.S. patent applications Ser. No.11/030,271 entitled METHODS FOR WASHING POULTRY DURING PROCESSING WITH MEDIUM CHAIN PEROXYCARBOXYLIC ACID COMPOSITIONS; No. 11/029,235 entitled METHODS FOR WASHING CARCASSES, MEAT, OR MEAT PRODUCTS WITH MEDIUM CHAIN PEROXYCARBOXYLIC ACID COMPOSITIONS; and No. 11/030,233 entitled METHODS FOR WASHING AND PROCESSING FRUITS, VEGETABLES, AND OTHER PRODUCE WITH MEDIUM CHAIN PEROXYCARBOXYLIC ACID COMPOSITIONS; each of which was filed evendate herewith; each of which is incorporated herein by reference.

Clean in Place

Other hard surface cleaning applications for the antimicrobial compositions of the invention include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like.

Generally, the actual cleaning of the in-place system or other surface (i.e., removal of unwanted offal therein) is accomplished with a different material such as a formulated detergent which is introduced with heated water. After this cleaning step, the instant composition would be applied or introduced into the system at a use solution concentration in unheated, ambient temperature water. CIP typically employ flow rates on the order of about 40 to about 600 liters per minute, temperatures from ambient up to about 70° C., and contact times of at least about 10 seconds, for example, about 30 to about 120 seconds. The present composition can remain in solution in cold (e.g., 40° F./4° C.) water and heated (e.g., 140° F./60° C.) water. Although it is not normally necessary to heat the aqueous use solution of the present composition, under some circumstances heating may be desirable to further enhance its antimicrobial activity. These materials are useful at any conceivable temperatures.

A method of sanitizing substantially fixed in-place process facilities includes the following steps. The use solution of the invention is introduced into the process facilities at a temperature in the range of about 4° C. to 60° C. After introduction of the use solution, the solution is held in a container or circulated throughout the system for a time sufficient to sanitize the process facilities (i.e., to kill undesirable microorganisms). After the surfaces have been sanitized by means of the present composition, the use solution is drained. Upon completion of the sanitizing step, the system optionally may be rinsed with other materials such as potable water. The composition can be circulated through the process facilities for 10 minutes or less.

The present method can include delivering the present composition via air delivery to the clean-in-place or other surfaces such as those inside pipes and tanks. This method of air delivery can reduce the volume of solution required.

Contacting a Food Product with the Medium Chain Peroxycarboxylic Acid Composition The present method and system provide for contacting a food product with a medium chain composition employing any method or apparatus suitable for applying such a composition. For example, the method and system of the invention can contact the food product with a spray of the composition, by immersion in the composition, by foam or gel treating with the composition, or the like. Contact with a spray, a foam, a gel, or by immersion can be accomplished by a variety of methods known to those of skill in the art for applying antimicrobial agents to food. Contacting the food product can occur in any location in which the food product might be found, such as field, processing site or plant, vehicle, warehouse, store, restaurant, or home. These same methods can also be adapted to apply the stabilized compositions of the invention to other objects.

The present methods require a certain minimal contact time of the composition with food product for occurrence of significant antimicrobial effect. The contact time can vary with concentration of the use composition, method of applying the use composition, temperature of the use composition, amount of soil on the food product, number of microorganisms on the food product, type of antimicrobial agent, or the like. The exposure time can be at least about 5 to about 15 seconds.

In an embodiment, the method for washing food product employs a pressure spray including the composition. During application of the spray solution on the food product, the surface of the food product can be moved with mechanical action, e.g., agitated, rubbed, brushed, etc. Agitation can be by physical scrubbing of the food product, through the action of the spray solution under pressure, through sonication, or by other methods. Agitation increases the efficacy of the spray solution in killing micro-organisms, perhaps due to better exposure of the solution into the crevasses or small colonies containing the micro-organisms. The spray solution, before application, can also be heated to a temperature of about 15 to 20° C., for example, about 20 to 60° C. to increase efficacy. The spray stabilized composition can be left on the food product for a sufficient amount of time to suitably reduce the population of microorganisms, and then rinsed, drained, or evaporated off the food product.

Application of the material by spray can be accomplished using a manual spray wand application, an automatic spray of food product moving along a production line using multiple spray heads to ensure complete contact, or other spray apparatus. One automatic spray application involves the use of a spray booth. The spray booth substantially confines the sprayed composition to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the stabilized compositions of the invention. These steam jets can be used in combination with cooling water to ensure that the treatment reaching the food product surface is less than 65° C., e.g., less than 60° C. The temperature of the spray on the food product is important to ensure that the food product is not substantially altered (cooked) by the temperature of the spray. The spray pattern can be virtually any useful spray pattern.

Immersing a food product in a liquid stabilized composition can be accomplished by any of a variety of methods known to those of skill in the art. For example, the food product can be placed into a tank or bath containing the stabilized composition. Alternatively, the food product can be transported or processed in a flume of the stabilized composition. The washing solution can be agitated to increase the efficacy of the solution and the speed at which the solution reduces micro-organisms accompanying the food product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the food product has been immersed for a time sufficient for the desired antimicrobial effect, the food product can be removed from the bath or flume and the stabilized composition can be rinsed, drained, or evaporated off the food product.

In another alternative embodiment of the present invention, the food product can be treated with a foaming version of the composition. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides. The foaming surfactant is typically mixed at time of use with the washing solution. Use solution levels of the foaming agents is from about 50 ppm to about 2.0 wt-%. At time of use, compressed air can be injected into the mixture, then applied to the food product surface through a foam application device such as a tank roamer or an aspirated wall mounted roamer.

In another alternative embodiment of the present invention, the food product can be treated with a thickened or gelled version of the composition. In the thickened or gelled state the washing solution remains in contact with the food product surface for longer periods of time, thus increasing the antimicrobial efficacy. The thickened or gelled solution will also adhere to vertical surfaces. The composition or the washing solution can be thickened or gelled using existing technologies such as: xanthan gum, polymeric thickeners, cellulose thickeners, or the like. Rod micelle forming systems such as amine oxides and anionic counter ions could also be used. The thickeners or gel forming agents can be used either in the concentrated product or mixing with the washing solution, at time of use. Typical use levels of thickeners or gel agents range from about 100 ppm to about 10 wt-%.

Aseptic Packaging

In the method of the present invention, aseptic packaging includes contacting the container with a composition according to the present invention. Such contacting can be accomplished using a spray device or soaking tank or vessel to intimately contact the inside of the container with the composition for sufficient period of time to clean or reduce the microbial population in the container. The container is then emptied of the amount of the present composition used. After emptying, the container can then be rinsed with potable water or sterilized water (which can include a rinse additive) and again emptied. After rinsing, the container can be filled with the liquid beverage. The container is then sealed, capped or closed and then packed for shipment for ultimate sale.

The Figure shows a schematic for an embodiment of a bottle spraying/bottling operation using a composition according to the present invention. The operation can be a cold aseptic operation. The Figure shows a plant 100 that can contact beverage bottles with a medium chain peroxycarboxylic acid composition for a sanitizing regime. In the Figure, bottles 110 are passed through a sterilizing tunnel 102. The sanitized bottles 110*a* then pass through a rinsing tunnel 103 and emerge as sanitized rinsed bottles 110*b*.

In the process, bulk medium chain peroxycarboxylic acid composition is added to a holding tank 101. Commonly, the materials are maintained at a temperature of about 22° C. in tank 101. To obtain the effective use concentration of the medium chain peroxycarboxylic acid composition, make-up water 105 is combined with the concentrated medium chain peroxycarboxylic acid composition into the tank 101. The medium chain peroxycarboxylic acid use composition is passed through a heater 108 to reach a temperature of about 45-50° C. The heated medium chain peroxycarboxylic acid use composition is sprayed within sterilizing tunnel 102 into and onto all surfaces of the bottle 110. An intimate contact between the medium chain peroxycarboxylic acid composition and the bottle 110 is essential for reducing microbial populations to a sanitizing level.

After contact with the medium chain peroxycarboxylic acid use composition and after dumping any excess composition from the bottles, the sanitized bottles 110 are then passed to a fresh water rinse tunnel 103. Fresh water 108 is provided from a fresh water make-up into a spray rinsing tunnel 103. The fresh water can include a rinse additive. Excess spray drains from rinsing tunnel 103 to drain 106. Within the tunnel 103, sanitized bottles 110*a* are thoroughly rinsed with fresh water. The complete removal of the medium chain peroxycarboxylic acid composition from the bottles 110*a* is important for maintaining high quality of the beverage product. The rinsed and sanitized bottles 110*b* are then removed from the rinsing tunnel.

The day tank 101, the sterilizing tunnel 102 and the rinsing tunnel 103 are all respectively vended to wet scrubber or vent 111*a*, 111*b* or 111*c* to remove vapor or fumes from the system components. The sanitizer material that has been sprayed and drained from the bottles 110*a* accumulate in the bottom of the spray tunnel 102 and is then recycled through recycle line and heater 107 into the day tank 101.

The contact between the bottles and the medium chain peroxycarboxylic acid antimicrobial composition can be at a temperature of greater than about 0° C., greater than 25° C., or greater than about 40° C. Temperatures between about 40° C. and 90° C. can be used. In certain embodiments, contact at 40° C. to 60° C. for at least 5 sec, for example at least about 10 sec, contact time is employed.

In the cold aseptic filling of 16 ounce polyethylene terephthalate (PET bottle), or other polymeric, beverage containers, a process has been adopted using a medium chain peroxycarboxylic acid composition. The medium chain peroxycarboxylic acid composition can be diluted to a use concentration of about 0.1 to about 10 wt % and maintained at an effective elevated temperature of about 25° C. to about 70° C., e.g., about 40° C. to about 60° C. The spray or flood of the bottle with the material ensures contact between the bottle and the sanitizer material for at least 5, e.g., about 10, seconds. After flooding is complete, the bottle can be drained of all contents for a minimum of 2 seconds and optionally followed by a 5 second water rinse with sterilized water using about 200 milliliters of water at 38° C. (100° F.). If optionally filled with the rinse water, the bottle is then drained of the sterilized water rinse for at least 2 seconds and is immediately filled with liquid beverage. The rinse water can include a rinse additive. After the rinse is complete, the bottles usually maintain less than 10, e.g., 3, milliliters of rinse water after draining.

The present invention may be better understood with reference to the following examples. These examples are intended to be representative of specific embodiments of the invention, and are not intended as limiting the scope of the invention.

EXAMPLES

Example 1

Compositions Including Medium Chain Peroxycarboxylic Acid and Solubilizer

Tables 1-5 present illustrative examples of the present compositions including medium chain peroxycarboxylic acid and solubilizer. Quantities in the tables are in wt-%.

TABLE 1

Examples of Compositions Including Solvent Solubilizer

| Ingredient | A | B | C | D | E |
|---|---|---|---|---|---|
| Medium Chain Peroxycarboxylic Acid | 1.8 | 1.6 | 1.4 | 1.6 | 2.9 |
| Medium Chain Carboxylic Acid | 3.4 | 3.6 | 3.7 | 3.6 | 2.4 |
| Solubilizer | 60 | 40 | 60 | 60 | 40 |
| Carrier | 25 | 22 | 25 | 22 | 22 |
| Oxidizing Agent | 7.0 | 6.6 | 7.0 | 6.9 | 6.9 |
| Acidulant | 2 | 25 | 2 | 5 | 25 |
| Stabilizing Agent | 1.2 | 1.2 | 1.2 | 1.2 | 1.2 |

In each of compositions A-Q: the medium chain peroxycarboxylic acid was peroxyoctanoic acid; the medium chain carboxylic acid was octanoic acid; the carrier was water; the oxidizing agent was hydrogen peroxide (supplied from a 35% solution); and the stabilizing agent was HEDP (supplied as Dequest 2010 which includes 60 wt-% HEDP).

In each of compositions A-L, 0, P, and Q: the acidulant was concentrated sulfuric acid. In compositions M and N, the acidulant was phosphoric acid (supplied as 85% and 75% phosphoric acid, respectively).

The solubilizer was varied among these compositions. In compositions A and B, the solubilizer was polyethyleneglycol 300. In compositions C, D, and E, the solubilizer was monomethyl ether of polyethyleneglycol (MPEG 550). In composition F, the solubilizer was nonionic surfactant, specifically Pluronic 17R[4] an $(PO)_x(EO)_y(PO)_x$ reverse triblock copolymer with 40% EO and 60% PO. In composition G, the solubilizer was polyethyleneglycol 300 plus LAS acid (98% linear dodecylbenzene sulfonic acid). In composition H, the solubilizer was polyethyleneglycol 300 plus 1-octane sulfonate (supplied under the tradename NAS-FAL as 38% active). In composition I, the solubilizer was polyethyleneglycol 300 plus Dowfax Hydrotrope acid ($C_6$ alkylated diphenyl oxide disulfonic acid). In composition J, the solubilizer was dimethyl ether of polyethyleneglycol (PolyDME250) and LAS acid. In composition K, the solubilizer was dimethyl ether of polyethyleneglycol (PolyDME250) and NAS-FAL. In composition L, the solubilizer was dimethyl ether of polyethyleneglycol (PolyDME250) and Dowfax Hydrotrope acid. In compositions M, N, O and P, the solubilizer was dimethyl ether of polyethyleneglycol (PolyDME250) and NAS-FAL. In composition Q, the solubilizer was dimethyl ether of polyethyleneglycol (PolyDME250) and NAS acid (supplied as 93% 1-octane sulfonic acid).

These compositions were made from a composition including 5 wt-% medium chain carboxylic acid.

In each of compositions R-Z: the medium chain peroxycarboxylic acid was peroxyoctanoic acid; the medium chain carboxylic acid was octanoic acid; the carrier was water; the oxidizing agent was hydrogen peroxide (supplied from a 35% solution); and the stabilizing agent was HEDP (supplied as Dequest 2010 which includes 60 wt-% HEDP).

In compositions R and S, the acidulant was phosphoric acid (supplied as 75% phosphoric acid). In each of compositions T, U, and V, the acidulant was reagent grade, 98%, concentrated sulfuric acid (15 wt-%) and phosphoric acid (23 wt-%) (supplied as 75% phosphoric acid). In compositions W, X, Y, and Z, the acidulant was concentrated sulfuric acid (25 wt-%) and phosphoric acid (14 wt-%) (supplied as 75% phosphoric acid).

TABLE 2

Examples of Compositions Including Solvent Solubilizer and Surfactant Solubilizer

| Ingredient | F | G | H | I | J | K | L | M | N | O | P | Q |
|---|---|---|---|---|---|---|---|---|---|---|---|---|
| Medium Chain Peroxycarboxylic Acid | 0.8 | 0.7 | 1.1 | 1.1 | 0.9 | 2.1 | 1.6 | 0.7 | 0.9 | 5.0 | not measured | 5.0 |
| Medium Chain Carboxylic Acid | 4.3 | 4.4 | 4.0 | 4.0 | 4.2 | 4.2 | 3.1 | 4.4 | 4.2 | 0.2 | <5 | 0.2 |
| Solvent Solubilizer | 0 | 40 | 40 | 40 | 42 | 44 | 42 | 34 | 29 | 28 | 28 | 28 |
| Surfactant Solubilizer | 45 | 5 | 2 | 5 | 8 | 6 | 7 | 6 | 4 | 6 | 6 | 10 |
| Carrier | 37 | 30 | 33 | 30 | 29 | 21 | 24 | 26 | 28 | 28 | 26 | 24 |
| Oxidizing Agent | 7.0 | 6.9 | 6.8 | 6.9 | 6.1 | 6.4 | 6.5 | 6.7 | 6.5 | 6.9 | 8.7 | 6.9 |
| Acidulant | 5 | 7 | 7 | 7 | 8 | 15 | 15 | 21 | 26 | 25 | 25 | 25 |
| Stabilizing Agent | 1.2 | 6 | 6 | 6 | 1.2 | 1.2 | 1.2 | 1.2 | 1.2 | 1.2 | 1.2 | 1.2 |

TABLE 3

Examples of Compositions Including Surfactant Solubilizer

| Ingredient | R | S | T | U | V | W | X | Y | Z |
|---|---|---|---|---|---|---|---|---|---|
| Medium Chain Peroxycarboxylic Acid | 0.5 | 0.4 | 1.0 | 1.0 | 0.7 | 3.8 | 3.7 | 3.8 | 3.5 |
| Medium Chain Carboxylic Acid | 4.6 | 4.6 | 3.1 | 3.1 | 3.4 | 2.6 | 2.7 | 2.6 | 2.9 |
| Surfactant Solubilizer | 17 | 20 | 20 | 20 | 20 | 20 | 20 | 20 | 20 |
| Carrier | 32 | 29 | 27 | 27 | 27 | 24 | 24 | 24 | 24 |
| Oxidizing Agent | 8.0 | 8.3 | 9.2 | 9.2 | 9.3 | 8.6 | 8.7 | 8.6 | 8.7 |
| Acidulant | 36 | 36 | 38 | 38 | 38 | 39 | 39 | 39 | 39 |
| Stabilizing Agent | 2.4 | 2.4 | 2.4 | 2.4 | 2.4 | 2.4 | 2.4 | 2.4 | 2.4 |

TABLE 4

Examples of Compositions Including Anionic Surfactant and/or Microemulsion Solubilizer

| Ingredient | AA | AA-O | BB | CC | DD | EE | FF | GG | HH | II | JJ | KK |
|---|---|---|---|---|---|---|---|---|---|---|---|---|
| Medium Chain Peroxycarboxylic Acid | 1.5 | 2.0 | 1.2 | 1.4 | 1.3 | 1.4 | 1.1 | 1.0 | 1.2 | 1.0 | 1.1 | 1.3 |
| Medium Chain Carboxylic Acid | 3.6 | 2.7 | 2.9 | 2.5 | 2.6 | 2.5 | 2.8 | 2.9 | 2.9 | 3.1 | 3.0 | 2.6 |
| Solubilizer | 8 | 5 | 5 | 9 | 4 | 4 | 6 | 4 | 5 | 5 | 5 | 4 |
| Carrier | 41 | 45 | 69 | 52 | 59 | 60 | 62 | 56 | 67 | 67 | 67 | 55 |
| Oxidizing Agent | 7.7 | 7.4 | 6.3 | 7.8 | 8.0 | 7.6 | 7.9 | 8.0 | 7.8 | 7.3 | 7.8 | 8.1 |
| Acidulant | 36 | 36 | 14 | 25 | 23 | 23 | 18 | 26 | 14 | 15 | 14 | 27 |
| Stabilizing Agent | 2.4 | 2.4 | 1.8 | 2.3 | 2.3 | 2.3 | 2.3 | 2.3 | 1.8 | 1.8 | 1.8 | 2.0 |

| Ingredient | LL | MM | NN | OO | PP | QQ | RR | SS | TT | UU | VV |
|---|---|---|---|---|---|---|---|---|---|---|---|
| Medium Chain Peroxycarboxylic Acid | 1.4 | 1.1 | 1.5 | not determined | 0.9 | 0.5 | 0.54 | 3.4 | 0.2 | 1.0 | 0.4 |
| Medium Chain Carboxylic Acid | 2.5 | 2.7 | 2.3 | <3.8 | 3.1 | 3.3 | 3.3 | 0.5 | 3.6 | 2.8 | 3.4 |

TABLE 4-continued

Examples of Compositions Including Anionic Surfactant and/or Microemulsion Solubilizer

| Solubilizer | 4 | 4 | 4 | 5 | 1 | 2 | 4 | 10 | 6 | 10 | 22 |
|---|---|---|---|---|---|---|---|---|---|---|---|
| Carrier | 56 | 57 | 57 | 40-50 | 60 | 59 | 58 | 53 | 54 | 51 | 39 |
| Oxidizing Agent | 7.8 | 6.9 | 6.5 | <8 | 7.1 | 7.5 | 7.5 | 5.6 | 7.8 | 8.0 | 7.7 |
| Acidulant | 26 | 26 | 26 | 26 | 26 | 26 | 26 | 26 | 1.8 | 1.8 | 1.8 |
| Stabilizing Agent | 2.3 | 2.3 | 2.3 | 2.3 | 2.3 | 2.3 | 2.3 | 2.3 | 27 | 27 | 27 |

The solubilizer was varied among these compositions. In composition R, the solubilizer was 1-octane sulfonate (1.9 wt-%) and Tegotens EC-11 (a butoxy capped alcohol ethoxylate, a fast wetting surfactant) (15 wt-%). In compositions S, T, and W the solubilizer was Tegotens EC-11. In compositions U and Y, the solubilizer was Dehypon LS-54 $(R(EO)_5(PO)_4$, a fast wetting surfactant). In compositions V and Z, the solubilizer was Dehypon LT-104 (a butyl capped alcohol ethoxylate). In composition X, the solubilizer was LF-221 (a butoxy capped alcohol ethoxylate).

In each of compositions AA-VV: the medium chain peroxycarboxylic acid was peroxyoctanoic acid; the medium chain carboxylic acid was octanoic acid; the carrier was water; the oxidizing agent was hydrogen peroxide (supplied as 35% hydrogen peroxide in water); and the stabilizing agent was HEDP (supplied as Dequest 2010, which includes 60 wt-% HEDP).

In each of compositions AA, AA-0, DD, EE, GG, KK, LL, MM, NN, OO, PP, QQ, RR, SS, TT, UU, and VV the acidulant was phosphoric acid (supplied as 75% phosphoric acid). In composition BB, HH the acidulant was concentrated sulfuric acid (reagent grade, 98%). In composition CC, the acidulant was methane sulfonic acid (99.5%+Aldrich). In composition FF, the acidulant was nitric acid (supplied as 70% nitric acid). In composition II, the acidulant was concentrated sulfuric acid (technical grade, 93%). In composition JJ, the acidulant was sulfuric acid (supplied as 50% sulfuric acid).

The solubilizer was varied among these compositions. In compositions AA, AA-0, BB, CC, DD, FF, LL, HH, II, and JJ, the solubilizer was 1-octane sulfonate. In compositions EE and GG, the solubilizer was 1-octane sulfonate (3.8 wt-%) and Dehypon LS-54 (0.2 wt-%). In composition KK, the solubilizer was 1-octane sulfonate (NAS-FAL). In composition MM, the solubilizer was 1-octane sulfonate (3.8 wt-%) and Barlox 12 (dodecyldimethyl amine oxide, 30% active) (0.25 wt-%). In composition NN, the solubilizer was 1-octane sulfonate (3.8 wt-%) and Barlox 12 (0.5 wt-%). In composition OO, the solubilizer was 1-octane sulfonate (3.8 wt-%) and Barlox 12 (1 wt-%). In compositions PP, QQ, RR, and SS, the solubilizer was LAS-acid. In composition TT, the solubilizer was disodium cocoampho dipropionate (supplied under the tradename Miranol® FBS, which includes 39% solids). In composition UU, the solubilizer was an aminoproprionate betaine (supplied under the tradename Mirataine® JC-HA, which includes 42% solids). In composition VV, the solubilizer C12-13 alcohol 4 mole EO carboxylic acid (supplied under the tradename Neodox 23-4, which includes 90% active).

The quantities of medium chain peroxycarboxylic acid were determined in compositions PP, QQ, RR, and SS after 7.5 days at 60° C.

TABLE 5

Examples of Compositions Including Anionic Surfactant and/or Microemulsion Solubilizer plus Strong Organic Acidulant

| Ingredient | WW | XX | YY | ZZ | BA |
|---|---|---|---|---|---|
| Medium Chain Peroxycarboxylic Acid | 1.5 | 1.3 | 0.5 | 0.5 | 0.8 |
| Medium Chain Carboxylic Acid | 2.5 | 2.7 | 3.5 | 3.5 | 3.2 |
| Solubilizer | 4 | 4 | 4 | 4 | 4 |
| Carrier | 58 | 58 | 56 | 57 | 71 |
| Oxidizing Agent | 7.7 | 7.6 | 7.7 | 8.1 | 8.2 |
| Acidulant | 24 | 24 | 26 | 25 | 11 |
| Stabilizing Agent | 1.8 | 1.8 | 1.8 | 1.8 | 1.8 |

In each of compositions WW, XX, YY, ZZ, and BA: the medium chain peroxycarboxylic acid was peroxyoctanoic acid; the medium chain carboxylic acid was octanoic acid; the carrier was water; the oxidizing agent was hydrogen peroxide (supplied as 35% hydrogen peroxide in water); the stabilizing agent was HEDP (supplied as Dequest 2010, which includes 60 wt-% HEDP); and the solubilizer was NAS-FAL.

The acidulant was varied among these compositions. In composition WW, the acidulant was hydroxyacetic acid (supplied as 75% hydroxyacetic acid) (19 wt-%) and sulfuric acid (reagent grade, 98%) (5 wt-%). In composition XX, the acidulant was hydroxyacetic acid (supplied as 75% hydroxyacetic acid) (19 wt-%) and methane sulfonic acid (99.5%+Aldrich) (5 wt-%). In composition YY, the acidulant was hydroxyacetic acid (supplied as 75% hydroxyacetic acid). In composition ZZ, the acidulant was purified hydroxyacetic acid. In composition BA, the acidulant was hydroxypropionic acid (supplied as 22% 3-hydroxypropionic acid).

In these compositions the hydroxycarboxylic acids contributed virtually no solubilization of the medium chain carboxylic acid. The compositions required solubilizer.

Making the Exemplified Compositions

TABLE 6

Generation of Peroxyoctanoic Acid with Time at Room Temperature and at 120° F. (Composition KK)

| Minutes at RT | [POOA] wt-% | Minutes at 120° F. | [POOA] wt-% |
|---|---|---|---|
| 11 | 0.61 | 30 | 1.46 |
| 53 | 1.09 | 45 | 1.38 |
| 97 | 1.11 | 60 | 1.23 |
| 130 | 1.1 | 90 | 1.47 |
| 235 | 1.24 | 120 | 1.31 |
| 293 | 1.27 | | |
| 330 | 1.46 | | |
| 366 | 1.39 | | |
| 395 | 1.5 | | |

When a high level of sulfuric acid was used as the acidulant (Examples include B, E, O, and Q), a strong exotherm was obtained, and the medium chain peroxy carboxylic acid was generated rapidly, for example, virtually instantaneously. For some of these compositions, the sulfuric acid needed to be added slowly and with cooling to keep the temperature below 170° F. or below 120° F. Such formulas that can generate medium chain peroxy carboxylic acids, rapidly or almost instantaneously can be employed for on site generation at the use location.

The concentrations of peroxyoctanoic acid reported in the present examples were determined by a well established and standardized titration protocol. First, hydrogen peroxide content was determined by an oxidation-reduction titration with ceric sulfate. After the endpoint of this titration was reached, an excess of potassium iodide was added to the solution. The potassium iodide reacts with peroxycarboxylic acids to liberate iodine. The liberated iodine was titrated with a standard solution of sodium thiosulfate to yield the concentration of peroxycarboxylic acid. The remaining level of carboxylic acid can be calculated.

The octanoic acid employed in the present examples was obtained from sources including Procter & Gamble Chemicals and includes a minimum of 95% octanoic acid with minor amounts of hexanoic acid (ca. 2%), decanoic acid (ca. 2%), and dodecanoic acid (<0.5%).

Example 2

Stability of Compositions Including Medium Chain Peroxycarboxylic Acid and Solubilizer Compositions according to the present invention were evaluated and demonstrated physical stability and advantageous stability of the medium chain peroxycarboxylic acid.

Materials and Methods

Several of the present medium chain peroxycarboxylic acid compositions were evaluated for stability of the medium chain peroxycarboxylic acid. A sealed container including the composition was placed in an oven at an elevated temperature or was left at room temperature for a period of time. The temperatures and times are reported in the tables below. One week at 60° C. can be considered equivalent to a year at room temperature (RT). The quantity of peroxycarboxylic acid was determined by titration.

Several of the present medium chain peroxycarboxylic acid compositions were also evaluated for physical stability. The sample were visually inspected at intervals at which peroxycarboxylic acid level was also determined.

Results

The results obtained for determinations of stability of the medium chain peroxycarboxylic acid and of physical stability are reported below in Tables 7 and 8.

The results presented in Table 7 for compositions M and N indicate that stability of the medium chain peroxycarboxylic acid decreases when phosphoric acid increases from 25% to 35%. This suggests that the compositions including solvent solubilizer are susceptible to degradation caused by impurities present in the technical grade phosphoric acid.

The results presented in Table 8, specifically the blue tyndall appearance, indicates that each of these compositions was in the form of a microemulsion.

A study of accelerated aging of a mixed peroxycarboxylic acid composition demonstrated that peroxyoctanoic acid in a mixed peracid composition underwent significant degradation at 60° C. in 7 days. After 7 days, three samples underwent 20, 23, and 54% degradation.

TABLE 7

Advantageous Stability of Medium Chain Peroxycarboxylic Acid in the Present Compositions Including Solvent Solubilizer

| Composition | Starting [POOA] (wt-%) | Days at 100° F. | Wt-% Remaining, 100° F. | Days at RT | Wt-% Remaining, RT |
|---|---|---|---|---|---|
| A | 1.8 (after 1 day at 100° F.) | 22 | 1 | 46 | 2.3 |
| B | 1.6 | 37 | 0.8 | 37 | 2.1 |
| C | 1.4 | 36 | 0.9 | 36 | 1.3 |
| D | 1.6 | 36 | 0.7 | 36 | 1.4 |
| E | 2.9 | 36 | 0.4 | 36 | 1.8 |
| F | 0.8 | 31 | 1.1 | 31 | 0.9 |
| J | 0.9 (after 3 days at RT) | 33 | 1.2 | 13 | 1.2 |
| K | 2.1 (after 3 days at RT) | 33 | 1.1 | 17 | 2.0 |
| L | 1.6 (after 3 days at RT) | 22 | 1.2 | 13 | 1.5 |
| M | 0.7 | 28 | 1 | 8 | 1.1 |
| N | 0.9 | 28 | 0.7 | 7 | 1.4 |

The microemulsion compositions were less susceptible to degradation by impurities. For example, compositions KK and LL included technical grade phosphoric acid and exhibited good stability. In contrast, if phosphoric acid is to be used in conventional formulations of peroxycarboxylic acids, high purity grade is required to avoid unacceptable degradation.

Compositions A, B, C, D, and E were two phase compositions.

TABLE 8

Stability of Compositions Including Anionic Surfactant and/or Microemulsion Solubilizer

| Composition | Starting [POOA] (wt-%) | Days at 60° C. | Wt-% Remaining | Appearance |
|---|---|---|---|---|
| LL | 1.4 (after 1 day at 60° C.) | 7 | 1.4 | 1 phase, hazy blue tyndall |
| HH | 1.2 (after 3 days at 60° C.) | 7 | 1.2 | Blue tyndall gel with no bubbles in solution. Slightly hazy. |
| KK | 1.3 | 7 | 1.3 | 1 phase, hazy blue tyndall |

Example 3

Shear Thinning Viscosity of Compositions Including Medium Chain Peroxycarboxylic Acid and Solubilizer Compositions according to the present invention were evaluated and demonstrated to have advantageous shear thinning viscosity, which is characteristic of microemulsions.

Materials and Methods

Several of the present medium chain peroxycarboxylic acid compositions were evaluated for viscosity as a function of rate of spindle rotation using an LVT viscometer and an N2 spindle. The temperature of the compositions was room temperature (about 75° F.).

Results

The results obtained for determinations of viscosity of the present compositions are reported below in Table 7. Decreasing viscosity with increasing spindle rotation rate indicates shear thinning, which is characteristic of a microemulsion. Each of the compositions tested showed shear thinning viscosity.

TABLE 9

Shear Thinning Viscosity of Composition LL

| rpm | Viscosity (cp) | rpm | Viscosity (cp) |
|---|---|---|---|
| 0.6 | 3875 | 2 | 2260 |
| 1.5 | 2600 | 2.5 | 1952 |
| 3 | 1700 | 4 | 1380 |
| 6 | 1300 | 5 | 1208 |
| 12 | 863 | 10 | 736 |
| 30 | 483 | 20 | 468 |
| 60 | 308 | 50 | 280 |
|  |  | 100 | 204 |

TABLE 10

Shear Thinning Viscosity of Composition HH

| rpm | Viscosity (cp) | rpm | Viscosity (cp) |
|---|---|---|---|
| 0.6 | 7000 | 2 | 3500 |
| 1.5 | 3500 | 2.5 | 2848 |
| 3 | 2200 | 4 | 1950 |
| 6 | 1500 | 5 | 1648 |
| 12 | 950 | 10 | 976 |
| 30 | 515 | 20 | 600 |
| 60 | 315 | 50 | 324 |
|  |  | 100 | 212 |

TABLE 11

Shear Thinning Viscosity of Composition KK

| rpm | Viscosity (cp) |
|---|---|
| 0.5 | 4080 |
| 1 | 3120 |
| 2 | 2240 |
| 2.5 | 2016 |
| 4 | 1570 |
| 5 | 1344 |
| 10 | 820 |
| 20 | 520 |
| 50 | 320 |
| 100 | 218 |

Conclusions

The shear thinning viscosity of the present compositions is characteristic of a structured composition, such as a microemulsion.

Example 4

Antimicrobial Efficacy of the Present Compositions Including Medium Chain Peroxycarboxylic Acid and Solubilizer Compositions according to the present invention were evaluated and demonstrated advantageous antimicrobial activity against microbes such as gram negative bacteria, gram positive bacteria, fungi, spores, viruses, and mycobacteria.

Materials and Methods

Antimicrobial activity was determined according to two well established methods. The first method was the procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). The second method was the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). Briefly, antimicrobial activity of the present compositions was determined by exposing a one mL aliquot containing the target microorganism to 99 mL of the desired concentration of the test substance at the desired temperature. After the specified contact time, one mL of the test solution containing the microorganism was neutralized and enumerated for survivors.

The hospital disinfectant efficacy of the present compositions was determined by drying the target microorganism oh a stainless steel carrier and exposing the carrier to 10 mL of the desired concentration of test composition at the desired temperature for the specified contact time. Then, the carrier was aseptically transferred to a neutralizer/subculture medium.

Antiviral activity against Herpes Simplex Virus Type 1 was determined by known procedures. Briefly: Herpes Simplex Virus Type 1 was dried on a glass surface. The film of virus was exposed to test substance for 10 min at room temperature. Then, the mixture of film and test substance were subjected to gel filtration to separate small molecules from virus particles. The recovered virus was assayed for infectivity by an accepted assay method.

Antiviral activity against Poliovirus Type 1 was determined by known procedures. Briefly: Poliovirus Type 1 was dried on a glass surface. The film of virus was exposed to test substance for 5 min at room temperature. Then, the mixture of film and test substance were subjected to gel filtration to separate small molecules from virus particles. The recovered virus was assayed for infectivity by an accepted assay method.

Results

Tables 12-21 include data showing that the present medium chain peroxycarboxylic acid compositions had antimicrobial activity when tested against bacteria, fungi, and spores in several different types of tests.

The data presented in Table 12 demonstrate that the present compositions exhibited significant antimicrobial activity when diluted with a diluent to pH less than 4. Efficacy was not as great if the composition was diluted and then the pH was brought to less than or equal to 4. These results illustrate that present compositions with significant levels of acidulant exhibited, under certain circumstances, advantageous activity.

The data presented in Table 13 demonstrate that the present compositions exhibited significant antimicrobial activity at pH of 2.6 to 3.5. These results indicate that at a pH of 6.1, 11 ppm of peroxyoctanoic acid (POOA) is still effective at reducing *S. aureus* by >7.04 log. The data presented in Table 14 demonstrate that efficacy of this composition was not as great against *E. coli* if it was diluted and then the pH was brought to less than 4.

The data presented in Table 15 demonstrate that the present compositions exhibited significant antimicrobial activity. All formulas tested achieved >5 log reductions of *Escherichia coli* in 30 seconds at 0.069% when diluted in 500 ppm synthetic hard water. Also, these compositions achieved complete kill (>7 log reduction) of *Pseudomonas aeruginosa* in 30 seconds at 0.082% when diluted in 500 ppm synthetic hard water. The combination of higher pH and lower ppm in one composition may have contributed to the lower log reduction.

The data presented in Table 16 demonstrate that the present compositions exhibited significant antimicrobial activity against several fungi and bacteria. The present compositions exhibited broad spectrum antimicrobial activity against bacteria and fungi at low levels of medium chain peroxycarboxylic acid. These results indicate that composition 106 is more effective that composition DD. Composition BB achieved higher reductions of *A. niger* and *P. aeruginosa* at similar levels of peroxycarboxylic acid.

The data presented in Table 17 demonstrate that the present compositions exhibited significant antimicrobial activity against several fungi and several bacteria.

The data presented in Table 18 demonstrate that one of the present compositions (KK) exhibited significant antimicrobial activity against *E. coli* O157:H7, *S. typhimurium*, and *L. monocytogenes*. This composition achieved more than 99.999% reduction within a 30 second exposure time.

The data presented in Table 19 demonstrate that the present compositions exhibited significant antimicrobial activity against several bacteria in a hospital disinfectant test. The hospital disinfectant test measures whether the composition killed all of the microbes on a stainless steel carrier. A composition listed as 10/10 killed all of the bacteria on each of 10 carriers. Likewise a result of 60/60 indicates that a composition kills all of the bacteria on each of 60 carriers. These results present a greater challenge for an antimicrobial agent because it requires activity in the presence of 5% fetal bovine serum. Therefore, it indicates that the present compositions were effective as a hospital disinfectant in the presence of blood soil.

The data presented in Table 20 demonstrate that one of the present compositions exhibited superior antimicrobial activity against several bacteria in a hospital disinfectant test compared to a conventional, commercially available antimicrobial agent. The hospital disinfectant test measures whether the composition killed all of the microbes on a particular carrier. The composition according to the present invention, AA-O, passed the hospital disinfectant test, with complete kill on 59 of 60 carriers. The conventional antimicrobial agent (containing hydrogen peroxide as active) did not pass the test. It yielded complete kill on only 58 of 60 carriers. These results indicate that in the presence of fetal bovine serum and when diluted in synthetic hard water the current composition was more effective than the commercially available hospital disinfectant.

The data presented in Table 21 demonstrate that the present compositions exhibited significant antimicrobial activity against bacterial spores. Bacterial spores are difficult to kill. These results indicate that at elevated temperatures the effectiveness of the present compositions increased, which provided for effective kill at reduced contact times.

The data presented in Table 22 demonstrate that the present compositions exhibited superior antimicrobial activity against bacterial spores compared to conventional peroxide and peroxycarboxylic acid antimicrobials. The present composition resulted in greater kill at equal or lower concentrations of antimicrobial active. These results indicate that the present compositions exhibited superior antimicrobial activity compared to conventional antimicrobials.

The data presented in Table 23 demonstrate that the present compositions exhibited effective antimicrobial activity against *Mycobacterium bovis*. The present composition (B) provided complete kill of *M. bovis* BCG at dilutions of 1 oz per 4 gal and 1 oz per 6 gal with exposure times as short as 6 min. These results indicate that the compositions of the present invention can be employed as a tuberculocidal agent.

Tests against Herpes Simplex Virus Type 1 resulted in complete kill of this virus. The virus was dried onto a hard surface. The virus on the hard surface was contacted for 10 min with composition B diluted at 1 oz per 6 gallons or 1 oz per 8 gallons. Both dilutions resulted in complete kill, a greater than 5.3 log reduction in virus. Virus and cells survived in appropriate controls. These results indicate that the present compositions are effective virucides.

Tests against Poliovirus Type 1 resulted in nearly complete kill of this virus. The virus was dried onto a hard surface. The virus on the hard surface was contacted for 10 min with composition LL diluted at 1 oz per 1 gallon or 1 oz per 0.5 gallons. The dilution of 1 oz to 1 gallon completely killed the poliovirus at 5 different titers, killed no virus at the highest titer, and resulted in incomplete kill at the second and third highest titers. This dilution exhibited 1.5 log reduction in virus titer. The dilution of 1 oz to 0.5 gallons completely killed poliovirus at all titers tested. This dilution resulted in >4 log reduction in virus titer. Virus and cells survived in appropriate controls. These results indicate that the present compositions are effective general virucides.

The data presented in Table 24 demonstrate that the present compositions exhibited antimicrobial activity superior to that of compositions including synthetic medium chain peroxycarboxylic acid that had been added to a composition. Better efficacy was found in the solutions with the lower pH, which were made up with Milli-Q water. The 60 ppm sample almost achieved a 5 log reduction in 30 seconds. However, this data indicates that the pH of the test solution can be more important than the ppm of active POOA.

The data presented in Table 25 demonstrate that the present compositions exhibited antimicrobial activity superior to that of compositions including synthetic medium chain peroxycarboxylic acid that had been added to a composition. These data further suggest that POOA exhibited greater activity against *Escherichia coli* a pH of 4.0 and a concentration >5 ppm no matter what diluent is used. Against *Staphylococcus aureus* POOA achieved 5 log reductions at a concentration of 5 ppm and at a pH of ~5. There was no difference between the reductions seen in Milli-Q water and soft water for either organism.

TABLE 12

Antimicrobial Activity of Compositions Including Solvent Solubilizer Against *E. coli* and *S. aureus* with 30 Second Exposure at Room Temperature

| Composition | [POOA] (ppm) | Diluent | pH | Log Reduction of *E. coli* | Log Reduction of *S. aureus* |
|---|---|---|---|---|---|
| F stored at RT for 31 days 0.92% POOA | 5 | HW - pH 5.0 | 3.19 | 2.45 | 6.10 |
| | | HW - pH 7.8 | 7.74 | 0.10 | 3.52 |
| | | HW - adjusted to pH 4.0 after dosing | 3.98 | 0.10 | 5.62 |
| | 8 | HW - pH 5.0 | 3.03 | 7.15 | >6.70 |
| | | HW - pH 7.8 | 6.16 | 0.07 | 5.62 |
| | | HW - adjusted to pH 4.0 after dosing | 4.00 | 0.65 | >6.40 |
| | 12 | HW - pH 5.0 | 2.86 | >7.15 | >6.70 |
| | | HW - pH 7.8 | 4.41 | 0.59 | 6.70 |
| | | HW - adjusted to pH 4.0 after dosing | 3.96 | 2.84 | 6.40 |
| F stored at 100° F. for 31 days 1.13% POOA | 7 | HW - pH 5.0 | 3.19 | 1.39 | 5.80 |
| | | HW - pH 7.8 | 6.80 | 0.15 | 2.09 |
| | | HW - adjusted to pH 4.0 after dosing | 3.89 | 0.15 | 5.24 |
| | 10 | HW - pH 5.0 | 3.01 | >6.84 | 6.70 |
| | | HW - pH 7.8 | 6.14 | 0.10 | 5.24 |
| | | HW - adjusted to pH 4.0 after dosing | 3.89 | 0.39 | 5.49 |
| | 14 | HW - pH 5.0 | 2.85 | >7.15 | >6.70 |
| | | HW - pH 7.8 | 4.28 | 0.28 | >6.40 |
| | | HW - adjusted to pH 4.0 after dosing | 4.07 | 1.40 | 6.22 |

HW = 500 ppm synthetic hard water

TABLE 13

Antimicrobial Activity of Compositions Including Solvent Solubilizer Against *E. coli* and *S. aureus* with a 30 Second Exposures at Room Temperature - Tests Conducted Using pH Adjusted Synthetic Hard Water

| Composition | pH of Diluent | pH of Test Substance | Log Reduction of *E. coli* | Log Reduction of *S. aureus* |
|---|---|---|---|---|
| K (0.086 wt-%) 16 ppm POOA | 3.9-4.0 | 2.64 | >7.11 | >7.04 |
| | 4.9-5.1 | 2.74 | >7.11 | >7.04 |
| | 5.9-6.1 | 2.75 | >7.11 | >7.04 |
| | 7.7-7.9 | 3.50 | >7.11 | >7.04 |
| K (0.057 wt-%) 11 ppm POOA | 3.9-4.0 | 2.80 | >7.11 | >7.04 |
| | 4.9-5.1 | 2.83 | >7.11 | >7.04 |
| | 5.9-6.1 | 2.97 | >7.11 | >7.04 |
| | 7.7-7.9 | 6.12 | 0.21 | >7.04 |

TABLE 14

Antimicrobial Activity of Compositions Including Solvent Solubilizer Against *E. coli* and *S. aureus* with 30 Second Exposure at Room Temperature - Tests Conducted With pH is Adjustment After Dosing

| Composition | Natural pH | Adjusted pH | Log Reduction of *E. coli* | Log Reduction of *S. aureus* |
|---|---|---|---|---|
| K (0.050 wt-%) | 5.09 | 3.91* | 2.84 | >6.84 |
| K (0.057 wt-%) | 4.92 | 3.85** | 4.61 | >6.84 |

*2 drops of 1.0 N HCl
**5 drops of 1.0 N HCl

TABLE 15

Antimicrobial Activity of Compositions Including Anionic Surfactant and/or Microemulsion Solubilizer Against *Pseudomonas aeruginosa* and *Escherichia coli* with 30 Second Exposure at Room Temperature to a Composition Made with 500 ppm Synthetic Hard Water at pH 7.60

| Composition | Use-Solution [POOA] ppm | pH | Log Reduction of *E. coli* | Log Reduction of *P. aeruginosa* |
|---|---|---|---|---|
| T | 13 | 2.9 | 5.16* | Not Tested |
| U | 13 | 3.1 | >7.28 | |
| V | 12 | 3.0 | >7.28 | |
| T | 16 | 2.8 | Not tested | >7.15 |
| U | 16 | 2.8 | | >7.15 |
| V | 15 | 2.9 | | 4.75 |

*= Duplicate plate counts were not consistent

TABLE 16

Antimicrobial Activity of Compositions Including Anionic Surfactant and/or Microemulsion Solubilizer Against Several Fungi and *Pseudomonas aeruginosa* with a 30 Second Exposure at Room Temperature

| Composition | [POOA] (ppm) | Log Kill of *S. cerevisiae*, (30 sec, RT) | Log Kill of *C. albicans*, (30 sec, RT) | Log Kill of *A. niger*, (5 min, RT) | Log Kill of *P. aeruginosa* (30 sec, RT) |
|---|---|---|---|---|---|
| BB | 22 | >5.6 | >6.1 | 1.6 | |
| | 20 | 5.1 | >6.1 | 1.4 | |
| | 18 | 4.7 | >6.1 | 1.2 | >7.2 |
| | 17 | | | | >7.2 |
| | 16 | | | | >7.2 |
| | 15 | 4.1 | 4.2 | 1.0 | >7.2 |
| | 14 | | | | >7.2 |
| | 13 | | | | 4.7 |
| DD | 16 | | | 0 | 5.6 |
| | 15 | | | 0 | 3.5 |
| | 14 | | | 0 | 1.8 |
| | 13 | | | 0 | 0.73 |

TABLE 17

Antimicrobial Activity of Compositions Including Anionic Surfactant and/or Microemulsion Solubilizer Against Several Fungi and Several Bacteria with a 30 Second Exposure at Room Temperature

| Composition | [POOA] (ppm) | Log Kill of *S. cerevisiae*, (30 sec, RT) | Log Kill of *C. albicans*, (30 sec, RT) | Log Kill of *A. niger*, (5 min, RT) | Log Kill of *P. aeruginosa* (30 sec, RT) | Log Kill of *E. coli* O157:H7 (30 sec, RT) | Log Kill of *L. monocytogenes* (30 sec, RT) | Log Kill of *S. aureus* (30 sec, RT) |
|---|---|---|---|---|---|---|---|---|
| LL | 34 | >5.6 | >6.1 | 3.0 | | | | |
|  | 30 | >5.6 | >6.1 | 2.3 | | | | |
|  | 27 | >5.6 | >6.1 | 1.7 | | | | |
|  | 23 | 4.6 | >6.1 | 1.4 | 5 | >7 | >7 | |
|  | 21 | | | | | >7 | >7 | |
| HH | 26 | >5.4 | >5.8 | 3.4 | | | | |
|  | 21 | 4.2 | >5.8 | 2.2 | | | | |
|  | 17 | 4.1 | >5.8 | 1.4 | >7.0 | >7* | >7.0 | 6.4 |
|  | 16 | | | | >7.0 | >7* | >7.0 | 4.5 |

*also killed a less virulent strain of *E. coli*;

TABLE 18

Antimicrobial Activity of Composition Including Anionic Surfactant and/or Microemulsion Solubilizer Against Several Bacteria 30 and 60 Second Exposure at Room Temperature

| Composition | [POOA] (ppm) | Log Kill of *E. coli* O157: H7, (30 and 60 sec, RT) | Log Kill of *S. typhimurium*, (30 and 60 sec, RT) | Log Kill of *L. monocytogenes*, (30 and 60 sec, RT) |
|---|---|---|---|---|
| KK | 17 | >6.9 | >7.2 | >6.6 |

TABLE 19

Antimicrobial Activity of Compositions Including Anionic Surfactant and/or Microemulsion Solubilizer Against Several Bacteria in a Hospital Disinfectant Test

| Composition | [POOA] (ppm) | *P. aeruginosa* (kill tubes/total tubes) | *S. aureus* (methicillin resistant) (kill tubes/total tubes) | *E. faecalis* (vancomycin resistant) (kill tubes/total tubes) |
|---|---|---|---|---|
| BB | 130 | 60/60 | | |
|  | 89 | 59/60 | | |
|  | 59 | 60/60 | 10/10 | 10/10 |
|  | 44 | 58/60 | 10/10 | 10/10 |
| DD | 140 | 60/60 | | |
|  | 93 | 60/60 | | |
|  | 62 | 60/60 | | |
|  | 47 | 58/60 | | |
| LL | 91 | | 10/10 | 10/10 |
|  | 68 | | 10/10 | 10/10 |

TABLE 20

Antimicrobial Activity of Composition Including Anionic Surfactant and/or Microemulsion Solubilizer and of Conventional Antimicrobial Composition Against Several Bacteria in a Hospital Disinfectant Test

| Composition | [POOA] (ppm) | *P. aeruginosa* (kill tubes/total tubes) | *S. aureus* (kill tubes/total tubes) |
|---|---|---|---|
| AA-O (0.98 wt-%) | 196 | 60/60 | 59/60 |
| Virox 5 (1:16 dilution) | 0 | 58/60 | 58/60 |

TABLE 21

Antimicrobial Activity of Compositions Including Anionic Surfactant and/or Microemulsion Solubilizer Against Bacterial Spores

| Composition | [POOA] (ppm) | Log Kill of *Bacillus cereus* spores (30 sec at 40° C.) | Log Kill of *Bacillus cereus* spores (10 sec at 60° C.) |
|---|---|---|---|
| BB | 200 | 2.1 | 4.7 |
|  | 150 | 0.21 | 2.0 |
| HH | 240 | 4.2 | 5.6 |
|  | 180 | 0.94 | 2.6 |
| DD | 200 | 4.5 | 6.0 |
|  | 150 | 0.53 | 4.1 |
| LL | 290 | 4.7 | 5.7 |
|  | 220 | 0.88 | 4.3 |

TABLE 22

Antimicrobial Activity of Compositions Including Anionic Surfactant and/or Microemulsion Solubilizer and of Conventional Compositions Against Bacterial Spores

| Composition | Concentration of Antimicrobial | pH | Exposure Temperature (° C.) | Exposure Time (sec) | Log Reduction |
|---|---|---|---|---|---|
| $H_2O_2$ | 35% | 3.32 | 40 | 30 | 1.19 |
| | | | | 60 | 2.94 |
| | | | | 120 | >6.30 |
| | | | 60 | 10 | 1.59 |
| | | | | 20 | 4.85 |
| | | | | 30 | 4.89 |
| | | | 80 | 10 | >6.30 |
| | | | | 20 | >6.30 |
| | | | | 30 | >6.30 |
| KK (2.0 wt-%) | 250 ppm POOA | 1.85 | 40 | 30 | 2.33 |
| | 1400 ppm $H_2O_2$ | | | 60 | 6.30 |
| | 520 ppm OA | | | 120 | >6.30 |
| | | | 60 | 10 | 5.30 |
| | | | | 20 | >6.30 |
| | | | | 30 | >6.30 |
| | | | 80 | 10 | >6.30 |
| | | | | 20 | >6.30 |
| | | | | 30 | >6.30 |
| Conventional Mixed Peroxycarboxylic Acid (1.5 wt-%) | 750 ppm peracid 1000 ppm $H_2O_2$ 555 ppm OA | 3.06 | 40 | 30 | 1.02 |
| | | | | 60 | 2.80 |
| | | | | 120 | 4.22 |
| | | | 60 | 10 | 3.96 |
| | | | | 20 | 5.22 |
| | | | | 30 | >6.30 |
| | | | 80 | 10 | >6.30 |
| | | | | 20 | >6.30 |
| | | | | 30 | >6.30 |
| Conventional Peroxyacetic Acid (4.5 wt-%) | 2610 ppm POAA 1.26% H2O2 | 2.61 | 40 | 30 | 0.30 |
| | | | | 60 | 0.30 |
| | | | | 120 | 0.75 |
| | | | 60 | 10 | 0.58 |
| | | | | 20 | 1.85 |
| | | | | 30 | 2.64 |
| | | | 80 | 10 | 4.70 |
| | | | | 20 | >6.30 |
| | | | | 30 | >6.30 |

TABLE 23

Antimicrobial Activity of Compositions Including Solvent Solubilizer Against Mycobacteria

| Composition | [POOA] (ppm) | Exposure Time at Room Temperature (min) | Log Kill of M. bovis |
|---|---|---|---|
| B | 39 | 5 | >6.5 |
| | | 10 | >6.5 |
| | | 15 | >6.5 |
| | | 20 | >6.5 |
| B | 26 | 5 | 6.2 |
| | | 10 | 6.2 |
| | | 15 | >6.5 |
| | | 20 | >6.5 |

TABLE 24

Antimicrobial Activity of Compositions Including POOA from Pure Crystals at 60, 40 and 20 ppm in Milli-Q and Synthetic Hard Water

| Test Substance | Concentration | Diluent | pH | Log Reduction of E. coli |
|---|---|---|---|---|
| Pure POOA Crystals | 60 ppm | 500 ppm Synthetic Hard Water, pH 7.77 | 7.54 | 1.12 |
| | 40 ppm | | 7.61 | 0.93 |
| | 20 ppm | | 7.68 | 0.62 |
| | 60 ppm | Milli-Q water | 5.08 | 4.68 |
| | 40 ppm | | 5.28 | 2.61 |
| | 20 ppm | | 5.58 | 0.55 |

TABLE 25

Antimicrobial Activity of Compositions Including of POOA from Pure Crystals in Milli-Q and Soft Water at Differing pH Values Against Two Bacteria with a 30 Second Exposure at Room Temperature

| Test Substance | Concentration | Diluent | Post Test pH | Log Reduction of E. coli | Log Reduction of S. aureus |
|---|---|---|---|---|---|
| Pure POOA Crystals | 5 ppm | Milli-Q water pH 6.60 | 6.24 | 0.09 | 6.04 |
| | | Milli-Q water pH 5.98 | 5.89 | 0.11 | 4.44 |
| | | Milli-Q water pH 5.00 | 5.03 | 0.07 | 5.01 |
| | | Milli-Q water pH 4.04 | 4.09 | 1.34 | 6.28 |
| | | Soft water pH 9.29 | 9.12 | 0.07 | 0.1 |
| | | Soft water pH 5.91* | 6.68 | 0.08 | 4.19 |
| | | Soft water pH 5.08* | 5.79 | 0.09 | 5.16 |
| | | Soft water pH 3.91 | 4.01 | 1.26 | 5.82 |
| | 10 ppm | Milli-Q water pH 6.60 | 5.80 | 0.06 | >6.82 |
| | | Milli-Q water pH 5.98 | 5.90 | 0.1 | 6.52 |
| | | Milli-Q water pH 5.00 | 4.98 | 0.07 | >6.82 |
| | | Milli-Q water pH 4.04 | 4.08 | 6.04 | >6.82 |
| | | Soft water pH 9.29 | 9.09 | 0.07 | 0.26 |
| | | Soft water pH 5.91 | 6.68 | 0.24 | >6.82 |
| | | Soft water pH 5.08 | 5.67 | 0.55 | 6.12 |
| | | Soft water pH 3.91 | 4.01 | 6.34 | 6.28 |

*Indicates a pH drift of ~0.7 pH units during the 5 hours the test was performed.

Example 5

Compositions Including Medium Chain Peroxycarboxylic Acid and Solubilizer

Table 26 presents additional illustrative examples of the present compositions including medium chain peroxycarboxylic acid and solubilizer. Quantities in the tables are in wt-%.

In each of compositions AB-AQ: the medium chain peroxycarboxylic acid was peroxyoctanoic acid; the medium chain carboxylic acid was octanoic acid; the carrier was water; the oxidizing agent was hydrogen peroxide (supplied from a 35% solution); the stabilizing agent was HEDP (supplied as Dequest 2010 which includes 60 wt-% HEDP); and the acidulant was phosphoric acid (supplied as 75% phosphoric acid). Composition AC included fragrance (1 wt-%), specifically a mint apple fragrance.

The solubilizer was varied among these compositions. In each of compositions AB-AD, AH, AI, AN, the solubilizer was LAS acid. In compositions AE and AJ, the solubilizer was LAS acid plus C8 amine oxide. In composition AF, the solubilizer was LAS acid plus n-octyl amine. In composition AG, the solubilizer was LAS acid plus C8-dimethyl amine. In composition AK, the solubilizer was LAS acid plus alkylated diphenyl oxide disulfonate (acid form). In composition AL, the solubilizer was alkylated diphenyl oxide disulfonate (acid form). In composition AM, the solubilizer was LAS acid plus alkylated diphenyl oxide disulfonate (acid form) and C8 amine oxide. In composition AO, the solubilizer was sodium laureth sulfate; suitable sodium laureth sulfates tested include those with n=1 and 3. In composition AP, the solubilizer was alkylated diphenyl oxide disulfonate (salt form). In composition AQ, the solubilizer was alkylated diphenyl oxide disulfonate (salt form) plus NAS-FAL.

In each of compositions AR-AW: the carrier was water; the oxidizing agent was hydrogen peroxide (supplied from a 35% solution); the stabilizing agent was HEDP (supplied as Dequest 2010 which includes 60 wt-% HEDP); the acidulant was phosphoric acid (supplied as 75% phosphoric acid), and the solubilizer was LAS acid.

The medium chain peroxycarboxylic acid and medium chain carboxylic acid were varied among these compositions. In composition AR, the medium chain peroxycarboxylic acid was peroxynonanoic acid and the medium chain carboxylic acid was nonanoic acid (straight chain nonanoic acid). In compositions AS-AW, the medium chain

TABLE 26

Examples of Compositions Including Surfactant Solubilizer (quantities in wt-%)

| Ingredient | AB | AC | AD | AE | AF | AG | AH | AI | AJ | AK | AL | AM | AN |
|---|---|---|---|---|---|---|---|---|---|---|---|---|---|
| Medium Chain Peroxycarboxylic Acid | 1.0 | 1.1 | 3.1 | 1.2 | 1.5 | 0.9 | 1.2 | 1.1 | nd | 0.9 | 0.9 | nd | 0.9 |
| Medium Chain Carboxylic Acid | 2.8 | 2.7 | 2.0 | 2.6 | 2.3 | 2.9 | 2.6 | 2.7 | <3.8 | 2.9 | 2.9 | <3.8 | 2.6 |
| Solubilizer | 7.8 | 9.7 | 11 | 8.2 | 7.9 | 7.9 | 7 | 6.5 | 8-12 | 5.7 | 6.3 | 8.6 | 7.8 |
| Carrier | 52 | 51 | 34 | 52 | 52 | 52 | 53 | 53 | 48-52 | 54 | 54 | 52 | 52 |
| Oxidizing Agent | 8.0 | 8.1 | 11 | 8.1 | 8.2 | 8.1 | 8.0 | 8.1 | 8 | 8.1 | 8.1 | 8 | 7.9 |
| Acidulant | 27 | 27 | 36 | 27 | 27 | 27 | 27 | 27 | 27 | 27 | 27 | 27 | 27 |
| Stabilizing Agent | 2.0 | 2.0 | 2.7 | 2.0 | 2.0 | 2.0 | 2.0 | 2.0 | 2.0 | 2.0 | 2.0 | 2.0 | 2.0 |

TABLE 26-continued

Examples of Compositions Including Surfactant Solubilizer

| Ingredient | AO | AP | AQ | AR | AS | AT | AU | AV | AW | AX | AY | AZ | BC |
|---|---|---|---|---|---|---|---|---|---|---|---|---|---|
| Medium Chain Peroxycarboxylic Acid | 1.0 | 0.9 | 0.9 | 1.0 | nd | nd | 1.0 | 1.0 | nd | nd | nd | 0.7 | 0.7 |
| Medium Chain Carboxylic Acid | 2.8 | 2.9 | 2.9 | 2.8 | <4.3 | <4.8 | 2.9 | 3.0 | <3.8 | <3.8 | <3.8 | 3.1 | 3.1 |
| Solubilizer | 8-9 | 4.5 | 4.3 | 7.8 | 7.8 | 7.8 | 7.8 | 7.8 | 8 | 8.3 | 8.6 | 7.4 | 7.8 |
| Carrier | 52 | 56 | 56 | 52 | 52 | 52 | 52 | 52 | 52 | 52 | 52 | 53 | 52 |
| Oxidizing Agent | 8.1 | 8.2 | 8.2 | 8.0 | 8 | 8 | 8.2 | 8.2 | 8 | 8 | 8 | 8.2 | 8.2 |
| Acidulant | 27 | 27 | 27 | 27 | 27 | 27 | 27 | 27 | 27 | 27 | 27 | 27 | 27 |
| Stabilizing Agent | 2.0 | 2.0 | 2.0 | 2.0 | 2.0 | 2.0 | 2.0 | 2.0 | 2.0 | 2.0 | 2.0 | 2.0 | 2.0 |

Examples of Compositions Including Surfactant Solubilizer

| Ingredient | BD | BE | BF | BG | BH | BI | BJ | BK |
|---|---|---|---|---|---|---|---|---|
| Medium Chain Peroxycarboxylic Acid | 1.0 | 1.0 | 1.0 | 0.9 | 0.9 | 1.0 | 1.0 | 1.1 |
| Medium Chain Carboxylic Acid | 2.8 | 2.8 | 2.9 | 2.9 | 2.9 | 2.8 | 2.8 | 2.7 |
| Solubilizer | 12 | 10 | 9 | 10 | 13 | 15 | 14 | 16 |
| Carrier | 48 | 50 | 51 | 50 | 47 | 45 | 46 | 44 |
| Oxidizing Agent | 7.8 | 8.2 | 7.6 | 8.3 | 8.3 | 8.3 | 8.2 | 8.1 |
| Acidulant | 27 | 27 | 27 | 14 | 14 | 14 | 14 | 14 |
| Stabilizing Agent | 2.0 | 2.0 | 2.0 | 2.0 | 2.0 | 2.0 | 2.0 | 2.0 | peroxycarboxylic acid was peroxyoctanoic acid and peroxynonanoic acid and the medium chain carboxylic acid was octanoic acid and nonanoic acid; nonanoic acid (as isononanoic acid (which is believed to be a 6 carbon main chain with three pendant methyl groups)) was present at 0.5, 1, 0.1, 0.2, and 0.3 wt-% for AS-AW, respectively.

In each of compositions AX-AZ and BC-BF: the medium chain peroxycarboxylic acid was peroxyoctanoic acid; the medium chain carboxylic acid was octanoic acid; the carrier was water; the oxidizing agent was hydrogen peroxide (supplied from a 35% solution); the stabilizing agent was HEDP (supplied as Dequest 2010 which includes 60 wt-% HEDP); and the acidulant was phosphoric acid (supplied as 75% phosphoric acid).

The solubilizer was varied among these compositions. In composition AX, the solubilizer was LAS acid plus sodium lauryl sulfate. In composition AY, the solubilizer was LAS acid plus sodium lauryl sulfate and C8 dimethyl amine. In compositions AZ and BC-BF, the solubilizer was secondary alkane sulfonate (a mixture of sulfonated paraffins sold under the tradename Hostapur SAS).

In each of compositions BG-BK: the medium chain peroxycarboxylic acid was peroxyoctanoic acid; the medium chain carboxylic acid was octanoic acid; the carrier was water; the oxidizing agent was hydrogen peroxide (supplied from a 35% solution); the stabilizing agent was HEDP (supplied as Dequest 2010 which includes 60 wt-% HEDP); the solubilizer was secondary alkane sulfonate (a mixture of sulfonated paraffins sold under the tradename Hostapur SAS) plus NAS-FAL; and the acidulant was sulfuric acid.

The compositions that included LAS, secondary alkane sulfonate, alkylated diphenyl oxide disulfonate, or sodium lauryl sulfate as solubilizer were foaming compositions. Specifically, compositions AB and AC are foaming compositions.

Most of the compositions were phase stable. In particular: Compositions AX and AY were determined to be phase stable at 60° C. The phase stable compositions including anionic surfactant (e.g., foaming compositions) exhibited blue tyndall appearance and viscoelasticity. They were microemulsions. In fact, only the compositions for which the wt-% of medium chain peroxycarboxylic acid was not determined (nd) were not phase stable. That is, they separated into more than one phase after a predetermined time at one or more (e.g., at least one) of 40° F., room temperature, 100° F., or 140° F. (60° C.).

The concentrations of peroxyoctanoic acid reported in the present examples were determined by a well established and standardized titration protocol. First, hydrogen peroxide content was determined by an oxidation-reduction titration with potassium permanganate. After the endpoint of this titration was reached, an excess of potassium iodide was added to the solution. The potassium iodide reacts with peroxycarboxylic acids to liberate iodine. The liberated iodine was titrated with a standard solution of sodium thiosulfate to yield the concentration of peroxycarboxylic acid. The remaining level of carboxylic acid can be (and was) calculated.

The peroxycarboxylic acid was titrated at a time after formulation that was practical in the laboratory. For example, the peroxycarboxylic acid was titrated for compositions AB, AD, AE, AF, AG, AH, AK, AL, AO, AP, AQ, AU, AV, AZ, BC, and BD after the sample had sat at room temperature for 0, 2 (BD), or 3 (AP, AU, and AV) days. For example, the peroxycarboxylic acid was titrated for compositions AC and BG-BK after the sample had sat at 100° F. for 4 days (AC) or 7 days (BG-BK). For example, the peroxycarboxylic acid was titrated for compositions AI, AN, AR, BE and BF after the sample had sat at 140° F. (60° C.) for 1 day (AI, AR, and BE) or 4 days (AN and BF).

For composition AB, no decomposition of peroxycarboxylic acid was observed upon aging the composition for 7 days at 140° F. (60° C.). For composition AC, no decomposition of peroxycarboxylic acid was observed upon aging the composition for 34 days at 100° F. Other compositions were also observed to include stable peroxycarboxylic acid.

The octanoic acid employed in the present examples was obtained from sources including Procter & Gamble Chemicals and includes a minimum of 95% octanoic acid with minor amounts of hexanoic acid (ca. 2%), decanoic acid (ca. 2%), and dodecanoic acid (<0.5%).

Fragrance

Certain of the compositions were evaluated for phase stability and for smell after addition of a fragrance. In particular, compositions AB and AG were evaluated. Fragrances evaluated included Green Meadow (Klabin); Vinegar Mask I (J&E Sozio); Vinegar Mask II (J&E Sozio); amyl acetate; isobornyl acetate; and methyl salicylate.

Example 6

Antimicrobial Efficacy of the Present Compositions Including Medium Chain Peroxycarboxylic Acid and Solubilizer Additional compositions according to the present invention were evaluated and demonstrated advantageous antimicrobial activity against microbes such as gram negative bacteria, gram positive bacteria, fungi, spores, viruses, and mycobacteria.

TABLE 27

Foaming by the Present Medium Chain Peroxycarboxylic Acid Compositions.

| Composition | Amount in Use Solution (oz/gal) | Break Time | Foam Dry Time (min) | Odor | Initial Appearance of Foam | Comments |
|---|---|---|---|---|---|---|
| AB | 0.17 | slow, about 2 min | >10 | moderate | Covers well, wet, about 1/16 inch thick | foam breaks to spotty foam, dries to no visible residue |
| AG | 0.17 | slow, about 2 min | >10 | moderate | Covers well, wet, about 1/16 inch thick | foam breaks to spotty foam, dries to no visible residue |
| AH | 0.17 | faster, <2 min | 95% dry at 10 min | moderate | Covers well, wetter than above | foam breaks to spotty foam, dries to no visible residue |
| AK | 0.17 | fast, about 1 min | 95% dry at 10 min | moderate | Wetter than above | no visible residue |
| AY | 0.17 | fast, about 10 sec | 95% dry at 10 min | strong | Very wet, lays flat | no visible residue |
| AB | 0.13 | fast, <1 min | about 10 min | low | Covers, wet | spotty foam |
| AG | 0.13 | fast, <1 min | about 10 min | low | Covers, wet | streaky foam |
| AH | 0.13 | very fast, <1 min | about 10 min | low | Extremely wet | very spotty foam |
| AK | 0.13 | very fast, <1 min | about 10 min | low | Extremely wet | very spotty foam |
| AY | 0.13 | fast, about 10 sec | 95% dry at 10 min | strong | Very wet, lays flat | no visible residue |

Composition AC included fragrance (1 wt-%), specifically a mint apple fragrance which is believed to be or include an alkyl salicylate. Composition AC altered to include 10 wt-% LAS remained single phase at 40° F., room temperature, and 70° F.

Foaming

The results in Table 27 show that the present medium chain peroxycarboxylic acid composition produced foam with desirable qualities. This study employed a "FOAM IT" brand tank roamer set to produce slightly wet foam, 2 turns from the mid point. The foam was dispensed from use composition at 95-98° F. The foam was sprayed on a vertical stainless steel surface (approximately 15 ft by 15 ft) from a distance of about 10 ft. The results of Table 27 demonstrate that the present compositions provided foam with desirable hang time and density. Each of the compositions tested at 1 oz/6 gal. provided foam with desirable characteristics, such as the breaking foam was visible for about 5 min, the foam drained well from the vertical surface, exhibited good sheeting down vertical surface, and dried evenly to no visible residue.

Materials and Methods

Antimicrobial activity was determined as described above in Example 4.

Results

Tables 28-29 include data showing that the present medium chain peroxycarboxylic acid compositions had antimicrobial activity when tested against bacteria, fungi, and spores in several different types of tests.

The data presented in Table 28 demonstrate that the present compositions exhibited significant antimicrobial activity. Test 1 included 5 min exposure of the microbe to composition AB at room temperature. The microbes in test 1 included *E. aerogenes* ATCC 13048 and *S. aureus* ATCC 6538. Test 2 included 30 sec exposure of the microbe to composition AB at room temperature. The microbes in test 2 included *S. aureus* ATCC 6538, *E. coli* ATCC 11229, and *P. aeruginosa* ATCC 13442.

The data presented in Table 29 demonstrate sporicidal activity of a composition according to the present invention.

Tests against Poliovirus Type I resulted in complete kill of this virus. The virus was dried onto a hard surface. The virus on the hard surface was contacted for 10 min with composition AG diluted at 1 oz per 1 gallon or 1 oz per 0.5 gallons. Composition AG demonstrated complete inactivation of Poliovirus type 1 following either 3 min or 5 min exposure at 20° C. The composition produced >6 and >5.3 log reduction in 3 and 5 min, respectively. Virus and cells survived in appropriate controls. These results indicate that the present compositions are effective general virucides.

The compositions that included fragrance showed no negative effect on antimicrobial efficacy from the fragrance. Several additional compositions were tested for antimicrobial activity and exhibited results similar to those reported in this Example.

TABLE 28

Activity of Composition AB against Several Microorganisms

| Test | Dilution | Log Reduction of E. aerogenes | Log Reduction of S. aureus | Log Reduction of E. coli | Log Reduction of P. aeruginosa |
|---|---|---|---|---|---|
| 1 | 500 ppm in synthetic hard water | 4.5 | 5.4 | | |
| 2 | 1 oz/9 gal water | | >6.7 | >7.3 | 5.8 |
| 2 | 1 oz/9.5 gal water | | >6.7 | >7.3 | 5.7 |
| 2 | 1 oz/10 gal water | | >6.7 | >7.3 | 5.2 |
| 2 | 1 oz/10.5 galwater | | >6.7 | >7.3 | 1.7 |

TABLE 29

Activity of Composition KK against Spores of B. subtilis ATCC 49760

| Composition | Dilution | Exposure Time (min) | Log Reduction of B. subtilis spores |
|---|---|---|---|
| KK plus 8 wt-% NAS FAL | 1 oz/6 gal | 30 | 0.5 |
| | | 60 | 0.6 |
| | | 120 | 0.6 |
| KK plus 10 wt-% LAS | 1 oz/6 gal | 30 | 0.8 |
| | | 60 | 1.5 |
| | | 120 | 3.0 |

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

we claim:

1. A composition consisting of:
   about 0.5 to about 5 wt-% peroxyoctanoic acid;
   about 1 to about 10 wt-% octanoic acid;
   about 5 to about 97 wt-% water;
   about 1 to about 20 wt-% of an anionic surfactant selected from the group consisting of alkyl sulfonate, linear alkyl benzene sulfonic acid, secondary alkane sulfonate, alkylated diphenyl oxide disulfonate, alkyl ether sulfate, and mixtures thereof;
   about 5 to about 10 wt-% hydrogen peroxide and a persulfate;
   about 15 to about 35 wt-% sulfuric acid or methanesulfonic acid; and
   about 1 to about 5 wt-% sequestrant;
   the composition being in the form of a microemulsion, the microemulsion comprising droplets of a diameter of 100 nanometers or less.

2. The composition of claim 1, consisting of:
   about 15 to about 80 wt-% water; and
   about 3 to about 20 wt-% anionic surfactant.

3. The composition of claim 2, comprising:
   about 30 to about 70 wt-% water; and
   about 4 to about 20 wt-% anionic surfactant.

4. The composition of claim 1, consisting of at least about 2 parts by weight of peroxyoctanoic acid for each 7 parts by weight of octanoic acid.

5. The composition of claim 1, wherein the sequestrant comprises HEDP.

6. The composition of claim 1, further consisting of amine oxide, alkyl dimethyl amine, or mixture thereof.

7. The composition of claim 1, further consisting of fragrance, the fragrance comprising amyl acetate, iso-bornyl acetate, alkyl salicylate, or mixture thereof.

8. A composition comprising:
   about 0.0005 to about 5 wt-% peroxyoctanoic acid;
   about 0.001 to about 10 wt-% octanoic acid;
   about 5 to about 99.99 wt-% water;
   about 0.00 1 to about 20 wt-% anionic surfactant selected from the group consisting of alkyl sulfonate, linear alkyl benzene sulfonic acid, secondary alkane sulfonate, alkylated diphenyl oxide disulfonate, alkyl ether sulfate, and mixtures thereof;
   about 0.002 to about 10 wt-% hydrogen peroxide and a persulfate;
   about 0.00 1 to about 30 wt-% sulfuric acid or methane sulfonic acid; and
   about 0.001 to about 5 wt-% sequestrant;
   the composition comprising at least about 2 parts by weight of peroxyoctanoic acid for each 7 parts by weight of octanoic acid.

9. The composition of claim 8, comprising:
   about 2 to about 500 ppm peroxyoctanoic acid;
   about 5 to about 2000 ppm octanoic acid;
   about 95 to about 99.99 wt-% water; and
   about 2 to about 23,000 ppm of the anionic surfactant.

10. The composition of claim 8, comprising about 2 parts by weight of peroxyoctanoic acid for each 3 parts by weight of octanoic acid.

11. The composition of claim 8, wherein the oxidizing agent comprises hydrogen peroxide.

12. The composition of claim 8, wherein the sequestrant comprises HEDP.

13. The composition of claim 8, further consisting of amine oxide, alkyl dimethyl amine, or mixture thereof.

14. The composition of claim 8, further comprising fragrance, the fragrance comprising amyl acetate, iso-bomyl acetate, alkyl salicylate, or mixture thereof.

* * * * *